United States Patent [19]
Klis et al.

[11] Patent Number: 6,027,910
[45] Date of Patent: Feb. 22, 2000

[54] PROCESS FOR IMMOBILIZING ENZYMES TO THE CELL WALL OF A MICROBIAL CELL BY PRODUCING A FUSION PROTEIN

[75] Inventors: Franciscus M Klis, Amsterdam; Maarten P Schreuder, Diemen, both of Netherlands; Holger Y Toschka, Reken, Germany; Cornelis T Verrips, Maassluis, Netherlands

[73] Assignee: Unilever Patent Holdings B.V., Vlaardingen, Netherlands

[21] Appl. No.: 08/362,525

[22] PCT Filed: Jul. 7, 1993

[86] PCT No.: PCT/EP93/01763

§ 371 Date: Feb. 27, 1995

§ 102(e) Date: Feb. 27, 1995

[87] PCT Pub. No.: WO94/01567

PCT Pub. Date: Jan. 20, 1994

[30] Foreign Application Priority Data

Jul. 8, 1992 [EP] European Pat. Off. ............... 92202080
Dec. 14, 1992 [EP] European Pat. Off. ............... 92203899

[51] Int. Cl.[7] ............................. C12N 15/00; C12N 1/20; C12P 1/00

[52] U.S. Cl. ......................... 435/41; 435/69.7; 435/69.8; 435/69.9; 435/172.1; 435/172.3; 435/252.3; 435/320.1

[58] Field of Search ................... 435/69.7, 69.8, 435/71.1, 71.2, 172.1, 252.1, 252.3, 252.33, 320.1, 183, 69.9, 189, 195, 198, 41, 172.3

[56] References Cited

U.S. PATENT DOCUMENTS 5,348,867 9/1994 Geogiou et al. ....................... 435/69.7

FOREIGN PATENT DOCUMENTS 8907140 8/1989 WIPO .

OTHER PUBLICATIONS

Pelham, H. R. B. "Control of protein exit from endoplasmic reticulum" Ann. Rev. Cell Biol. 5, 1–23, 1989.
Martineau et al. "A Genetic System to Elicit and Monitor Antipep . . . " Bio/technology 9, 170–172, Feb. 1991.
Lipke et al. AGα1 is the structural gene for the *Saccaromyces cervisiae* α–agglutinin, . . . , Mol. and Cell. Biol. 9 (8), 3155–3165, Aug. 1989.
Francisco, Joseph A.; Proceedings of the National Academy of Sciences of USA; vol. 89; Apr. 1992; Washington, US; pp. 2713–2717.
George et al; Journal of Bacteriology; vol. 171; No. 9; Sep. 1989; pp. 4569–4576.
Hiebert, Scott W. et al; Journal of Cell Biology; vol. 107; Sep. 1988; pp. 865–876.
Chen, Cecil C. et al; Journal of Biological Chemistry; vol. 265; No. 6; Feb. 25, 1990; Baltimore US; pp. 3161–3167.
EMR, Scott D. et al; Chemical Abstracts; vol. 102; No. 3; Jan. 21, 1985; Columbus, Ohio, US; abstract No. 18728c.
S. Vijaya et al; Molecular and Cellular Biology; vol. 8; No. 4; Apr. 1988; Washington, US; pp. 1709–1714.

*Primary Examiner*—Eric Grimes
*Assistant Examiner*—Nashaat T. Nashed
*Attorney, Agent, or Firm*—Cushman Darby & Cushman IP Group of Pillsbury Madison & Sutro

[57] ABSTRACT

A method is provided for immobilizing an enzyme, comprising immobilizing the enzyme or a functional part thereof to the cell wall of a microbial cell using recombinant DNA techniques. The enzyme is immobilized by linking it to the C-terminal part of a protein that ensures anchoring in the cell wall. Also provided is a recombinant polynucleotide comprising a structural gene encoding an enzyme protein, a part of a gene encoding the C-terminal part of a protein capable of anchoring in a eukaryotic or prokaryotic cell wall, as well as a signal sequence, in addition to a chimeric protein encoded by the recombinant polynucleotide and a vector and a microorganism containing the polynucleotide. The microorganism is suitable for carrying out enzymatic processes on an industrial scale.

17 Claims, 24 Drawing Sheets

FIG. IA

```
   1 AAGCTTTAGG TAAGGGAGGC AGGGGGAAAA GATACTGAAA
  41 TGACGGAAAA CGAGAATATG GAGCAGGGAG CAACTTTTAG
  81 AGCTTTACCC GTTAAAAGGT CAAATCGAGG CTTCCTGCCT
 121 TTGTCTGATT TTAGTAGTAC CGGAAGGTTT ATTACGCCCA
 161 AGAACAGTGC TTGAATTGAG TTCTCGGGAC ACGGGAAAGA
 201 CAATGGAAGA AAAATTTACA TTCAGTAGCC TTATATATGA
 241 AATGCTGCCA AGCCACGTCT TTATAAGTAG ATAATGTCCC
 281 ATGAGCTGAA CTATGGGAAT TTATGACGCA GTTCATTGTA
 321 TATATATTAC ATTAACTCTT TAGTTTAACA TCTGAATTGT
 361 TTTATAAAAT AACTTTTTGA ATTTTTTTAT GATCGCTTAG
 401 TTAAGTCTAT TATATCAGGT TTTTTCATTC ATCATAATTG
 441 TTCGTTAAAT ATGAGTATAT TTAAATACAG GAATTAGTAT
 481 CATTTGCAGT CACGAAAAGG GCCGTTTCAT AGAGAGTTTT
 521 CTTAATAAAG TTGAGGGTTT CCGTGATAGT TTTGAGGGT
 561 TGTTTAACT AGATTTACGC TTACCTTTCA ACTGATTAAT
 601 TTTTTCAGCG GGCTTATCAT AATCATCCAT CATAGCAGTC
 641 TTTCTGGACT TCGTCGAGGA CTGGCTTTCT GAATTTTGAC
 681 GGTCCCTATT AGCTCCAGTT GGAGGAATTG AGTTACCTAC
 721 AACTGGCAAG AGGTCTTTGT TTGGATTCAA AATAGGACTT
 761 TGTGGTAGCA GTTTGGTTTT ATTCAATCTA AAGATATGAG
 801 AAACAGGTTT TAAGTAAATC GATACTATTG TACCAATGTT
 841 TAGCTCCAAT TCCTCCAAAA CGGTGGGATC TAATTTTGTG
 881 TTCATTTCTA TTAGTGGCAA CTCTCCGTCC AGTACTGATT
 921 TTAAAGATTC AAAAGTTATC GCGTTTGATA TACGAGACGT
 961 TTTCGTTAAT GACAGCAATC TCCAATACAT CAGTGTTTTA
1001 TCTCTTAAGT CAGGATTATT TTCGTGATCG GTGCATCCTT
1041 TTAATAAATC CATACAAAGT TCTTCAGTTT CCTTTGTAGG
1081 ATTTCTGATG AAGAATTTTA TTGCTGAGTT CAGAATGGAA
1121 AATTGCACTT CTAGCGTCTC ATTAAACATG TTTGAGGAAA
1161 AAACTCTAAA TAACTCCAGG TAGTTTGGAA TTACATCCGA
1201 ATATTGCGTT ATTATCCAGA TCATAGCGTT TTTTGATTCA
1241 GGTTCCTGTA CAACTTCAGT GTGTTTGACT AGTTCTGTTA
1281 CGTTTGCTTT AAAATTATTG GGATATTTCC TCAAAATATT
1321 TCTGAAAACC GAAATAATCT CCTGGACGAC ATAATCAACA
1361 CCGAATTCTA ACAAATCTAG TAGCACAGCG ACACAATCGT
1401 GTACAGAGTC TTCATCTAGC TTAACAGCGA GATTACCAAT
1441 GGCTCTGACT GATTTCCTTG ACATTTGAAT ATCAATATCT
1481 GTAGCATATT GTTCCAACTC TTCTAGAATT CTTGGTAATG
1521 TTTCCTTGTT AGCTAAAAGA TATAAACACT CTAATTTCGT
1561 GTCTTTGATG TATATGGGGT CATTGTACTC GATGAAAAAA
```

FIG.IB

```
1601  TACGAAATGT  CTAGCCTGAG  TAGAGATGAC  TCCCTACTCA
1641  ATAAAAGAAG  AATAACGTTT  CTTAATACTA  AAAATTGTAA
1681  TTCAGGCGGC  TTATCTAACA  AAGCTATTAC  AGAGTTAGAT
1721  AGCTTTTCGG  CTAGAGTTTC  TTTGATGACG  TCAACATAAT
1761  TCAACAAGTA  CATGATGAAT  TTTAAAGAGT  TCAACACTAC
1801  GTATGTGTTT  ACTTGTTGCA  GGTACGGTAA  AGCTAGTTCG
1841  ATCATTTCAT  GGGTATCCAA  ATAATGCTGC  GGCACAACCG
1881  AAGTCGTCAA  AACTTCCAAA  ACAGTAGCCT  TATTCCACTC
1921  ATTTAATTCG  GGTAAAAGTT  CTAGCATGTC  AAAAGCGAGT
1961  TCCAAGGGAA  TCCTGAAGGT  TCCATGTTAG  CGTTTTTTTC
2001  GTGAATGGAA  TATAAAGTAT  GTAATGCAGC  TACAATGACT
2041  TCTGGAGAGC  TCGACTGTGC  CTTTACAATG  TCATGTAGAA
2081  TGCTTGATAA  CCCCAATACC  CTTTCATGAT  CAATTTCATC
2121  TAAATCCAAC  AGTGCGTAAA  TTGCTGTCCT  CGTCACTTGT
2161  TCAGGTGGAG  ACTTGTGATT  TACCAATGAA  ATGATACAGT
2201  CGAAGGCCTG  ATCAGATAGC  TCTTTCACCG  GGACTAATAC
2241  CAGAGTTCTT  AGTGCCATTA  TTTGTAACTT  TTCATCTCTG
2281  CTTTTGAAAT  CGTCCATTAT  AAATGGCAAA  GCCTCTCTGG
2321  CCTGCTGAGG  TTTTAATGCG  CCGATCACCC  TAATATACTC
2361  ATGGCAAATT  CTTTTCACTT  CTAGATCATC  TTCAATTTGC
2401  CAAAATTTCA  AGAGCTCAGA  AAACAGAAGG  GACATTTCGC
2441  CATAGTTTCC  TAGAACCAAA  TTGGCGATAA  TTTTTCTCAG
2481  AGCATTTTTC  CTTCTTGTTA  TATTCGATTT  AAACTTTTTT
2521  ACTCCAAAAT  GTTGCAGATC  TGTGACGATT  TCATTTGCTT
2561  TATATCTGGC  AAAAACTTTT  TGATCGGACA  TAAGCGAAAT
2601  ACGTCCTATT  AATGAAGTGA  ATGTTCTTGC  TGTATTCCCT
2641  TCTTGTGCAG  TAGATTAATT  CTGTTTCCAG  GCTGCGATAC
2681  TTTGATACCC  AATACTAAAA  GTTGATGATT  TGAACGATCT
2721  CCTATTTCCT  CGCACATTTT  TGGAGCGATA  CCCGGAAGAC
2761  AGAATCGCGA  TGTTAAGAAA  ATAGTTCTGA  TGGCACTAAA
2801  GAGATCATGA  TTAAGGAAAG  GTAAGTGATA  TGCATGAATG
2841  GGAATAGGCT  TTCGAACTTG  ACGATTTAGT  TCCTTATTTC
2881  TATCCATCTA  ATCCTCCAAC  TTCAATAGGC  CTTATCTAGC
2921  TCAGAGCAGT  ATTTAATTGA  GAATAGTAGC  TTAATTGAAA
2961  CCTTACTAAA  AAAGTGTATG  GTTACATAAG  ATAAGGCGTT
3001  AAGAAGAGTA  TACATATGCA  TTATTCATTA  CCAAGACCAC
3041  TATGAATAGT  AATACCATAT  TTAGCTTTTG  AAACTCATGT
3081  TTTCTATTGT  GTTGTTTCAA  ATTCCTCTGT  TAGGCTCAAT
3121  TTAGGTTAAT  TAAATTATAA  AAAAATATAA  AAAATAAAGA
3161  AAGTTTATCC  ATCGGCACCT  CAATTCAATG  GAGTAAACAG
3201  TTTCAACACT  GAGTGGTGAA  ACATTGAACA  ACTACATGCA
3241  GTTTCCCGCC  ACGAGGCAAG  TGTAGGTCCT  TTGTCCATTT
```

FIG. IC

```
3281 CGCTTTGTTT TGCAGGTCAT TGATGACCTA ATTAGGAAGG
3321 TAGAAGCCGC TCCAGCTCAA TAAGGAAATG CTAAGGGTAC
3361 TCGCCTTTGG TGTTTTACCA TACAATGGCA GCTTTATGTC
3401 ACTTCATTCT TCAGTAACGG CGCTTAAATA TTCCCAAAAA
3441 CGTTACAATG GAATTGTTTG ATCATGTAAC GAAATGCAAT
3481 CTTCTAAAAA AAAAGCCATG TGAATCAAAA AAAGATTCCT
3521 TTTAGCATAC TATAAATATG CAAAATGCCC TCTATTTATT
3561 CTAGTAATCG TCCATTCTCA TATCTTCCTT ATATCAGTCG
3601 CCTCGCTTAA TATAGTCAGC ACAAAAGGAA CAACAATTCG
3641 CCAGTTTTCA AAATGTTCAC TTTTCTCAAA ATTATTCTGT
3681 GGCTTTTTTC CTTGGCATTG CCTCTGCTA TAAATATCAA
3721 CGATATCACA TTTTCCAATT TAGAAATTAC TCCACTGACT
3761 GCAAATAAAC AACCTGATCA AGGTTGGACT GCCACTTTTG
3801 ATTTTAGTAT TGCAGATGCG TCTTCCATTA GGGAGGGCGA
3841 TGAATTCACA TTATCAATGC CACATGTTTA TAGGATTAAG
3881 CTATTAAACT CATCGCAAAC AGCTACTATT TCCTTAGCGG
3921 ATGGTACTGA GGCTTTCAAA TGCTATGTTT CGCAACAGGC
3961 TGCATACTTG TATGAAAATA CTACTTTCAC ATGTACTGCT
4001 CAAAATGACC TGTCCTCCTA TAATACGATT GATGGATCCA
4041 TAACATTTTC GCTAAATTTT AGTGATGGTG GTTCCAGCTA
4081 TGAATATGAG TTAGAAAACG CTAAGTTTTT CAAATCTGGG
4121 CCAATGCTTG TTAAACTTGG TAATCAAATG TCAGATGTGG
4161 TGAATTTCGA TCCTGCTGCT TTTACAGAGA ATGTTTTTCA
4201 CTCTGGGCGT TCAACTGGTT ACGGTTCTTT TGAAAGTTAT
4241 CATTTGGGTA TGTATTGTCC AAACGGATAT TTCCTGGGTG
4281 GTACTGAGAA GATTGATTAC GACAGTTCCA ATAACAATGT
4321 CGATTTGGAT TGTTCTTCAG TTCAGGTTTA TTCATCCAAT
4361 GATTTTAATG ATTGGTGGTT CCCGCAAAGT TACAATGATA
4401 CCAATGCTGA CGTCACTTGT TTTGGTAGTA ATCTGTGGAT
4441 TACACTTGAC GAAAACTAT ATGATGGGA AATGTTATGG
4481 GTTAATGCAT TACAATCTCT ACCCGCTAAT GTAAACACAA
4521 TAGATCATGC GTTAGAATTT CAATACACAT GCCTTGATAC
4561 CATAGCAAAT ACTACGTACG CTACGCAATT CTCGACTACT
4601 AGGGAATTTA TTGTTTATCA GGGTCGGAAC CTCGGTACAG
4641 CTAGCGCCAA AAGCTCTTTT ATCTCAACCA CTACTACTGA
4681 TTTAACAAGT ATAAACACTA GTGCGTATTC CACTGGATCC
4721 ATTTCCACAG TAGAAACAGG CAATCGAACT ACATCAGAAG
4761 TGATCAGTCA TGTGGTGACT ACCAGCACAA AACTGTCTCC
4801 AACTGCTACT ACCAGCCTGA CAATTGCACA AACCAGTATC
4841 TATTCTACTG ACTCAAATAT CACAGTAGGA ACAGATATTC
4881 ACACCACATC AGAAGTGATT AGTGATGTGG AAACCATTAG
4921 CAGAGAAACA GCTTCGACCG TTGTAGCCGC TCCAACCTCA
```

FIG. ID

```
4961 ACAACTGGAT GGACAGGCGC TATGAATACT TACATCCCGC
5001 AATTTACATC CTCTTCTTTC GCAACAATCA ACAGCACACC
5041 AATAATCTCT TCATCAGCAG TATTTGAAAC CTCAGATGCT
5081 TCAATTGTCA ATGTGCACAC TGAAAATATC ACGAATACTG
5121 CTGCTGTTCC ATCTGAAGAG CCCACTTTTG TAAATGCCAC
5161 GAGAAACTCC TTAAATTCCT TCTGCAGCAG CAAACAGCCA
5201 TCCAGTCCCT CATCTTATAC GTCTTCCCCA CTCGTATCGT
5241 CCCTCTCCGT AAGCAAAACA TTACTAAGCA CCAGTTTTAC
5281 GCCTTCTGTG CCAACATCTA ATACATATAT CAAAACGGAA
5321 AATACGGGTT ACTTTGAGCA CACGGCTTTG ACAACATCTT
5361 CAGTTGGCCT TAATTCTTTT AGTGAAACAG CACTCTCATC
5401 TCAGGGAACG AAAATTGACA CCTTTTTAGT GTCATCCTTG
5441 ATCGCATATC CTTCTTCTGC ATCAGGAAGC CAATTGTCCG
5481 GTATCCAACA GAATTTCACA TCAACTTCTC TCATGATTTC
5521 AACCTATGAA GGTAAAGCGT CTATATTTTT CTCAGCTGAG
5561 CTCGGTTCGA TCATTTTTCT GCTTTTGTCG TACCTGCTAT
5601 TCTAAAACGG GTACTGTACA GTTAGTACAT TGAGTCGAAA
5641 TATACGAAAT TATTGTTCAT AATTTTCATC CTGGCTCTTT
5681 TTTTCTTCAA CCATAGTTAA ATGGACAGTT CATATCTTAA
5721 ACTCTAATAA TACTTTTCTA GTTCTTATCC TTTTCCGTCT
5761 CACCGCAGAT TTTATCATAG TATTAAATTT ATATTTTGTT
5801 CGTAAAAAGA AAAATTTGTG AGCGTTACCG CTCGTTTCAT
5841 TACCCGAAGG CTGTTTCAGT AGACCACTGA TTAAGTAAGT
5881 AGATGAAAAA ATTTCATCAC CATGAAAGAG TTCGATGAGA
5921 GCTACTTTTT CAAATGCTTA ACAGCTAACC GCCATTCAAT
5961 AATGTTACGT TCTCTTCATT CTGCGGCTAC GTTATCTAAC
6001 AAGAGGTTTT ACTCTCTCAT ATCTCATTCA AATAGAAAGA
6041 ACATAATCAA AAAGCTT 6057
```

1  2  3

1  2  3  4

MW
(kD)

— 224

— 109

— 46

— 29

FIG. 6A
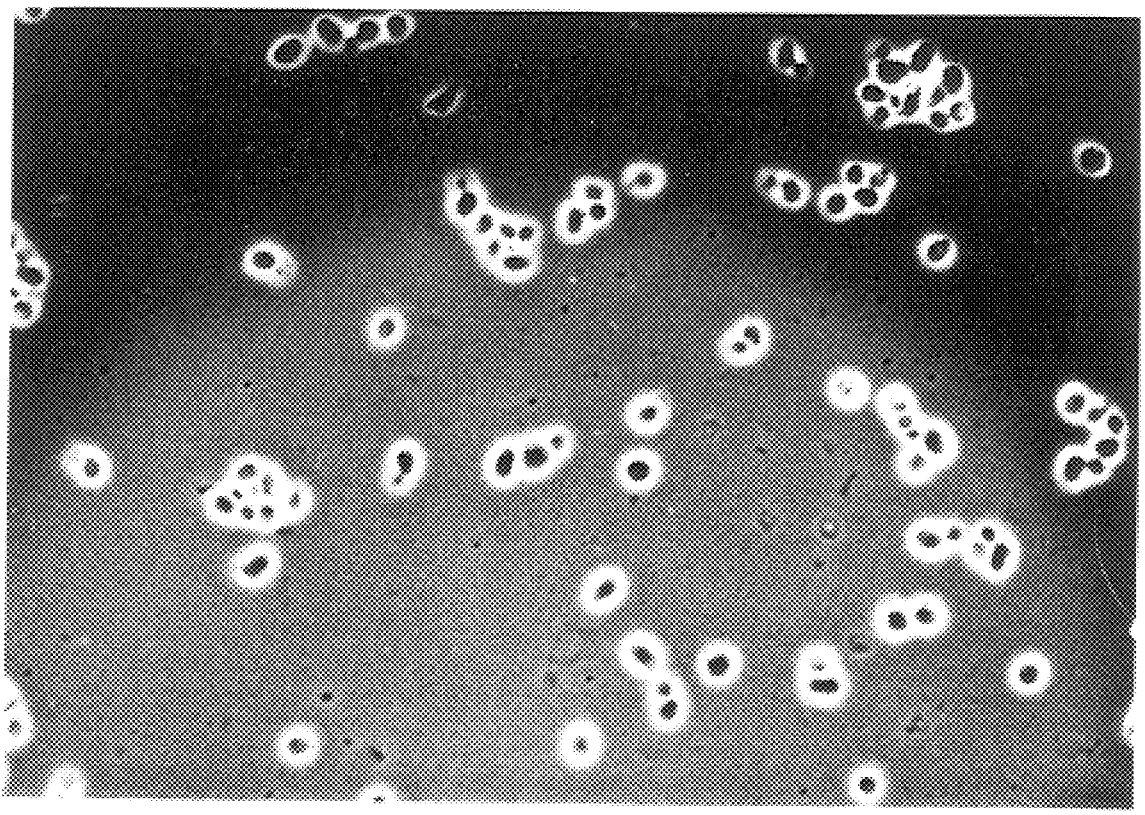
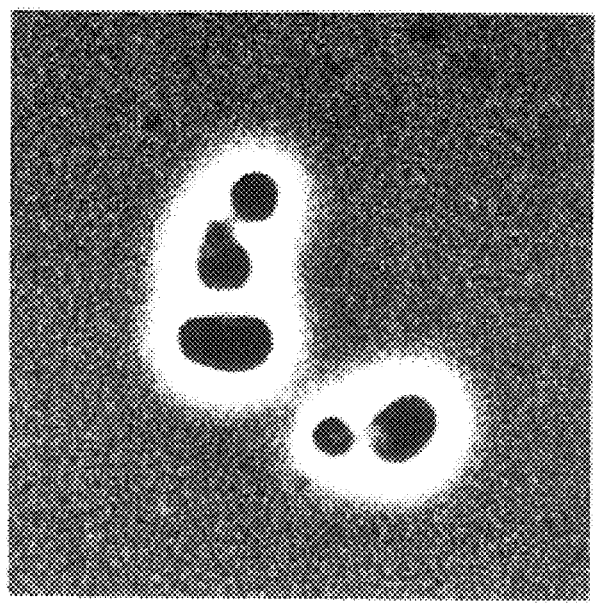
FIG. 6B

FIG. 8A

```
   1 AATTCGGCAC GAGATTCCTT TGATTTGCAA CTGTTAATCA
  41 TGGTTTCCAA AAGCTTTTTT TTGGCTGCGG CGCTCAACGT
  81 AGTGGGCACC TTGGCCCAGG CCCCCACGGC CGTTCTTAAT
 121 GGCAACGAGG TCATCTCTGG TGTCCTTGAG GGCAAGGTTG
 161 ATACCTTCAA GGGAATCCCA TTTGCTGACC CTCCTGTTGG
 201 TGACTTGCGG TTCAAGCACC CCCAGCCTTT CACTGGATCC
 241 TACCAGGGTC TTAAGGCCAA CGACTTCAGC TCTGCTTGTA
 281 TGCAGCTTGA TCCTGGCAAT GCCTTTTCTT TGCTTGACAA
 321 AGTAGTGGGC TTGGAAAGA TTCTTCCTGA TAACCTTAGA
 361 GGCCCTCTTT ATGACATGGC CAGGGTAGT GTCTCCATGA
 401 ATGAGGACTG TCTCTACCTT AACGTTTTCC GCCCCGCTGG
 441 CACCAAGCCT GATGCTAAGC TCCCCGTCAT GGTTTGGATT
 481 TACGGTGGTG CCTTTGTGTT TGGTTCTTCT GCTTCTTACC
 521 CTGGTAACGG CTACGTCAAG GAGAGTGTGG AAATGGGCCA
 561 GCCTGTTGTG TTTGTTTCCA TCAACTACCG TACCGGCCCC
 601 TATGGATTCT TGGGTGGTGA TGCCATCACC GCTGAGGGCA
 641 ACACCAACGC TGGTCTGCAC GACCAGCGCA AGGGTCTCGA
 681 GTGGGTTAGC GACAACATTG CCAACTTTGG TGGTGATCCC
 721 GACAAGGTCA TGATTTTCGG TGAGTCCGCT GGTGCCATGA
 761 GTGTTGCTCA CCAGCTTGTT GCCTACGGTG GTGACAACAC
 801 CTACAACGGA AAGCAGCTTT TCCACTCTGC CATTCTTCAG
 841 TCTGGCGGTC CTCTTCCTTA CTTTGACTCT ACTTCTGTTG
 881 GTCCCGAGAG TGCCTACAGC AGATTTGCTC AGTATGCCGG
 921 ATGTGACACC AGTGCCAGTG ATAATGACAC TCTGGCTTGT
 961 CTCCGCAGCA AGTCCAGCGA TGTCTTGCAC AGTGCGCAGA
1001 ACTCGTATGA TCTTAAGGAC CTGTTTGGTC TGCTCCCTCA
1041 ATTCCTTGGA TTTGGTCCCA GACCCGACGG CAACATTATT
1081 CCCGATGCCG CTTATGAGCT CTACCGCAGC GGTAGATACG
1121 CCAAGGTTCC CTACATTACT GGCAACCAGG AGGATGAGGG
1161 TACTATTCTT GCCCCGTTG CTATTAATGC TACCACTACT
1201 CCCCATGTTA AGAAGTGGTT GAAGTACATT TGTAGCCAGG
1241 CTTCTGACGC TTCGCTTGAT CGTGTTTTGT CGCTCTACCC
1281 CGGCTCTTGG TCGGAGGGTT CACCATTCCG CACTGGTATT
1321 CTTAATGCTC TTACCCCTCA GTTCAAGCGC ATTGCTGCCA
1361 TTTTCACTGA TTTGCTGTTC CAGTCTCCTC GTCGTGTTAT
1401 GCTTAACGCT ACCAAGGACG TCAACCGCTG GACTTACCTT
1441 GCCACCCAGC TCCATAACCT CGTTCCATTT TTGGGTACTT
1481 TCCATGGCAG TGATCTTCTT TTTCAATACT ACGTGGACCT
1521 TGGCCCATCT TCTGCTTACC GCCGCTACTT TATCTCGTTT
1561 GCCAACCACC ACGACCCCAA CGTTGGTACC AACCTCCAAC
```

FIG. 8B

```
1601 AGTGGGATAT GTACACTGAT GCAGGCAAGG AGATGCTTCA
1641 GATTCATATG ATTGGTAACT CTATGAGAAC TGACGACTTT
1681 AGAATCGAGG GAATCTCGAA CTTTGAGTCT GACGTTACTC
1721 TCTTCGGTTA ATCCCATTTA GCAAGTTTTG TGTATTTCAA
1761 GTATACCAGT TGATGTAATA TATCAATAGA TTACAAATTA
1801 ATTAGTGAAA AAAAAAAAAA AAAAAAC    1828
```

FIG. IIA

```
   1 ATGACAATGC CTCATCGCTA TATGTTTTTG GCAGTCTTTA
  41 CACTTCTGGC ACTAACTAGT GTGGCCTCAG GAGCCACAGA
  81 GGCGTGCTTA CCAGCAGGCC AGAGGAAAAG TGGGATGAAT
 121 ATAAATTTTT ACCAGTATTC ATTGAAAGAT TCCTCCACAT
 161 ATTCGAATGC AGCATATATG GCTTATGGAT ATGCCTCAAA
 201 AACCAAACTA GGTTCTGTCG GAGGACAAAC TGATATCTCG
 241 ATTGATTATA ATATTCCCTG TGTTAGTTCA TCAGGCACAT
 281 TTCCTTGTCC TCAAGAAGAT TCCTATGGAA ACTGGGGATG
 321 CAAAGGAATG GGTGCTTGTT CTAATAGTCA AGGAATTGCA
 361 TACTGGAGTA CTGATTTATT TGGTTTCTAT ACTACCCCAA
 401 CAAACGTAAC CCTAGAAATG ACAGGTTATT TTTTACCACC
 441 ACAGACGGGT TCTTACACAT TCAAGTTTGC TACAGTTGAC
 481 GACTCTGCAA TTCTATCAGT AGGTGGTGCA ACCGCGTTCA
 521 ACTGTTGTGC TCAACAGCAA CCGCCGATCA CATCAACGAA
 561 CTTTACCATT GACGGTATCA AGCCATGGGG TGGAAGTTTG
 601 CCACCTAATA TCGAAGGAAC CGTCTATATG TACGCTGGCT
 641 ACTATTATCC AATGAAGGTT GTTACTCGA ACGCTGTTTC
 681 TTGGGGTACA CTTCCAATTA GTGTGACACT TCCAGATGGT
 721 ACCACTGTAA GTGATGACTT CGAAGGGTAC GTCTATTCCT
 761 TTGACGATGA CCTAAGTCAA TCTAACTGTA CTGTCCCTGA
 801 CCCTTCAAAT TATGCTGTCA GTACCACTAC AACTACAACG
 841 GAACCATGGA CCGGTACTTT CACTTCTACA TCTACTGAAA
 881 TGACCACCGT CACCGGTACC AACGGCGTTC AACTGACGA
 921 AACCGTCATT GTCATCAGAA CTCCAACCAG TGAAGGTCTA
 961 ATCAGCACCA CCACTGAACC ATGGACTGGC ACTTTCACTT
1001 CGACTTCCAC TGAGGTTACC ACCATCACTG GAACCAACGG
1041 TCAACCAACT GACGAAACTG TGATTGTTAT CAGAACTCCA
1081 ACCAGTGAAG GTCTAATCAG CACCACCACT GAACCATGGA
1121 CTGGTACTTT CACTTCTACA TCTACTGAAA TGACCACCGT
1161 CACCGGTACT AACGGTCAAC CAACTGACGA AACCGTGATT
1201 GTTATCAGAA CTCCAACCAG TGAAGGTTTG GTTACAACCA
1241 CCACTGAACC ATGGACTGGT ACTTTTACTT CGACTTCCAC
1281 TGAAATGTCT ACTGTCACTG GAACCAATGG CTTGCCAACT
1321 GATGAAACTG TCATTGTTGT CAAAACTCCA ACTACTGCCA
1361 TCTCATCCAG TTTGTCATCA TCATCTTCAG GACAAATCAC
1401 CAGCTCTATC ACGTCTTCGC GTCCAATTAT TACCCCATTC
1441 TATCCTAGCA ATGGAACTTC TGTGATTTCT TCCTCAGTAA
1481 TTTCTTCCTC AGTCACTTCT TCTCTATTCA CTTCTTCTCC
1521 AGTCATTTCT TCCTCAGTCA TTTCTTCTTC TACAACAACC
1561 TCCACTTCTA TATTTTCTGA ATCATCTAAA TCATCCGTCA
```

FIG. 11B

```
1601 TTCCAACCAG TAGTTCCACC TCTGGTTCTT CTGAGAGCGA
1641 AACGAGTTCA GCTGGTTCTG TCTCTTCTTC CTCTTTTATC
1681 TCTTCTGAAT CATCAAAATC TCCTACATAT TCTTCTTCAT
1721 CATTACCACT TGTTACCAGT GCGACAACAA GCCAGGAAAC
1761 TGCTTCTTCA TTACCACCTG CTACCACTAC AAAAACGAGC
1801 GAACAAACCA CTTTGGTTAC CGTGACATCC TGCGAGTCTC
1841 ATGTGTGCAC TGAATCCATC TCCCCTGCGA TTGTTTCCAC
1881 AGCTACTGTT ACTGTTAGCG GCGTCACAAC AGAGTATACC
1921 ACATGGTGCC CTATTTCTAC TACAGAGACA ACAAAGCAAA
1961 CCAAAGGGAC AACAGAGCAA ACCACAGAAA CAACAAAACA
2001 AACCACGGTA GTTACAATTT CTTCTTGTGA ATCTGACGTA
2041 TGCTCTAAGA CTGCTTCTCC AGCCATTGTA TCTACAAGCA
2081 CTGCTACTAT TAACGGCGTT ACTACAGAAT ACACAACATG
2121 GTGTCCTATT TCCACCACAG AATCGAGGCA ACAAACAACG
2161 CTAGTTACTG TTACTTCCTG CGAATCTGGT GTGTGTTCCG
2201 AAACTGCTTC ACCTGCCATT GTTTCGACGG CCACGGCTAC
2241 TGTGAATGAT GTTGTTACGG TCTATCCTAC ATGGAGGCCA
2281 CAGACTGCGA ATGAAGAGTC TGTCAGCTCT AAAATGAACA
2321 GTGCTACCGG TGAGACAACA ACCAATACTT TAGCTGCTGA
2361 AACGACTACC AATACTGTAG CTGCTGAGAC GATTACCAAT
2401 ACTGGAGCTG CTGAGACGAA AACAGTAGTC ACCTCTTCGC
2441 TTTCAAGATC TAATCACGCT GAAACACAGA CGGCTTCCGC
2481 GACCGATGTG ATTGGTCACA GCAGTAGTGT TGTTTCTGTA
2521 TCCGAAACTG GCAACACCAA GAGTCTAACA AGTTCCGGGT
2561 TGAGTACTAT GTCGCAACAG CCTCGTAGCA CACCAGCAAG
2601 CAGCATGGTA GGATATAGTA CAGCTTCTTT AGAAATTTCA
2641 ACGTATGCTG GCAGTGCAAC AGCTTACTGG CCGGTAGTGG
2681 TTTAA 2685
```

6,027,910

PROCESS FOR IMMOBILIZING ENZYMES TO THE CELL WALL OF A MICROBIAL CELL BY PRODUCING A FUSION PROTEIN

The present invention is in the field of conversion processes using immobilized enzymes, produced by genetic engineering.

BACKGROUND OF THE INVENTION

In the detergent, personal care and food products industry there is a strong trend towards natural ingredients of these products and to environmentally acceptable production processes. Enzymic conversions are very important for fulfilling these consumer demands, as these processes can be completely natural. Moreover enzymic processes are very specific and consequently will produce minimum amounts of waste products. Such processes can be carried out in water at mild temperatures and atmospheric pressure. However enzymic processes based on free enzymes are either quite expensive due to the loss of enzymes or require expensive equipment, like ultra-membrane systems to entrap the enzyme.

Alternatively enzymes can be immobilized either physically or chemically. The latter method has often the disadvantage that coupling is carried out using non-natural chemicals and in processes that are not attractive from an environmental point of view. Moreover chemical modification of enzymes is nearly always not very specific, which means that coupling can affect the activity of the enzyme negatively. Physical immobilization can comply with consumer demands, however also physical immobilization may affect the activity of the enzyme in a negative way. Moreover, a physically immobilized enzyme is in equilibrium with free enzyme, which means that in continuous reactors, according to the laws of thermodynamics, substantial losses of enzyme are unavoidable.

There are a few publications on immobilization of enzymes to microbial cells (see reference 1). The present invention provides a method for immobilizing enzymes to cell walls of microbial cells in a very precise way. Additionally, the immobilization does not require any chemical or physical coupling step and is very efficient. Some extracellular proteins are known to have special functions which they can perform only if they remain bound to the cell wall of the host cell. Often this type of protein has a long C-terminal part that anchors it in the cell wall. These C-terminal parts have very special amino acid sequences. A typical example is anchoring via C-terminal sequences enriched in proline (see reference 2). Another mechanism to anchor proteins in cell walls is that the protein has a glycosyl-phosphatidyl-inositol (GPI) anchor (see reference 3) and that the C-terminal part of the protein contains a substantial number of potential serine and threonine glycosylation sites. O-Glycosylation of these sites gives a rod-like conformation to the C-terminal part of these proteins. Another feature of these manno-proteins is that they seem to be linked to the glucan in the cell wall of lower eukaryotes, as they cannot be extracted from the cell wall with SDS, but can be liberated by glucanase treatment.

SUMMARY OF THE INVENTION

The present invention provides a method for immobilizing an enzyme, which comprises the use of recombinant DNA techniques for producing an enzyme or a functional part thereof linked to the cell wall of a host cell, preferably a microbial cell, and whereby the enzyme or functional fragment thereof is localized at the exterior of the cell wall. Preferably the enzyme or the functional part thereof is immobilized by linking to the C-terminal part of a protein that ensures anchoring in the cell wall.

In one embodiment of the invention a recombinant polynucleotide is provided comprising a structural gene encoding a protein providing catalytic activity and at least a part of a gene encoding a protein capable of anchoring in a eukaryotic or prokaryotic cell wall, said part encoding at least the C-terminal part of said anchoring protein. Preferably the polynucleotide further comprises a sequence encoding a signal peptide ensuring secretion of the expression product of the polynucleotide. Such signal peptide can be derived from a glycosyl-phosphatidyl-inositol (GPI) anchoring protein, α-factor, α-agglutinin, invertase or inulinase, α-amylase of Bacillus, or a proteinase of lactic acid bacteria. The DNA sequence encoding a protein capable of anchoring in the cell wall can encode α-agglutinin, AGA1 (a-agglutinin) FLO1 (flocculation protein) or the Major Cell Wall Protein of lower eukaryotes, or a proteinase of lactic acid bacteria. The recombinant polynucleotide is operably linked to a promoter, preferably an inducible promoter. The DNA sequence encoding a protein providing catalytic activity can encode a hydrolytic enzyme, e.g. a lipase, or an oxidoreductase, e.g. an oxidase. Another embodiment of the invention relates to a recombinant vector comprising a polynucleotide as described above. If such vector contains a DNA sequence encoding a protein providing catalytic activity, which protein exhibits said catalytic activity when present in a multimeric form, said vector can further comprise a second polynucleotide comprising a structural gene encoding the same protein providing catalytic activity combined with a sequence encoding a signal peptide ensuring secretion of the expression product of said second polynucleotide, said second polynucleotide being operably linked to a regulatable promoter, preferably an inducible or repressible promoter.

A further embodiment of the invention relates to a chimeric protein encoded by a polynucleotide as described above.

Still another embodiment is a host cell, preferably a microorganism, containing a polynucleotide as described above or a vector as described above. If the protein providing catalytic activity exhibits said catalytic activity when present in a multimeric form, said host cell or microorganism can further comprise a second polynucleotide comprising a structural gene encoding the same protein providing catalytic activity combined with a sequence encoding a signal peptide ensuring secretion of the expression product of said second polynucleotide, said second polynucleotide being operably linked to a regulatable promoter, preferably an inducible or repressible promoter, and said second polynucleotide being present either in another vector or in the chromosome of said microorganism. Preferably the host cell or microorganism has at least one of said polynucleotides integrated in its chromosome. As a result of culturing such host cell or microorganism the invention provides a host cell, preferably a microorganism, having a protein as described above immobilized on its cell wall. The host cell or microorganism can be a lower eukaryote, in particular a yeast.

The invention also provides a process for carrying out an enzymatic process by using an immobilized catalytically active protein, wherein a substrate for said catalytically active protein is contacted with a host cell or microorganism according to the invention.

BRIEF DESCRIPTION OF THE FIGURES

FIG. 1: DNA sequence of the 6057 bp HindIII fragment containing the complete AGα1 gene of *S. cerevisiae* (see SEQ ID NO: 1). The position of the unique NheI site and the HindIII site used for the described constructions is specified in the header.

Figure 3A:
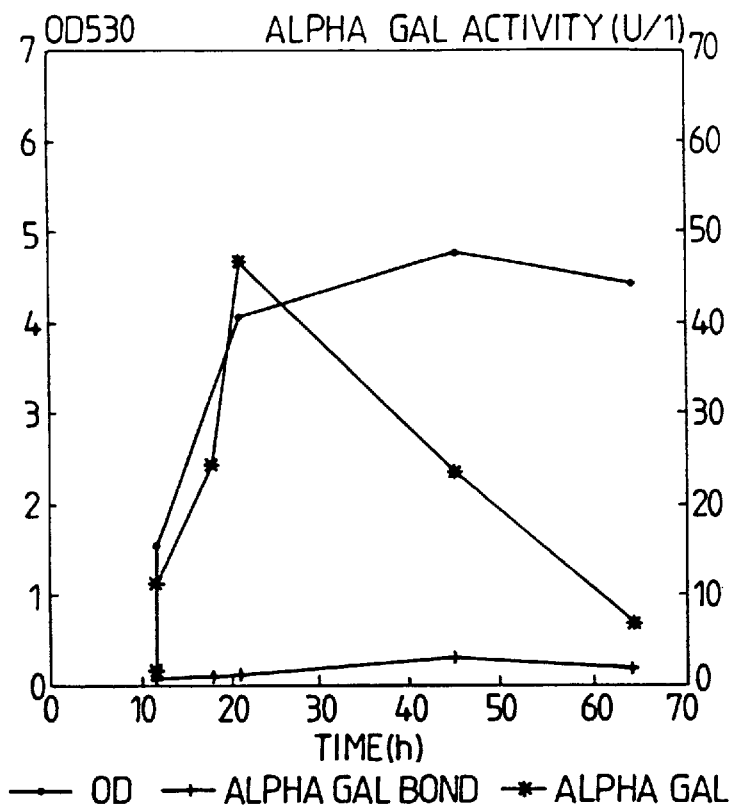
Figure 3B:
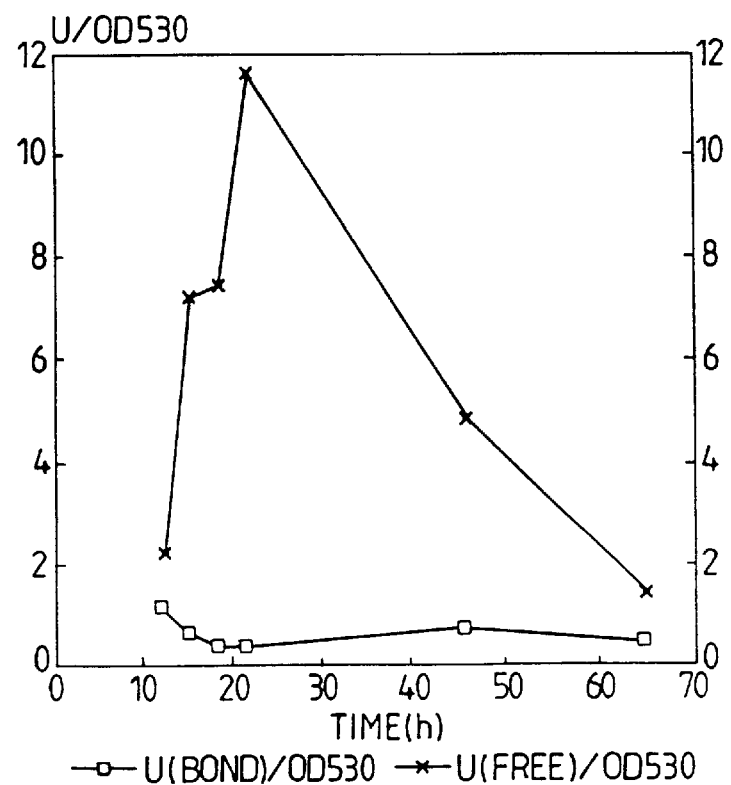

FIG. 3: α-Galactosidase activity of *S. cerevisiae* MT302/1C cells and culture fluid transformed with pSY13 during batch culture:

A: U/l α-galactosidase per time; the $OD_{530}$ is also shown
    B: α-galactosidase activity of free and bond enzyme expressed in $U/OD_{530}$.

Figure 4A:
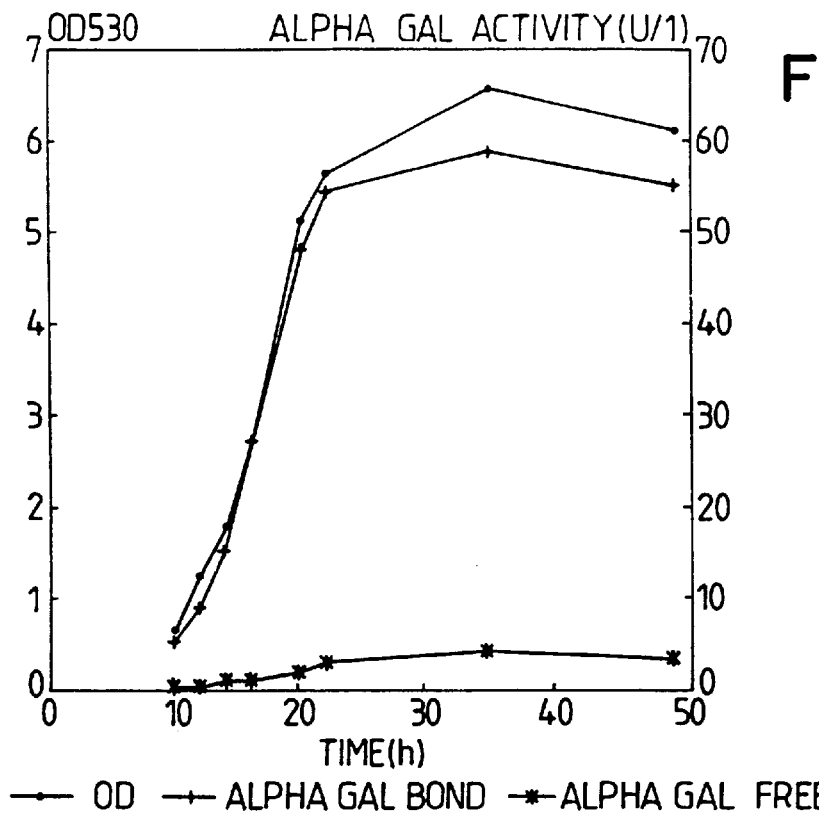
Figure 4B:
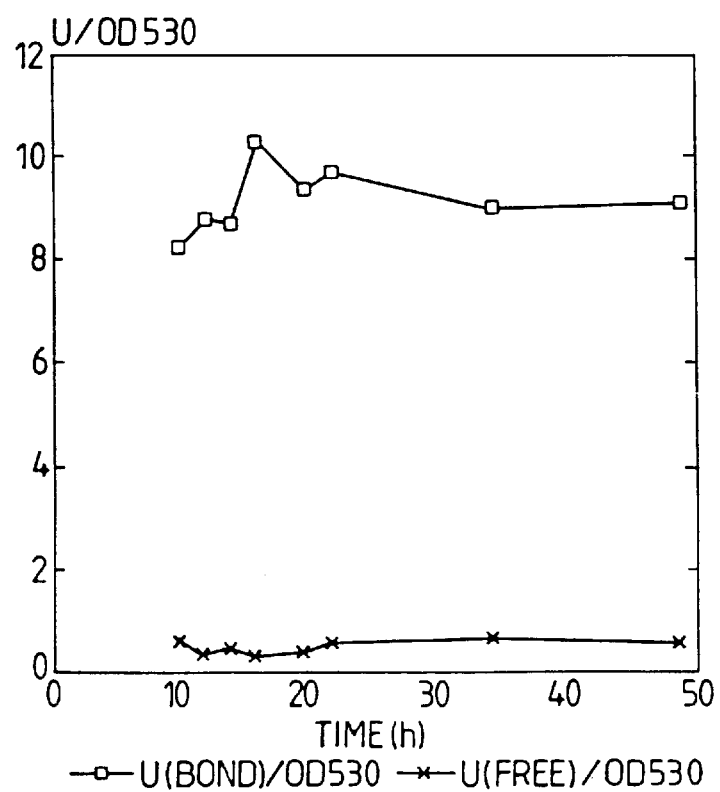

FIG. 4: α-Galactosidase activity of *S. cerevisiae* MT302/1C cells and culture fluid transformed with pUR2969 during batch culture:

A: U/l α-galactosidase per time; the $OD_{530}$ is also shown
    B: α-galactosidase activity of free and bond enzyme expressed in $U/OD_{530}$.

Figure 5A:
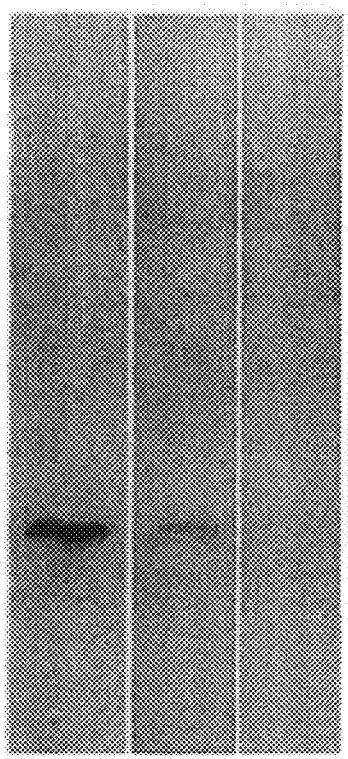
Figure 5B:
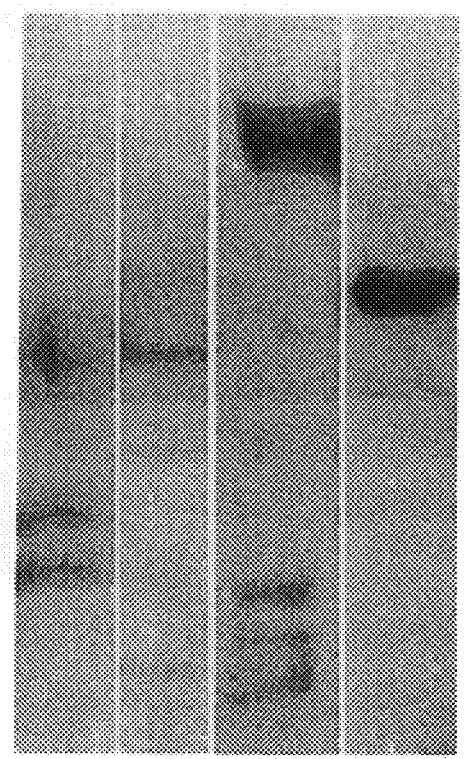
Figure 7A:
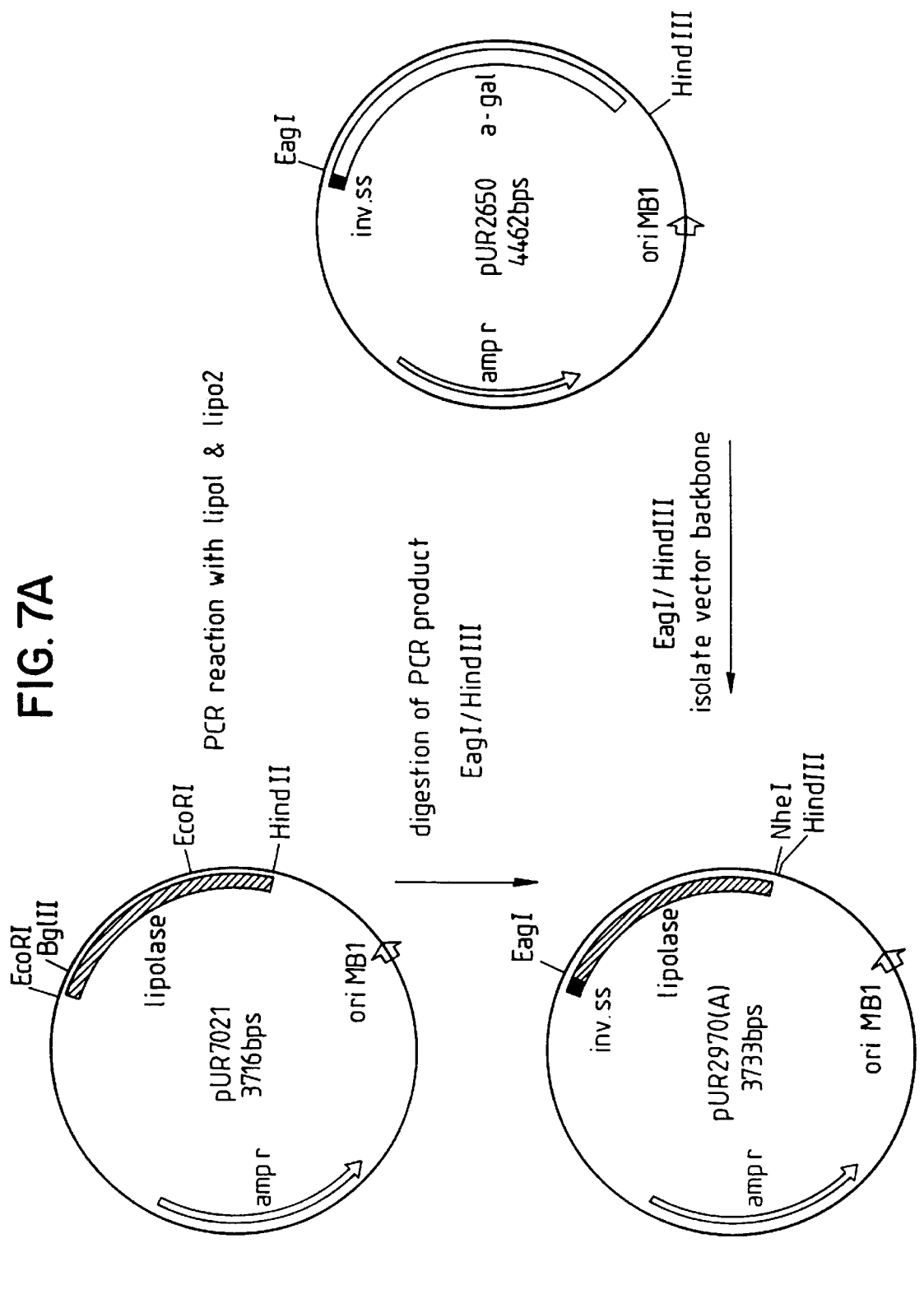
Figure 7B:
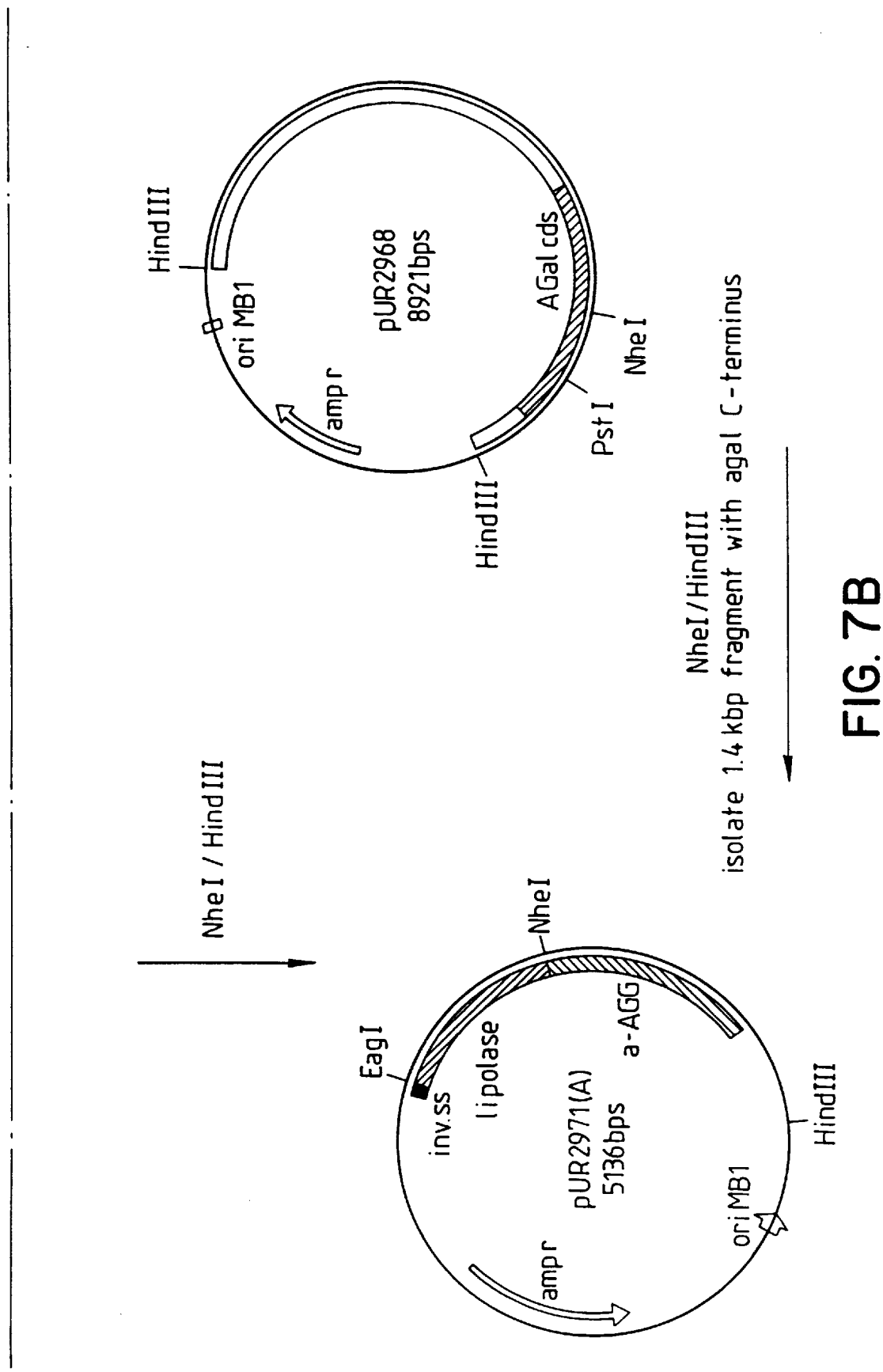
Figure 7C:
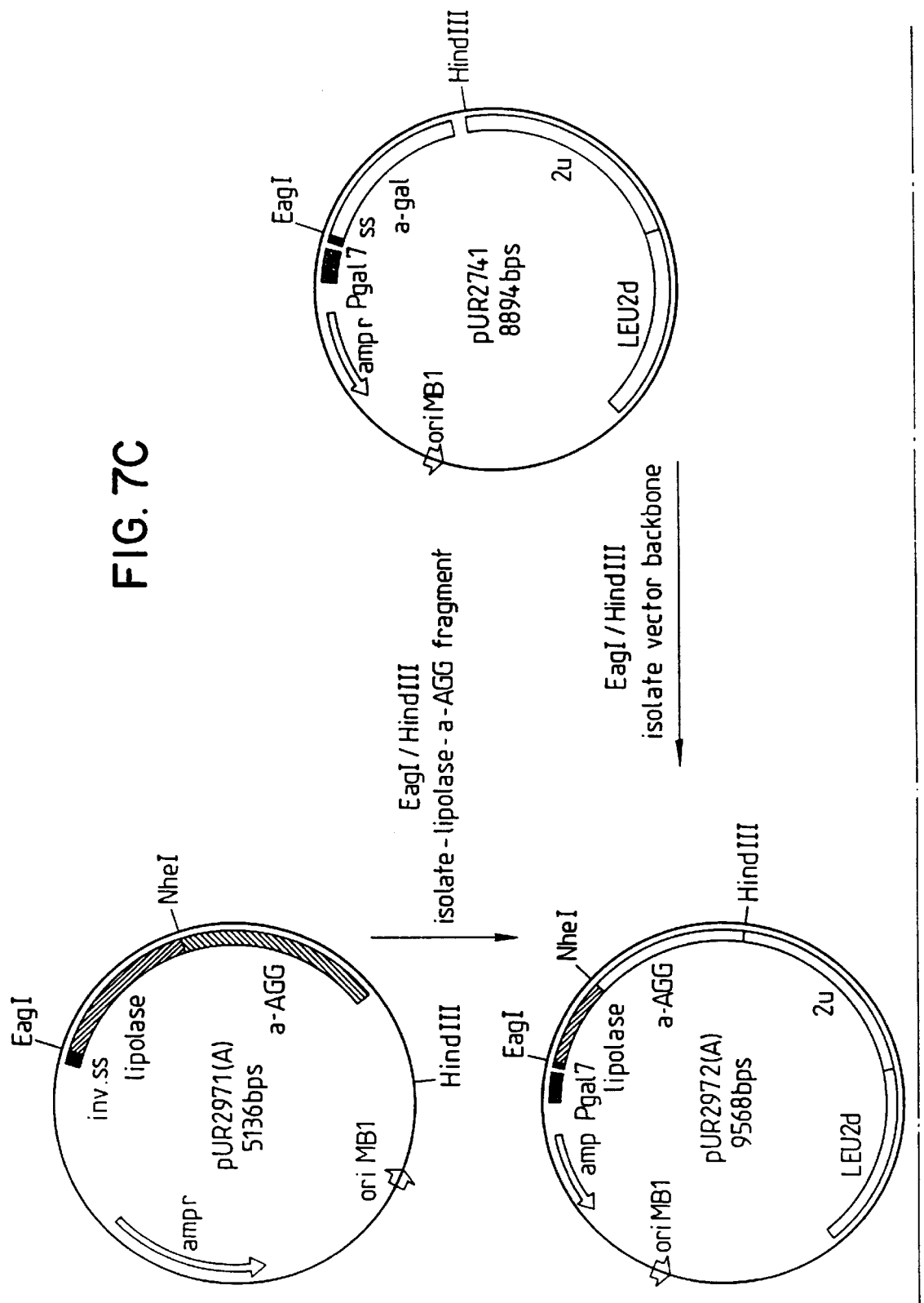
Figure 7D:
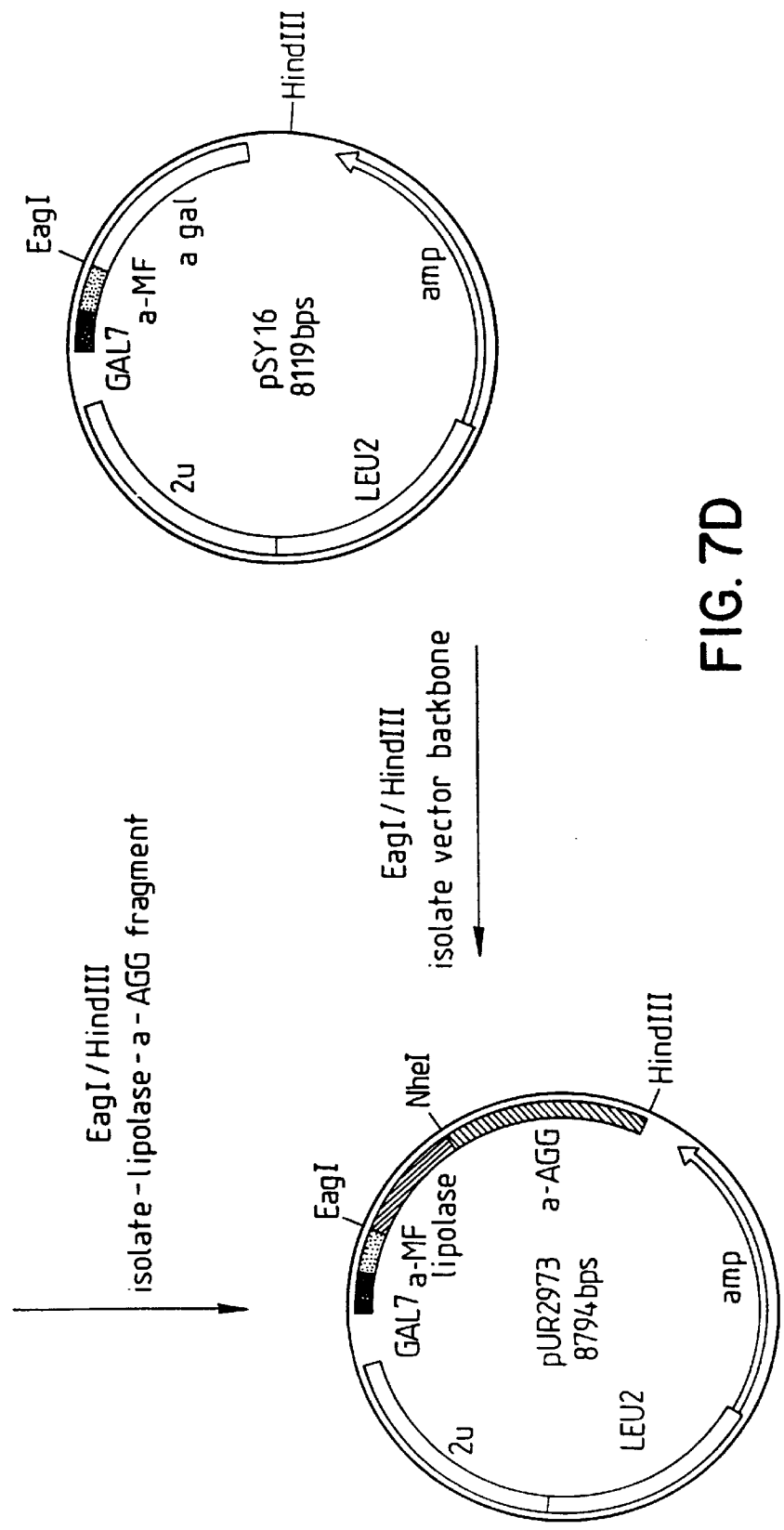

FIG. 5: Western analysis with anti α-galactosidase serum of extracellular fractions of cells of exponential phase ($OD_{530}=2$). The analyzed fractions are equivalent to 4 mg cell walls, (fresh weight):

A: MT302/1C expressing α-galactosidase,
        lane 1, growth medium
        lane 2, SDS extract of isolated cell walls
        lane 3, glucanase extract of SDS extracted cell walls;
    B: MT302/1C expressing α-Gal-AGα1 fusion protein,
        lane 1, growth medium
        lane 2, SDS extract of isolated cell walls
        lane 3, glucanase extract of SDS-extracted cell walls
        lane 4: Endo-H treated glucanase extract.

FIG. 6: Immunofluorescent labelling (anti α-galactosidase) of MT302/1C cells in the exponential phase ($OD_{530}=2$) expressing the α-Gal-α-agglutinin fusion protein.

Phase micrograph of intact cells A: overview B: detail.

FIG. 7: Schematic presentation of the construction of pUR2970A, pUR2971A, pUR2972A, and pUR2973. The restriction sites for endonucleases used are indicated in the figure. PCR oligonucleotide sequences are mentioned in the text.

Abbreviations used: AGa1 cds: coding sequence of α-agglutinin
    a-AGG=AGa1: Gene expressing α-agglutinin from *S. cerevisiae*
    amp: β-lactamase resistance gene
    lipolase: lipase gene of Humicola
    a-MF: prepro-α-mating factor sequence
    Pgal7=GAL7: GAL7 promoter
    invSS: SUC2 signal sequence
    a-gal: α-galactosidase gene
    LEU2d: truncated promoter of LEU2 gene;
    LEU2: LEU2 gene with complete promoter sequence.

FIG. 8: DNA sequence of a fragment containing the complete coding sequence of lipase B of *Geotrichum candidum* strain 335426 (see SEQ ID NO: 11). The sequence of the mature lipase B starts at nucleotide 97 of the given sequence. The coding sequence starts at nucleotide 40 (ATG).

Figure 9:
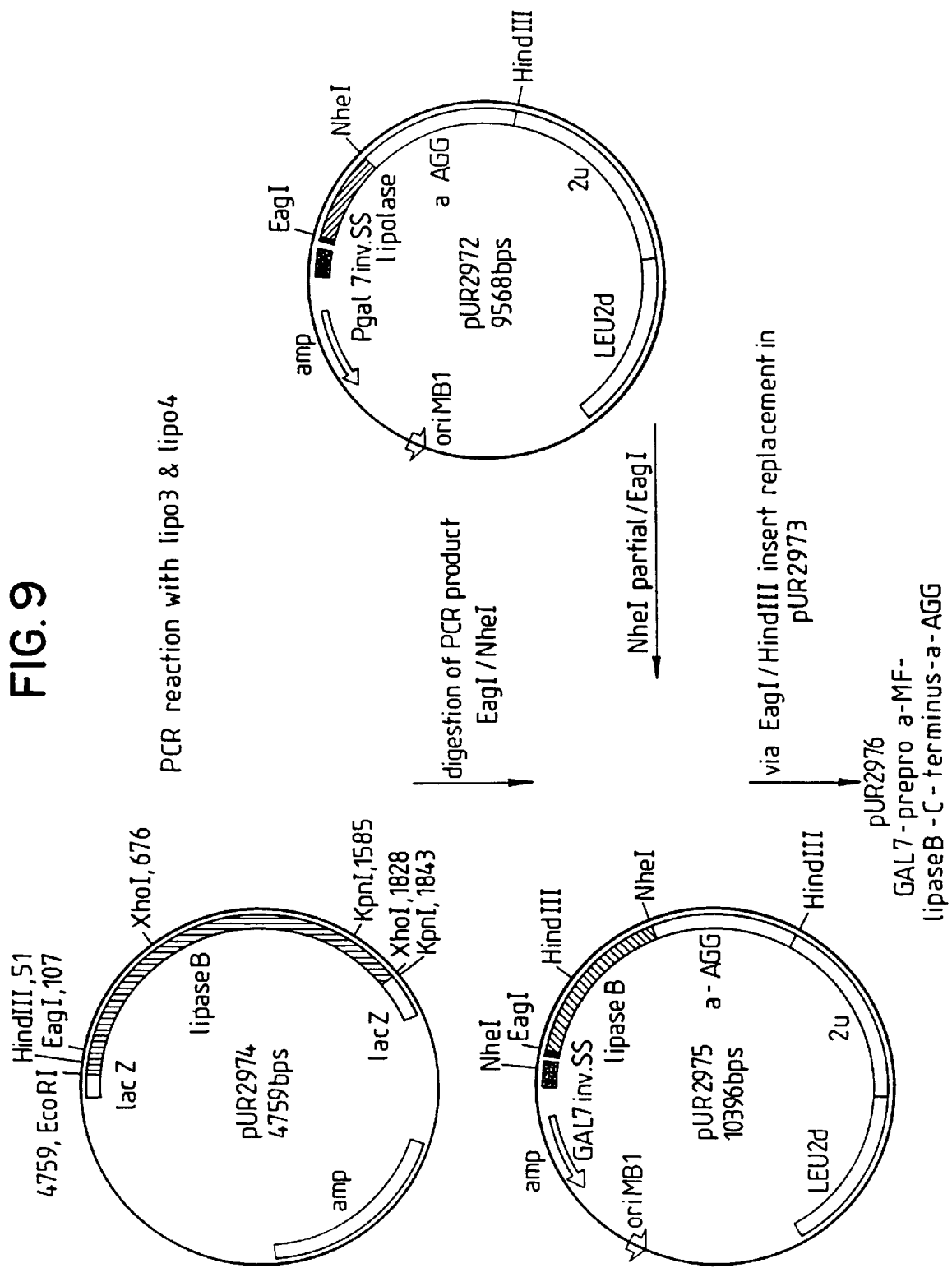

FIG. 9: Schematic presentation of the construction of pUR2975 and pUR2976. The restriction sites for endonucleases used are shown. Abbreviations used:

a-AGG: Gene expressing α-agglutinin from *S. cerevisiae*
    amp: β-lactamase resistance gene
    invSS: SUC2 signal sequence
    LEU2d: truncated promoter LEU2 gene
    Pgal7=GAL7: GAL7 promoter
    a-MF: prepro-α-mating factor sequence
    lipolase: lipase gene of Humicola
    lipaseB: lipaseB gene of *Geotrichum candidum*.

Figure 10A:
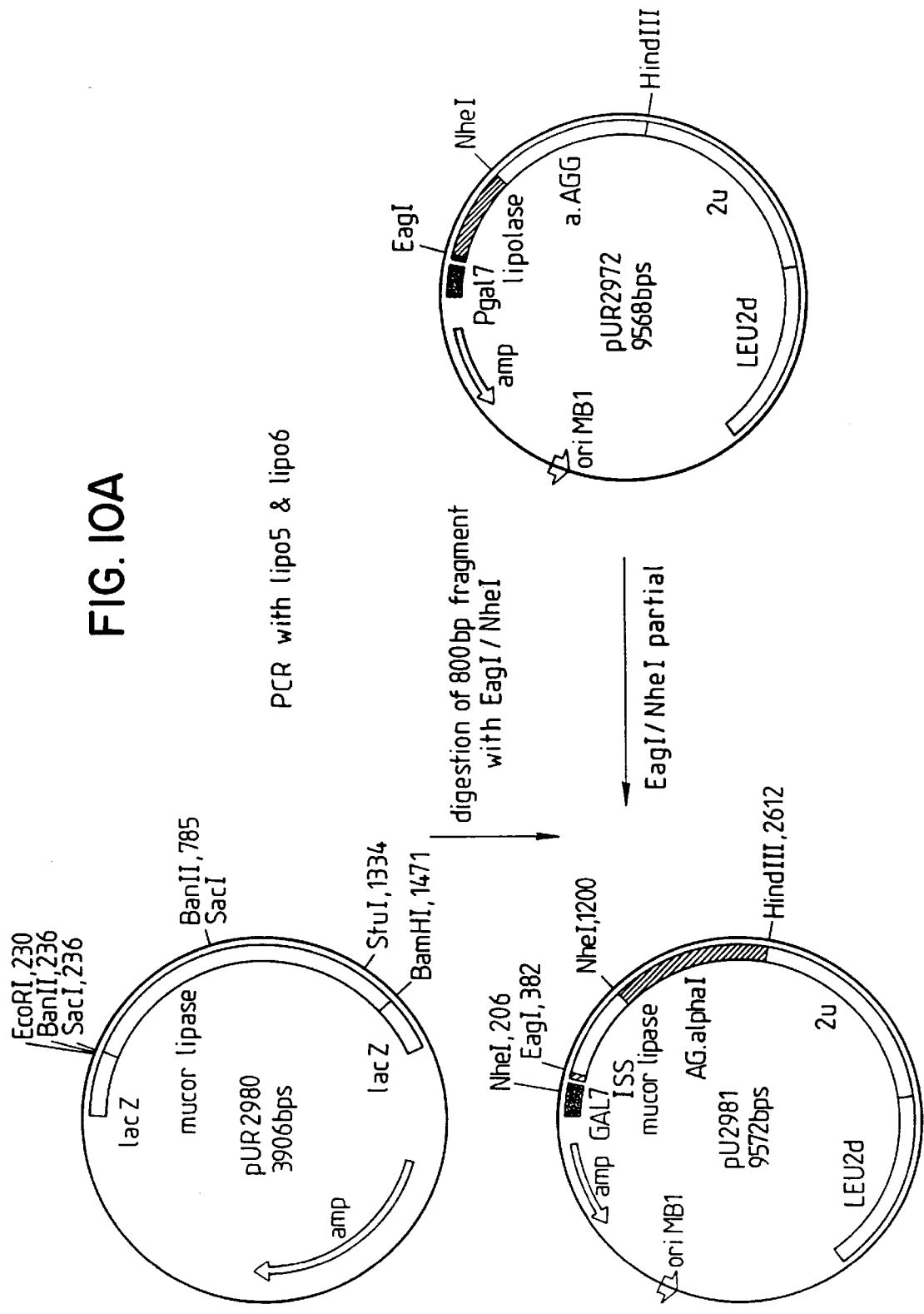
Figure 10B:
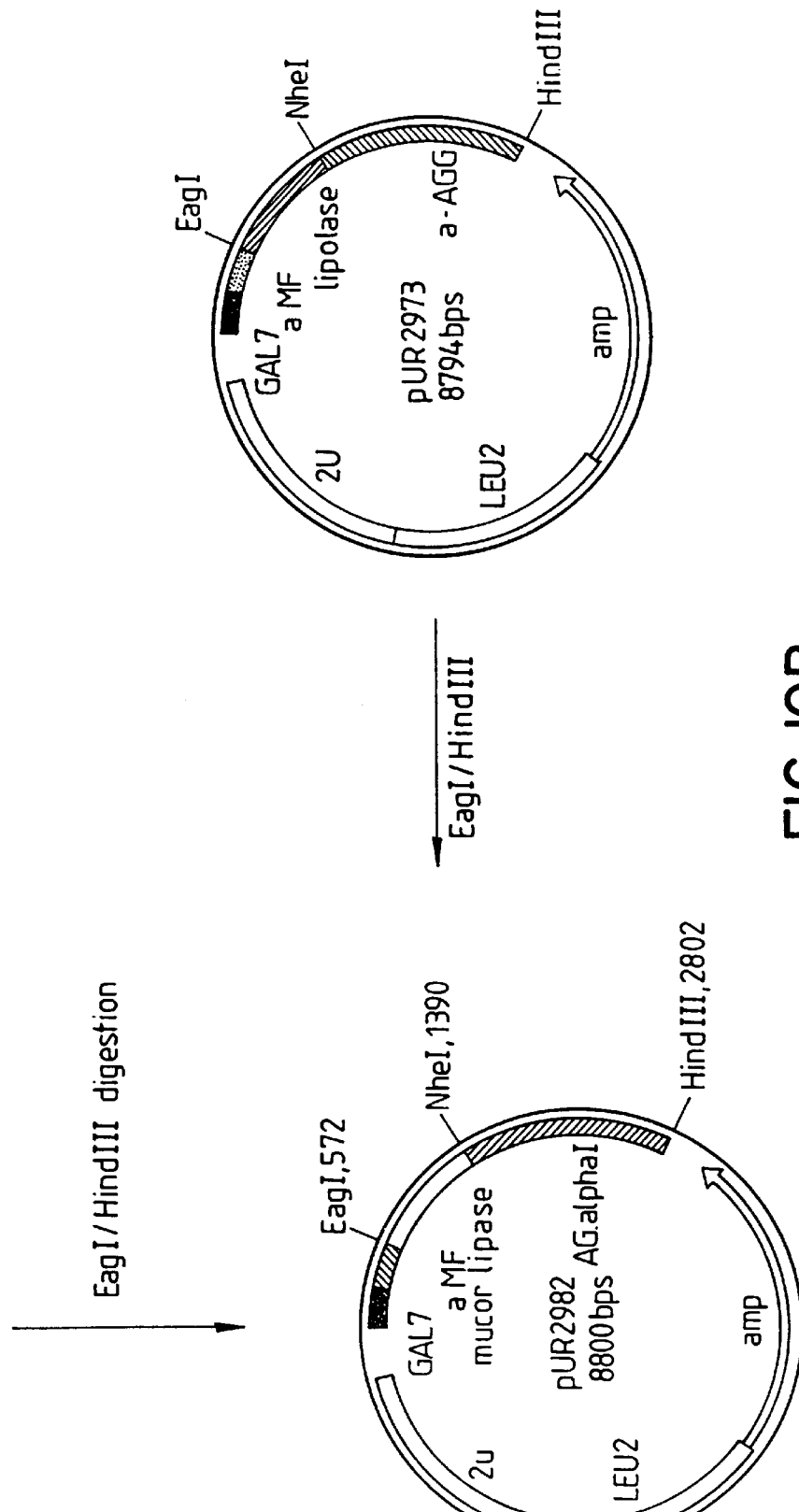

FIG. 10: Schematic presentation of the construction of pUR2981 and pUR2982. The restriction sites for endonucleases used are shown. Abbreviations used:

a-AGG=AG-alpha 1: Gene expressing α-agglutinin from *S. cerevisiae*
    mucor lipase: lipase gene of *Rhizomucor miehei*
    Pgal7=GAL7: GAL7 promoter
    a-MF: prepro-α-mating factor sequence
    amp: β-lactamase resistance gene;
    2u: 2 μm sequence
    invSS: SUC2 signal sequence
    lipolase: lipase gene of Humicola
    LEU2d: truncated promoter LEU2 gene
    LEU2: LEU2 gene with complete promoter sequence.

FIG. 11: DNA sequence (2685 bases) of the 894 amino acids coding part of the FLO1 gene (see SEQ ID NO: 21), the given sequence starts with the codon for the first amino acid and ends with the stop codon.

Figure 12:
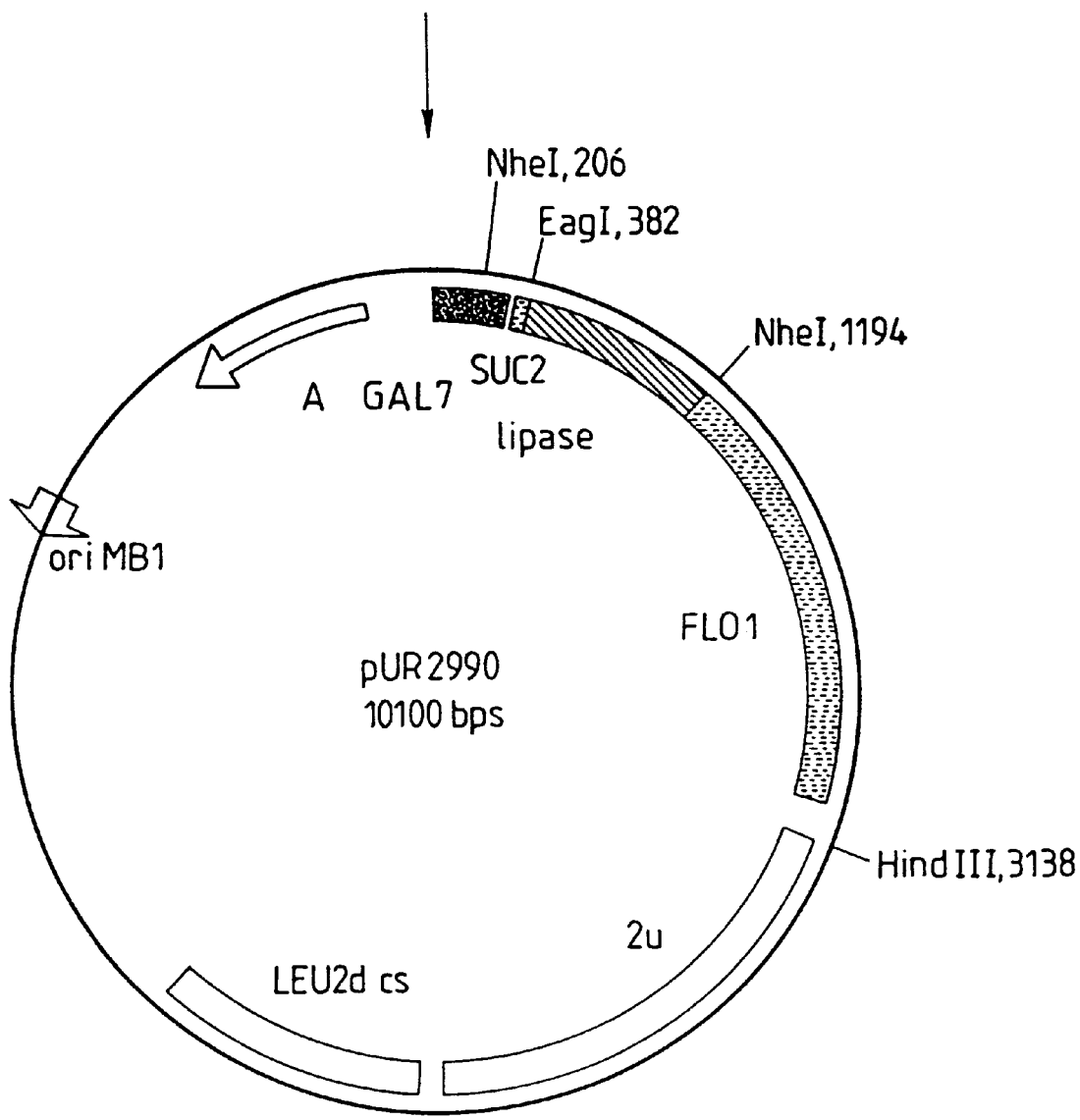

FIG. 12: Schematic presentation of plasmid pUR2990. Some restriction sites for endonucleases relevant for the given cloning procedure are shown.

Figure 13:
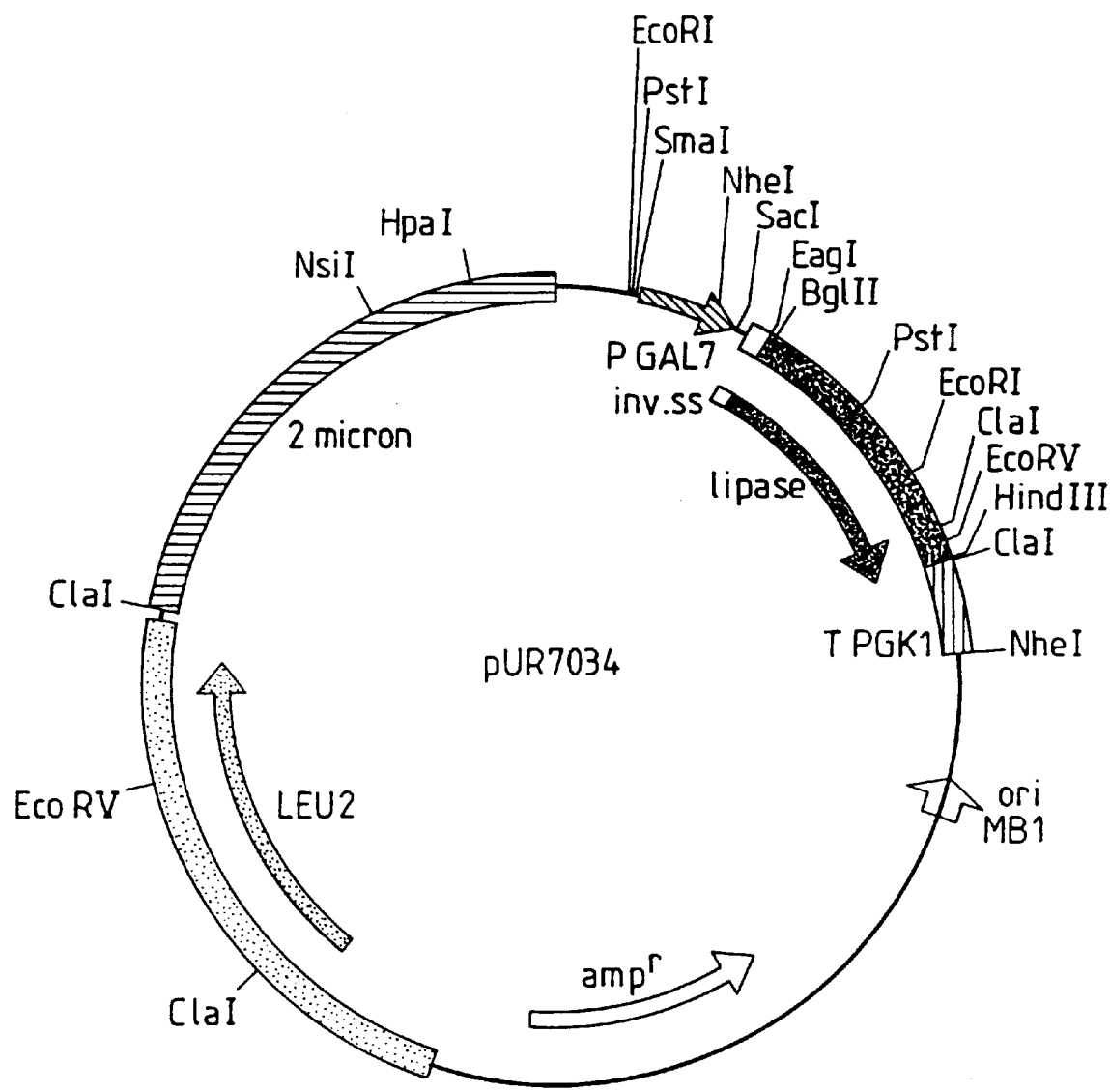

FIG. 13: Schematic presentation of plasmid pUR7034.

Figure 14:
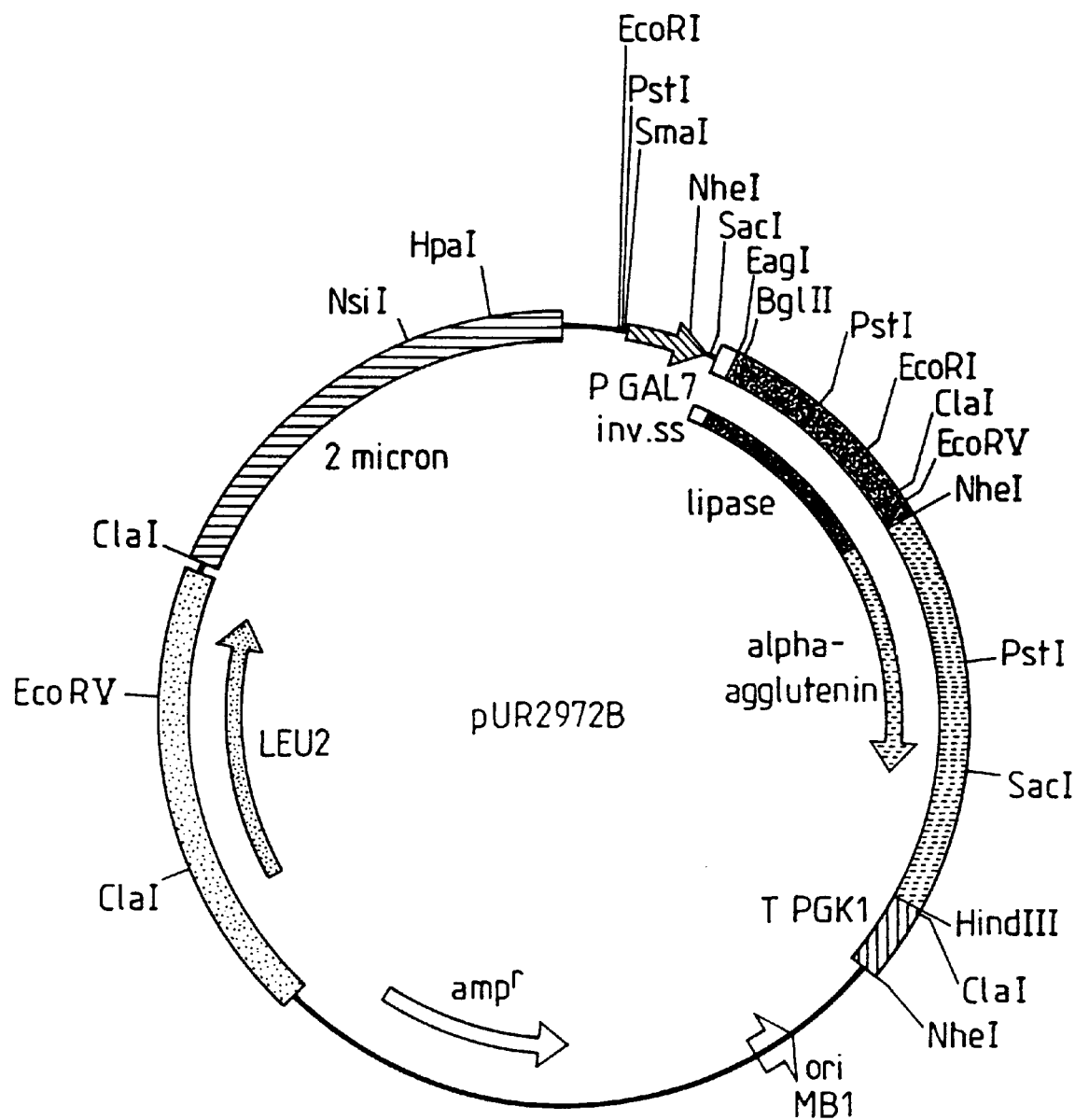

FIG. 14: Schematic presentation of plasmid pUR2972B.

Figure 15A:
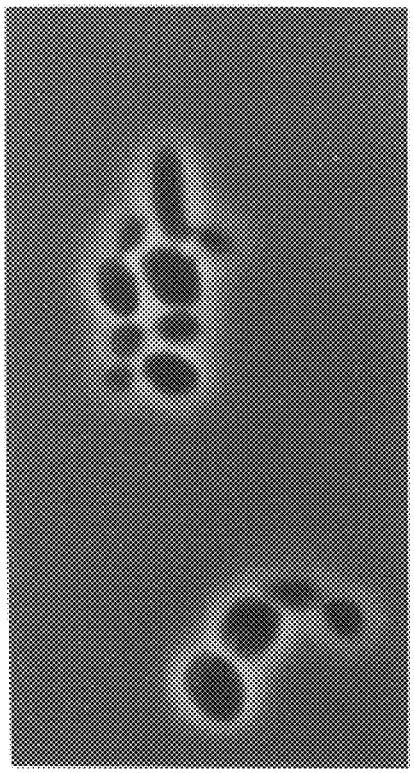
Figure 15B:
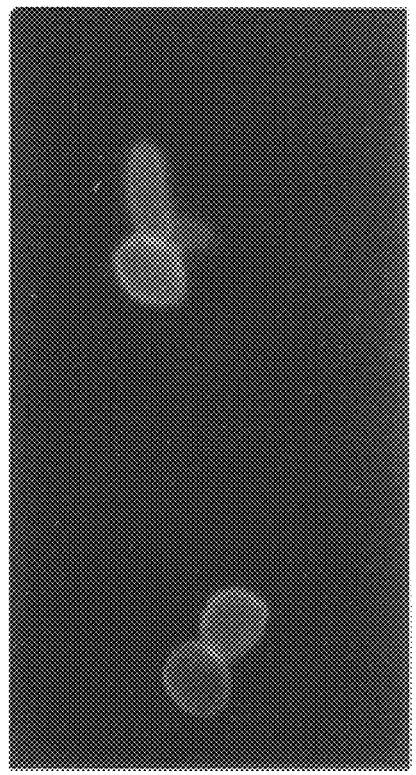

FIG. 15: Immunofluorescent labelling (anti-lipolase) of SU10 cells in the exponential phase ($OD_{530}=0.5$) expressing the lipolase/-α-agglutinin fusion protein.

A: phase micrograph B: matching fluorescent micrograph

DETAILED DESCRIPTION OF THE INVENTION

The present invention provides a method for immobilizing an enzyme, comprising immobilizing the enzyme or a functional part thereof to the cell wall of a host cell, preferably a microbial cell, using recombinant DNA techniques. In particular, the C-terminal part of a protein that ensures anchoring in the cell wall is linked to an enzyme or the functional part of an enzyme, in such a way that the enzyme is localized on or just above the cell surface. In this way immobilized enzymes are obtained on the surface of cells. The linkage is performed at gene level and is characterized in that the structural gene coding for the enzyme is coupled to at least part of a gene encoding an anchor-protein in such a way that in the expression product the enzyme is coupled at its C-terminal end to the C-terminal part of an anchor-protein. The chimeric enzyme is preferably preceded by a signal sequence that ensures efficient secretion of the chimeric protein.

Thus the invention relates to a recombinant polynucleotide comprising a structural gene encoding a protein providing catalytic activity and at least a part of a gene encoding a protein capable of anchoring in a eukaryotic or prokaryotic cell wall, said part encoding at least the C-terminal part of said anchoring protein. The length of the C-terminal part of the anchoring protein may vary. Although the entire structural protein could be used, it is preferred that only a part is used, leading to a more efficient exposure of the enzyme protein in the medium surrounding the cell. The anchoring part of the anchoring protein should preferably be entirely present. As an example, about the C-terminal half of the anchoring protein could be used. Preferably, the polynucleotide further comprises a sequence encoding a signal peptide ensuring secretion of the expression product of the polynucleotide. The signal peptide can be derived from a GPI anchoring protein, α-factor, α-agglutinin, invertase or inulinase, α-amylase of Bacillus, or a proteinase of lactic acid bacteria. The protein capable of anchoring in the cell wall is preferably selected form the group of α-agglutinin, AGA1, FLO1 (flocculation protein) or the Major Cell Wall Protein of lower eukaryotes, or a proteinase of lactic acid bacteria. The polynucleotide of the invention is preferably operably linked to a promoter, preferably a regulatable promoter, especially an inducible promoter.

The invention also relates to a recombinant vector containing the polynucleotide as described above, and to a host cell containing this polynucleotide, or this vector. In a particular case, wherein the protein providing catalytic activity exhibits said catalytic activity when present in a multimeric form, such as may be the case with oxidoreductases, dimerisation or multimerisation of the monomers might be a prerequisite for activity. The vector and/or the host cell can then further comprise a second polynucleotide comprising a structural gene encoding the same protein providing catalytic activity combined with a sequence encoding a signal peptide ensuring secretion of the expression product of said second polynucleotide, said second polynucleotide being operably linked to a regulatable promoter, preferably an inducible or repressible promoter. Expression and secretion of the second polynucleotide after expression and secretion of the first polynucleotide will then result in the formation of an active multimer on the exterior of the cell wall. The host cell or microorganism preferably contains the polynucleotide described above, or at least one of said polynucleotides in the case of a combination, integrated in its chromosome.

The present invention relates in particular to lower eukaryotes like yeasts that have very stable cell walls and have proteins that are known to be anchored in the cell wall, e.g. α-agglutinin or the product of gene FLO1. Suitable yeasts belong to the genera Candida, Debaryomyces, Hansenula, Kluyveromyces, Pichia and Saccharomyces. Also fungi, especially Aspergillus, Penicillium and Rhizopus can be used. For certain applications also prokaryotes are applicable.

For yeasts the present invention deals in particular with genes encoding chimeric enzymes consisting of:
a. the signal sequence e.g. derived from the α-factor-, the invertase-, the α-agglutinin- or the inulinase genes;
b. structural genes encoding hydrolytic enzymes such as α-galactosidase, proteases, peptidases, pectinases, pectylesterase, rhamnogalacturonase, esterases and lipases, or non-hydrolytic enzymes such as oxidases; and
c. the C-terminus of typically cell wall bound proteins such as α-agglutinin (see reference 4), AGA1 (see reference 5) and FLO1 (see the non-prior published reference 6).

The expression of these genes can be under the control of a constitutive promoter, but more preferred are regulatable, i.e. repressible or inducible promoters such as the GAL7 promoter for Saccharomyces, or the inulinase promoter for Kluyveromyces or the methanol-oxidase promoter for Hansenula.

Preferably the constructs are made in such a way that the new genetic information is integrated in a stable way in the chromosome of the host cell.

The invention further relates to a host cell, in particular a microorganism, having the chimeric protein described above immobilized on its cell wall. It further concerns the use of such microorganisms for carrying out an enzymatic process by contacting a substrate for the enzyme with the microorganism. Such a process may be carried out e.g. in a packed column, wherein the microorganisms may be supported on solid particles, or in a stirred reactor. The reaction may be aqueous or non-aqueous. Where necessary, additives necessary for the performance of the enzyme, e.g. a co-factor, may be introduced in the reaction medium.

After repeated usage of the naturally immobilized enzyme system in processes, the performance of the system may decrease. This is caused either by physical denaturation or by chemical poisoning or detachment of the enzyme. A particular feature of the present invention is that after usage the system can be recovered from the reaction medium by simple centrifugation or membrane filtration techniques and that the thus collected cells can be transferred to a recovery medium in which the cells revive quickly and concomitantly produce the chimeric protein, thus ensuring that the surface of the cells will be covered by fully active immobilized enzyme. This regeneration process is simple and cheap and therefore will improve the economics of enzymic processes and may result in a much wider application of processes based on immobilized enzyme systems.

However, by no means the present invention is restricted to the reusability of the immobilized enzymes.

The invention will be illustrated by the following examples without the scope of the invention being limited thereto.

EXAMPLE 1

Immobilized α-Galactosidase/α-Agglutinin on the Surface of S. cerevisiase.

The gene encoding α-agglutinin has been described by Lipke et al. (see reference 4). The sequence of a 6057 bp HindIII insert in pTZ18R, containing the whole AGα1 gene is given in FIG. 1. The coding sequence expands over 650 amino acids, including a putative signal sequence starting at nucleotide 3653 with ATG. The unique NheI site cuts the DNA at position 988 of the given coding sequence within the coding part of amino acid 330, thereby separating the α-agglutinin into an N-terminal and a C-terminal part of about same size.

Figure 2:
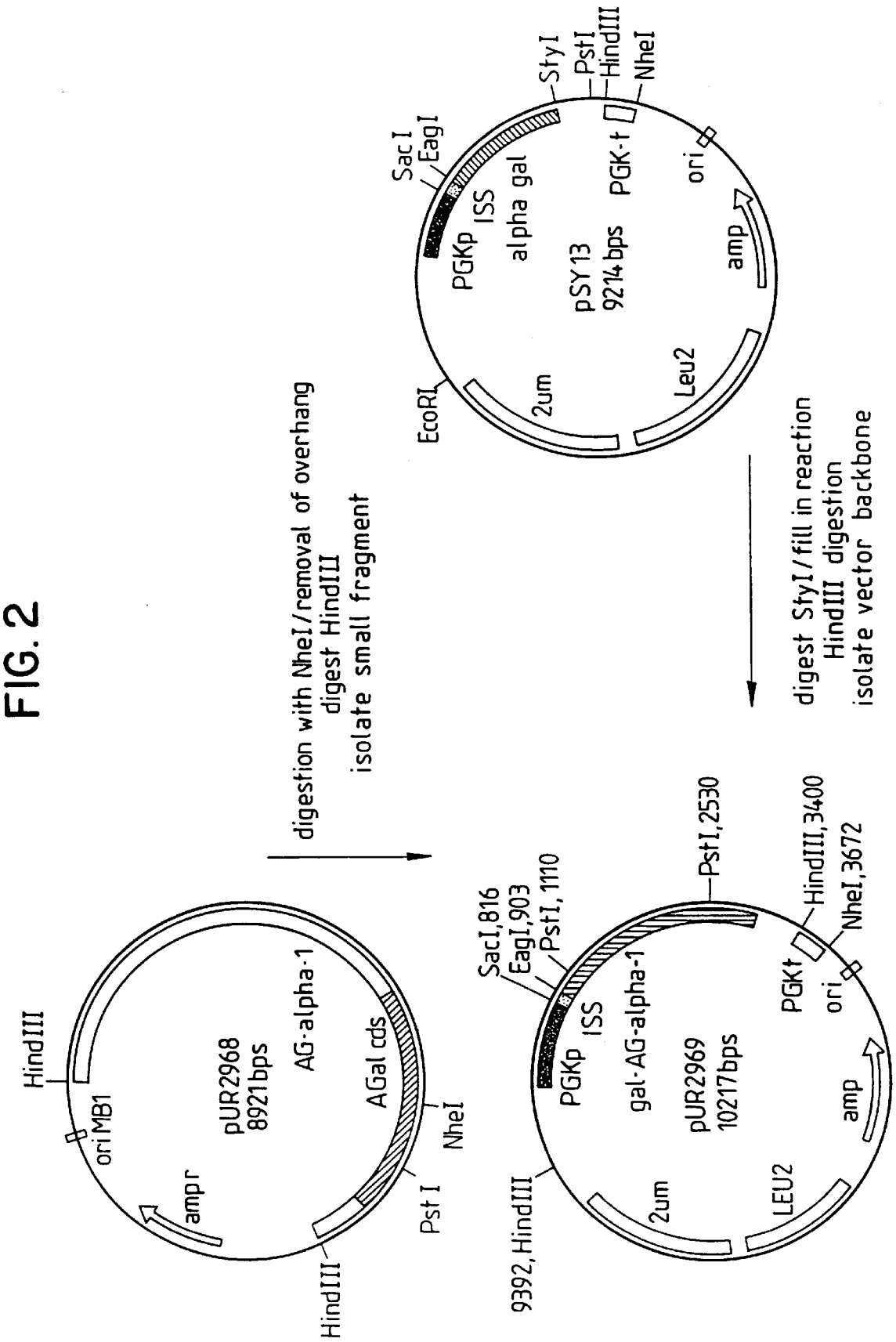
FIG. 2: Schematic presentation of the construction of pUR2969. The restriction sites for endonucleases used are shown. Abbreviations used: AG-alpha-1: Gene expressing α-agglutinin from *S. cerevisiae* amp: β-lactamase resistance gene
    PGKp: phosphoglyceratekinase promoter
    PGKt: terminator of the same gene.

Through digestion of pUR2968 (see FIG. 2) with NheI/HindIII a 1.4 kb fragment was released, containing the sequence information of the putative cell wall anchor. For the fusion to α-galactosidase the plasmid pSY16 was used, an episomal vector based on YEplac 181, harboring the α-galactosidase sequence preceded by the SUC2 invertase signal sequence and placed between the constitutive PGK promoter and PGK terminator. The StyI site, present in the last nine base-pairs of the open reading frame of the α-galactosidase gene, was ligated to the NheI site of the AGα1 gene fragment. To ensure the in frame fusion, the StyI site was filled in and the 5' overhang of the NheI site was removed, prior to ligation into the StyI/HindIII digested pSY13 (see FIG. 2).

To verify the correct assembly of the new plasmid, the shuttle vector was transformed into E. coli JM109 (recA1 supE44 endA1 hsdR17 gyrA96 relA1 thi ▲(lac-proAB) F' [traD36 proAB⁺ lacI$^q$ lacZ▲M15]) (see reference 7) by the transformation protocol described by Chung et al. (see reference 8). One of the positive clones, designated pUR2969, was further characterized, the DNA isolated and purified according to the Quiagen protocol and subsequently characterized by DNA sequencing. DNA sequencing was mainly performed as described by Sanger et al. (see reference 9), and Hsiao (see reference 10), here with the Sequenase version 2.0 kit from United States Biochemical Company, according to the protocol with T7 DNA polymerase (Amersham International plc) and [$^{35}$S]dATPαS (Amersham International plc: 370 MBq/ml; 22 TBq/mmol).

This plasmid was then transformed into S. cerevisiae strain MT302/1C according to the protocol from Klebe et al. (see reference 11).

Yeast transformants were selected on selective plates, lacking leucine, on with 40 μl (20 mg/ml DMF). X-α-Gal (5-bromo-4-chloro-3-indolyl-α-D-glucose, Boehringer Mannheim) was spread, to directly test for α-galactosidase activity (see reference 12). To demonstrate the expression, secretion, localization and activity of the chimeric protein the following analyses were performed:

1. Expression and Secretion

S. cerevisiae strain MT302/1C was transformed with either plasmid pSY13 containing the α-galactosidase gene of Cyamopsis tetragonoloba or plasmid pUR2969 containing the α-galactosidase/α-agglutinin fusion construct. During batch culture α-galactosidase activities were determined for washed cells and growth medium. The results are given in FIG. 3 and FIG. 4. The α-galactosidase expressed from yeast cells containing plasmid pSY13 was almost exclusively present in the growth medium (FIG. 3A), whereas the α-galactosidase-α-agglutinin fusion protein was almost exclusively cell associated (FIG. 4A). Moreover, the immobilized, cell wall-associated, α-galactosidase-α-agglutinin fusion enzyme had retained the complete activity over the whole incubation time, while the secreted and released enzyme lost about 90% of the activity after an incubation of 65 hours. This indicates, that the immobilization of the described enzyme into the cell wall of yeast protects the enzyme against inactivation, presumably through proteinases, and thereby increases the stability significantly. Further insight into the localization of the different gene products was obtained by Western analysis. Therefore, cells were harvested by centrifugation and washed in 10 mM Tris.HCl, pH 7.8; 1 mM PMSF at 0° C. and all subsequent steps were performed at the same temperature. Three ml isolation buffer and 10 g of glass beads were added per gram of cells (wet weight). The mixture was shaken in a Griffin shaker at 50% of its maximum speed for 30 minutes. The supernatant was isolated and the glass beads were washed with 1M NaCl and 1 mM PMSF until the washes were clear. The supernatant and the washes were pooled. The cell walls were recovered by centrifugation and were subsequently washed in 1 mM PMSF.

Non-covalently bound proteins or proteins bound through disulphide bridges were released from cell walls by boiling for 5 minutes in 50 mM Tris.HCl, pH 7.8; containing 2% SDS, 100 mM EDTA and 40 mM β-mercaptoethanol. The SDS-extracted cell walls were washed several times in 1 mM PMSF to remove SDS. Ten mg of cell walls (wet weight) were taken up in 20 l 100 mM sodium acetate, pH 5.0, containing 1 mM PMSF. To this, 0.5 mU of the β-1,3-glucanase (Laminarase; Sigma L5144) was used as a source of β-1,3-glucanase) was added followed by incubation for 2 hours at 37° C. Subsequently another 0.5 mU of β-1,3-glucanase was added, followed by incubation for another 2 hours at 37° C.

Proteins were denatured by boiling for 5 minutes preceding Endo-H treatment. Two mg of protein were incubated in 1 ml 50 mM potassium phosphate, pH 5.5, containing 100 mM β-mercaptoethanol and 0.5 mM PMSF with 40 mU Endo-H (Boehringer) for 48 hours at 37° C. Subsequently 20 mU Endo-H were added followed by 24 hours of incubation at 37° C.

Proteins were separated by SDS-PAGE according to Laemmli (see reference 13) in 2.2.–20% gradient gels. The gels were blotted by electrophoretic transfer onto Immobilon polyvinylidene-difluoride membrane (Millipore) as described by Towbin et al. (see reference 14). In case of highly glycosylated proteins a subsequently mild periodate treatment was performed in 50 mM periodic acid, 100 mM sodium acetate, pH 4.5, for several hours at 4° C. All subsequent incubations were carried out at room temperature. The blot was blocked in PBS, containing 0.5% gelatine and 0.5% Tween-20, for one hour followed by incubation for 1 hour in probe buffer (PBS, 0.2% gelatine, 0.1% Tween-20) containing 1:200 diluted serum. The blot was subsequently washed several times in washing buffer (PBS; 0.2% gelatine; 0.5% Tween-20) followed by incubation for 1 hour in probe-buffer containing $^{125}$I-labelled protein A (Amersham). After several washes in washing buffer, the blot was air-dried, wrapped in Saran (Dow) and exposed to X-omat S film (Kodak) with intensifying screen at −70° C. An Omnimedia 6cx scanner and the Adobe Photoshop programme were used to quantify the amount of labelled protein. The results of the various protein isolation procedures from both transformants are given in FIG. 5. While for the transformants comprising the pSY13 plasmid the overall mass of the enzyme was localized in the medium, with only minor amounts of enzyme more entrapped than bond in the cell wall (FIG. 5A)—which could completely be removed by SDS extraction—the fusion protein was tightly bound to the cell wall; with only small amounts of α-galactosidase/α-agglutinin delivered into the surrounding culture fluid or being SDS extractable. In contrast to the laminarinase extraction of cell walls from cells expressing the free α-galactosidase, where no further liberation of any more enzyme was observed, identical treatment of fusion enzyme expressing cells released the overall bulk of the enzyme. This indicates that the fusion protein is intimately associated with the cell wall glucan in S. cerevisiae, like α-agglutinin, while α-galactosidase alone is not. The subsequently performed EndoH treatment showed a heavy glycosylation of the fusion protein, a result, entirely in agreement with the described extended glycosylation of the C-terminal part of α-agglutinin.

2. Localization

Immunofluorescent labelling with anti-α-galactosidase serum was performed on intact cells to determine the presence and distribution of α-galactosidase/α-agglutinin fusion protein in the cell wall. Immunofluorescent labelling was carried out without fixing according to Watzele et al. (see reference 15). Cells of OD$_{530}$=2 were isolated and washed in TBS (10 mM Tris.HCl, pH 7.8, containing 140 mM NaCl, 5 mM EDTA and 20 μg/ml cycloheximide). The cells were incubated in TBS+anti-α-galactosidase serum for 1 hour, followed by several washings in TBS. A subsequent incubation was carried out with FITC-conjugated anti-rabbit IgG (Sigma) for 30 minutes. After washing in TBS, cells were taken up in 10 mM Tris.HCl, pH 9.0, containing 1 mg/ml p-phenylenediamine and 0.1% azide and were photographed on a Zeiss 68000 microscope. The results of these analysis are given in FIG. 6, showing clearly that the chimeric α-galactosidase/α-agglutinin is localized at the surface of the yeast cell. Buds of various sizes, even very small ones very uniformly labelled, demonstrates that the fusion enzyme is continuously incorporated into the cell wall throughout the cell cycle and that it instantly becomes tightly linked.

3. Activity

To quantitatively assay α-galactosidase activity, 200 μl samples containing 0.1M sodium-acetate, pH 4.5 and 10 mM p-nitrophenyl-α-D-galactopyranoside (Sigma) were incubated at 37° C. for exactly 5 minutes. The reaction was stopped by addition of 1 ml 2% sodium carbonate. From intact cells and cell walls, removed by centrifugation and isolated and washed as described, the α-galactosidase activity was calculated using the extinction coefficient of p-nitrophenol of 18.4 $cm^2/\mu mole$ at 410 nm. One unit was defined as the hydrolysis of 1 μmole substrate per minute at 37° C.

TABLE 1

Distribution of free and immobilized α-galactosidase activity in yeast cells

| Expressed protein | α-Galactosidase activity (U/g F.W. cells) | | |
|---|---|---|---|
| | Growth medium | Intact cells | Isolated cell walls |
| α-galactosidase | 14.7 | 0.37 | 0.01 |
| αGal/αAGG fusion protein | 0.54 | 13.3 | 10.9 |

Transformed MT302/1C cells were in exponential phase ($OD_{530}$ = 2). One unit is defined as the hydrolysis of 1 μmole of p-nitrophenyl-α-D-galactopyranoside per minute at 37° C.

The results are summarized in Table 1. While the overall majority of α-galactosidase was distributed in the culture fluid, most of the fusion product was associated with the cells, primarily with the cell wall. Taking together the results shown in FIGS. 3 to 6 and in Table 1, it could be calculated that the enzymatic α-galactosidase activity of the chimeric enzyme is as good as that of the free enzyme. Moreover, during stationary phase, the activity of the α-galactosidase in the growth medium decreased, whereas the activity of the cell wall associated α-galactosidase α-agglutinin fusion remained constant, indicating that the cell associated fusion protein is protected from inactivation or proteolytic degradation.

N.B. The essence of this EXAMPLE was published during the priority year by M. P. Schreuder et al. (see reference 25).

EXAMPLE 2A

Immobilized Humicola Lipase/α-Agglutinin on the Surface of *S. cerevisiae*. (inducible expression of immobilized enzyme system)

The construction and isolation of the 1.4 kb NheI/HindIII fragment containing the C-terminal part of α-agglutinin has been described in EXAMPLE 1. Plasmid pUR7021 contains an 894 bp long synthetically produced DNA fragment encoding the lipase of Humicola (see reference 16 and SEQ ID NO: 7 and 8), cloned into the EcoRI/HindIII restriction sites of the commercially available vector pTZ18R (see FIG. 7). For the proper one-step modification of both the 5' end and the 3' end of the DNA part coding for the mature lipase, the PCR technique can be applied. Therefore the DNA oligonucleotides lipo1 (see SEQ ID NO: 3) and lipo2 (see SEQ ID NO: 6) can be used as primers in a standard PCR protocol, generating an 826 bp long DNA fragment with an EagI and a HindIII restriction site at the ends, which can be combined with the larger part of the EagI/HindIII digested pUR2650, a plasmid containing the α-galactosidase gene preceded by the invertase signal sequence as described earlier in this specification, thereby generating plasmid pUR2970A (see FIG. 7).

PCR oligonucleotides for the in-frame linkage of Humicola lipase and the C-terminus of α agglutinin.

a: PCR oligonucleotides for the transition between SUC2 signal sequence and the N-terminus of lipase.

```
                                    >mature lipase
                         EagI    E   V   S   Q   D   L   F
primer lipo1: 5'-GGG GCG GCC GAG GTC TCG CAA GAT CTG GA-3'
                         ||| ||| ||| ||| ||| ||| ||
lipase:       3'-TAA GCA GCT CTC CAG AGC GTT CTG GAC CTG TTT-5'
(non-coding strand, see SEQ ID NO: 4)
``` b: PCR oligonucleotides for the in frame transition between C-terminus of lipase and C-terminal part of α-agglutinin.

```
                           F   G   L   I   G   T   C   L
lipase         5'-TTC GGG TTA ATT GGG ACA TGT CTT TAG TGC GA-3'
(cod. strand)     ||| ||| ||| ||| ||| ||| ||| ||| ||
primer         3'-CCC AAT TAA CCC TGT ACA GAA CGA TCG GAA TTC GAACCCC-5'
lipo2:                                         NheI        HindIII
(for the part of the lipase coding strand see SEQ ID NO: 5)
```

Through the PCR method a NheI site will be created at the end of the coding sequence of the lipase, allowing the in-frame linkage between the DNA coding for lipase and the DNA coding for the C-terminal part of α-agglutinin. Plasmid pUR2970A can then be digested with NheI and HindIII and the 1.4 kb NheI/HindIII fragment containing the C-terminal part of α-agglutinin from plasmid pUR2968 can be combined with the larger part of NheI and HindIII treated plasmid pUR2970A, resulting in plasmid pUR2971A. From this plasmid the 2.2 kb EagI/HindIII fragment can be isolated and ligated into the EagI- and HindIII-treated pUR2741, whereby plasmid pUR2741 is a derivative of pUR2740 (see reference 17), where the second EagI restriction site in the already inactive Tet resistance gene was deleted through NruI/SalI digestion. The SalI site was filled in prior to religation. The ligation then results in pUR2972A containing the GAL7 promoter, the invertase signal sequence, the chimeric lipase/α-agglutinin gene, the 2 μm sequence, the defective Leu2 promoter and the Leu2 gene. This plasmid can be used for transforming S. cerevisiae and the transformed cells can be cultivated in YP medium containing galactose as an inducer without repressing amounts of glucose being present, which causes the expression of the chimeric lipase/α-agglutinin gene.

The expression, secretion, localization and activity of the chimeric lipase/α-agglutinin can be analyzed using similar procedures as given in EXAMPLE 1.

In a similar way variants of Humicola lipase, obtained via rDNA techniques, can be linked to the C-terminal part of α-agglutinin, which variants can have a higher stability during (inter)esterification processes.

EXAMPLE 2B

Immobilized Humicola Lipase/α-Agglutinin on the Surface of *S. cerevisiase* (inducible expression of immobilized enzyme system)

EXAMPLE 2A describes a protocol for preparing a particular construct. Before carrying out the work it was considered more convenient to use the expression vector described in EXAMPLE 1, so that the construction route given in this EXAMPLE 2B differs on minor points from the construction route given in EXAMPLE 2A and the resulting plasmids are not identical to those described in EXAMPLE 2A. However, the essential gene construct comprising the promoter, signal sequence, and the structural gene encoding the fusion protein are the same in EXAMPLES 2A and 2B.

1. Construction

The construction and isolation of the 1.4 kb NheI/HindIII fragment encoding the C-terminal part of α-agglutinin cell wall protein has been described in EXAMPLE 1. The plasmid pUR7033 (resembling pUR7021 of EXAMPLE 2A) was made by treating the commercially available vector pTZ18R with EcoRI and HindIII and ligating the resulting vector fragment with an 894 bp long synthetically produced DNA EcoRI/HindIII fragment encoding the lipase of Humicola (see SEQ ID NO: 7 and 8, and reference 16).

For the fusion of the lipase to the C-terminal, cell wall anchor-comprising domain of α-agglutinin, plasmid pUR7033 was digested with EagI and HindIII, and the lipase coding sequence was isolated and ligated into the EagI- and HindIII-digested yeast expression vector pSY1 (see reference 27), thereby generating pUR7034 (see FIG. 13). This is a 2 μm episomal expression vector, containing the α-galactosidase gene described in EXAMPLE 1, preceded by the invertase (SUC2) signal sequence under the control of the inducible GAL7 promoter.

Parallel to this digestion, pUR7033 was also digested with EcoRV and HindIII, thereby releasing a 57 bp long DNA fragment, possessing codons for the last 15 carboxyterminal amino acids. This fragment was exchanged against a small DNA fragment, generated through the hybridisation of the two chemically synthesized deoxyoligonucleotides SEQ ID NO: 9 and SEQ ID NO: 10. After annealing of both DNA strands, these two oligonucleotides essentially reconstruct the rest of the 3' coding sequence of the initial lipase gene, but additionally introduce downstream of the lipase gene a new NheI restriction site, followed by a HindIII site in close vicinity, whereby the first three nucleotides of the NheI site form the codon for the last amino acid of the lipase. The resulting plasmid was designated pUR2970B. Subsequently, this construction intermediate was digested with EagI and NheI, the lipase encoding fragment was isolated, and, together with the 1.4 kb NheI/HindIII fragment of pUR2968 ligated into the EagI- and HindIII-cut pSY1 vector. The outcome of this 3-point-ligation was called pUR2972B (see FIG. 14), the final lipolase-α-agglutinin yeast expression vector.

This plasmid was used for transforming *S. cerevisiae* strain SU10 as described in reference 17 and the transformed cells were cultivated in YP medium containing galactose as the inducer without repressing amounts of glucose being present, which causes the expression of the chimeric lipase/α-agglutinin gene.

2. Activity

To quantify the lipase activity, two activity measurements with two separate substrates were performed. In both cases, SU10 yeast cells transformed with either plasmid pUR7034 or pSY1 served as control. Therefore, yeast cell transformants containing either plasmid pSY1 or plasmid pUR7034 or plasmid pUR2972B were grown up for 24 h in YNB-glucose medium supplied with histidine and uracil, then diluted 1:10 in YP-medium supplied with 5% galactose, and again cultured. After 24 h incubation at 30° C., a first measurement for both assays was performed.

The first assay applied was the pH stat method. Within this assay, one unit of lipase activity is defined as the amount of enzyme capable of liberating one micromole of fatty acid per minute from a triglyceride substrate under standard assay conditions (30 ml assay solution containing 38 mM olive oil, considered as pure trioleate, emulsified with 1:1 w/w gum arabic, 20 mM calcium chloride, 40 mM sodium chloride, 5 mM Tris, pH 9.0, 30° C.) in a radiometer pH stat apparatus (pHM 84 pH meter, ABU 80 autoburette, TTA 60 titration assembly). The fatty acids formed were titrated with 0.05N NaOH and the activity measured was based on alkali consumption in the interval between 1 and 2 minutes after addition of putative enzyme batch. To test for immobilized lipase activity, 1 ml of each culture was centrifuged, the supernatant was saved, the pellet was resuspended and washed in 1 ml 1M sorbitol, subsequently again centrifuged and resuspended in 200 μl 1M sorbitol. From each type of yeast cell the first supernatant and the washed cells were tested for lipase activity.

A: Lipase activity after 24 h (LU/ml)

|  | cell bound | culture fluid |
| --- | --- | --- |
| pSY1 | 5.9 | 8.8 |
| pUR7034 | 24.1 | 632.0 |
| pUR2972B-(1) | 18.7 | 59.6 |
| pUR2972B-(2) | 24.6 | 40.5 |

B: Lipase activity after 48 h (LU/ml)

|  | cell bound | culture fluid | OD660 |
|---|---|---|---|
| pSY1 | 6.4 | 4.3 | ⁻40 |
| pUR7034 | 215.0 | 2750.0 | ⁻40 |
| pUR2972B-(1) | 37.0 | 87.0 | ⁻40 |
| pUR2972B-(2) | 34.0 | 82.0 | ⁻40 |

The rest of the yeast cultures was further incubated, and essentially the same separation procedure was done after 48 hours. Dependent on the initial activity measured, the actual volume of the sample measured deviated between 25 μl and 150 μl.

This series of measurements indicates, that yeast cells comprising the plasmid coding for the lipase-α-agglutinin fusion protein in fact express some lipase activity which is associated with the yeast cell.

An additional second assay was performed to further confirm the immobilization of activity of lipase on the yeast cell surface. Briefly, within this assay, the kinetics of the PNP (=paranitrophenyl) release from PNP-butyrate is determined by measurement of the OD at 400 nm. Therefore, 10 ml cultures containing yeast cells with either pSY1, pUR7034 or pUR2972B were centrifuged, the pellet was resuspended in 4 ml of buffer A (0.1M NaOAc, pH 5.0 and 1 mM PMSF), from this 4 ml 500 μl was centrifuged again and resuspended in 500 μl PNB-buffer (20 mM Tris-HCl, pH 9.0, 20 mM CaCl2, 25 mM NaCl), centrifuged once again, and finally resuspended in 400 μl PNB buffer. This fraction was used to determine the cell bound fraction of lipase.

The remaining 3500 μl were spun down, the pellet was resuspended in 4 ml A, to each of this, 40 μl laminarinase (ex mollusc, 1.25 mU/μl) was added and first incubated for 3 hours at 37° C., followed by an overnight incubation at 20° C. Then the reaction mixture, still containing intact cells, were centrifuged again and the supernatant was used to determined the amount of originally cell wall bound material released through laminarinase incubation. The final pellet was resuspended in 400 μl PNP buffer, to calculate the still cell associated part. The blank reaction of a defined volume of specific culture fraction in 4 ml assay buffer was determined, and than the reaction was started through addition of 80 μl of substrate solution (100 mM PNP-butyrate in methanol), and the reaction was observed at 25° C. at 400 nm in a spectrophotometer.

|  | cell bound activity* | activity in the medium | laminarinase extract | laminarinase extracted cells | OD660 |
|---|---|---|---|---|---|
| pSY1 | 0.001 (116 μl) | 0.001 | 0.028 | 0.000 | 2.6 |
| pUR7034 | 0.293 (220 μl) | 0.446 | 0.076 | 0.985 | 2.36 |
| pUR2972B-(1) | 0.494 (143 μl) | 0.021 | 0.170 | 0.208 | 2.10 |

*unless otherwise mentioned, the volume of enzyme solution added was 20 μl

This result positively demonstrates that a significant amount of lipase activity is immobilized on the surface yeast cell, containing plasmid pUR2972B. Here again, incorporation took place in such a way, that the reaction was catalyzed by cell wall inserted lipase of intact cells, indicated into the exterior orientated immobilization. Furthermore, the release of a significant amount of lipase activity after incubation with laminarinase again demonstrates the presumably covalent incorporation of a heterologous enzyme through gene fusion with the C-terminal part of α-agglutinin.

3. Localization

The expression, secretion, and subsequent incorporation of the lipase-α-agglutinin fusion protein into the yeast cell wall was also confirmed through Immunofluorescent labelling with anti-lipolase serum essentially as described in EXAMPLE 1, item 2. Localization.

As can be seen in FIG. 15, the Immunofluorescent stain shows essentially an analogous picture as the α-galactosidase immuno stain, with clearly detectable reactivity on the outside of the cell surface (see FIG. 15 A showing a clear halo around the cells and FIG. B showing a lighter circle at the surface of the cells), but neither in the medium nor in the interior of the cells. Yeast cells expressing pUR2972B, the Humicola lipase-α-agglutinin fusion protein, become homogeneously stained on the surface, indicating the virtually entire irmnobiLization of a chimeric enzyme with an α-agglutinin C-terminus on the exterior of a yeast cell. In the performed control experiment SU10 yeast cells containing plasmid pUR7034 served as a control and here, no cell surface bound reactivity against the applied anti-lipase serum could be detected.

In a similar way variants of Humicola lipase, obtained via rDNA techniques, can be linked to the C-terminal part of α-agglutinin, which variants can have a higher stability during (inter)esterification processes.

EXAMPLE 3

Immobilized Humicola Lipase/α-Agglutinin on the Surface of S. cerevisiae (constitutive expression of immobilized enzyme system)

Plasmid pUR2972 as described in EXAMPLE 2 can be treated with EagI and HindIII and the about 2.2 kb fragment containing the lipase/α-agglutinin gene can be isolated. Plasmid pSY16 can be restricted with EagI and HindIII and between these sites the 2.2 kb fragment containing the lipase/α-agglutinin fragment can be ligated resulting in pUR2973. The part of this plasmid that is involved in the production of the chimeric enzyme is similar to pUR2972 with the exception of the signal sequence. Whereas pUR2972 contains the SUC2-invertase-signal sequence, pUR2973 contains the α-mating factor signal sequence (see reference 18). Moreover the plasmid pUR2973 contains the Leu2 marker gene with the complete promoter sequence, instead of the truncated promoter version of pUR2972.

EXAMPLE 4

Immobilized Geotrichum Lipase/α-Agglutinin on the Surface of S. cerevisiae

The construction and isolation of the 1.4 kb NheI/HindIII fragment comprising the C-terminal part of AGα-1 (α-agglutinin) gene has been described in EXAMPLE 1. For the in-frame gene fusion of the DNA coding for the C-terminal membrane anchor of α-agglutinin to the complete coding sequence of Geotichum candidum lipase B from strain CMICC 335426 (see FIG. 8 and SEQ ID NO: 11 and 12), the plasmid pUR2974 can be used. This plasmid, derived from the commercially available pBluescript II SK plasmid, contains the cDNA coding for the complete G. candidum lipase II on an 1850 bp long EcoRI/XhoI insert (see FIG. 9).

To develop an expression vector for S. cerevisiae with homologous signal sequences, the N-terminus of the mature lipase B was determined experimentally by standard techniques. The obtained amino acid sequence of "Gln-Ala-Pro-Thr-Ala-Val . . ." is in complete agreement with the cleavage site of the signal peptidase on the *G. candidum* lipase II (see reference 19).

For the fusion of the mature lipase B to the *S. cerevisiae* signal sequences of SUC2 (invertase) or α-mating factor (prepro-αMF) on one hand and the in-frame fusion to the 3' part of the AGα1 gene PCR technique can be used. The PCR primer lipo3 (see SEQ ID NO: 13) can be constructed in such a way, that the originally present EagI site in the 5'-part of the coding sequence (spanning codons 5–7 of the mature protein) will become inactivated without any alteration in the amino acid sequence. To facilitate the subsequent cloning procedures, the PCR primer can further contain a new EagI site at the 5' end, for the in-frame ligation to SUC2 signal sequence or prepro-αMF sequence, respectively. The corresponding PCR primer lipo4 (see SEQ ID NO: 16) contains an extra NheI site behind the nucleotides coding for the C-terminus of lipase B, to ensure the proper fusion to the C-terminal part of α-agglutinin.

PCR oligonucleotides for the in frame linkage of *G. candidum* lipase II to the SUC2 signal sequence and the C-terminal part of α-agglutinin.
a: N-terminal transition to either prepro αMF sequence or SUC2 signal sequence.

The Humicola lipase-α-agglutinin fusion protein coding sequence can be exchanged against the lipase B/α-agglutinin fusion construct described above by digestion of the described vector pUR2973 with EagI/HindIII, resulting in pUR2976 (see FIG. 9).

EXAMPLE 5

Immobilized *Rhizomucor miehei* Lipase/α-Agglutinin on the Surface of *S. cerevisiae*

The construction and isolation of the 1.4 kb NheI/HindIII fragment encoding the C-terminal part of α-agglutinin has been described in EXAMPLE 1. The plasmid pUR2980 contains a 1.25 kb cDNA fragment cloned into the SmaI site of commercially available pUC18, which (synthetically synthesizable) fragment encodes the complete coding sequence of triglyceride lipase of *Rhizomucor miehei* (see reference 20), an enzyme used in a number of processes to interesterify triacylglycerols (see reference 21) or to prepare biosurfactants (see reference 22). Beside the 269 codons of the mature lipase molecule, the fragment also harbours codons for the 24 amino acid signal peptide as well as 70

```
                    EagI    A    Q    A    P    R    P    S    L    N
primer lipo3: 5'-GGG GCG GCC GCG CAG GCC CCA AGG CGG TCT CTC AAT-3'
                     ||  ||| ||| |||  || ||| ||| ||| |||
lipaseII:            3'-GAC CGG GTC CGG GGT GCC GCC AGA GAG TTA-5'
(non-cod. strand, see SEQ ID NO: 14) )
``` b: C-terminal fusion to C part of α-agglutinin amino acids of the propeptide. PCR can easily be applied to

```
                S    N    F    E    T    D    V    N    L    Y    G
lipase:    5'-CA AAC TTT GAG ACT GAC GTT AAT CTC TAC GGT TAA AAC-3'
(cod. strand)   |  ||| ||| ||| ||| ||| ||| ||| ||| ||| ||| |||
primer lipo4:              3'-C TGA CTG CAA TTA GAG ATG CCA CGATCG CCCC-5'
                                                              NheI
(for the part of the lipase coding strand see SEQ ID NO: 15)
```

The PCR product with the modified ends can be generated by standard PCR protocols, using instead of the normal Ampli-Taq polymerase the new thermostable VENT polymerase, which also exhibits proofreading activity, to ensure an error-free DNA template. Through digestion of the formerly described plasmid pUR2972 with EagI (complete) and NheI (partial), the Humicola lipase fragment can be exchanged against the DNA fragment coding for lipase B, thereby generating the final *S. cerevisiae* expression vector pUR2975 (see FIG. 9).

ensure the proper fusion of the gene fragment encoding the mature lipase to the SUC2 signal sequence or the prepro α-mating factor sequence of *S. cerevisiae*, as well as the in-frame fusion to the described NheI/HindIII fragment. The following two primers, lipo5 (see SEQ ID NO: 17) and lipo6 (see SEQ ID NO: 20), will generate a 833 bp DNA fragment, which after Proteinase K treatment and digestion with EagI and NheI can be cloned as an 816 bp long fragment into the EagI/NheI digested plasmids pUR2972 and pUR2973, respectively (see FIG. 7).

```
                                    EagI    A    S    I    D    G    G    I
lipo5:                        5'-CCC GCG GCC GCG AGC ATT GAT GGT GGT ATC-3'
                                      ||| ||| ||| ||| ||| ||| ||| |||
lipase (non-cod. strand):              3'-TCG TAA CTA GCA CCA TAG-5'
(for the part of the lipase non-coding strand, see SEQ ID NO: 18)

N    T    G    L    C    T
lipase (cod. strand):           5'-AAC ACA GGC CTC TGT ACT-3'
                                   ||| ||| ||| ||| ||| |||
Lipo6:                          3'-TTG TGT CCG GAG ACA TGA CGATCGCGCC-5'
                                                                NheI
(for the part of the lipase coding strand, see SEQ ID NO: 19)
```

These new *S. cerevisiae* expression plasmids contain the GAL7 promoter, the invertase signal sequence (pUR2981) or the prepro-α-mating factor sequence (pUR2982), the chimeric *Rhizomucor miehei* lipase/α-agglutinin gene, the 2 μm sequence, the defective (truncated) Leu2 promoter and the Leu2 gene. These plasmids can be transformed into *S. cerevisiae* and grown and analyzed using protocols described in earlier EXAMPLES.

EXAMPLE 6

Immobilized *Aspergillus niger* Glucose Oxidase/ GPI Anchored Cell Wall Proteins on the Surface of *S. cerevisiae*

Glucose oxidase (β-D:oxygen 1-oxidoreductase, EC 1.1.3.4) from *Aspergillus niger* catalyses the oxidation of β-D-glucose to glucono-δ-lactone and the concomitant reduction of molecular oxygen to hydrogen peroxide. The fungal enzyme consists of a homodimer of molecular weight 150,000 containing two tightly bound FAD co-factors. Beside the use in glucose detection kits the enzyme is useful as a source of hydrogen peroxide in food preservation. The gene was cloned from both cDNA and genomic libraries, the single open reading frame contains no intervening sequences and encodes a protein of 605 amino acids (see reference 23).

With the help of two proper oligonucleotides the coding part of the sequence is adjusted in a one-step modifying procedure by PCR in such a way that a fusion gene product will be obtained coding for glucose oxidase and the C-terminal cell wall anchor of the FLO1 gene product or α-agglutinin. Thus, some of the plasmids described in former EXAMPLES can be utilized to integrate the corresponding sequence in-frame between one of the signal sequences used in the EXAMPLES and the NheI/HindIII part of the AGα1 gene.

Since dimerisation of the two monomers might be a prerequisite for activity, in an alternative approach the complete coding sequence for glucose oxidase without the GPI anchor can be expressed in *S. cerevisiae* transformant which already contains the fusion construct. This can be fulfilled by constitutive expression of the fusion construct containing the GPI anchor with the help of the GAPDH or PGK promoter for example. The unbound not-anchored monomer can be produced by using a DNA construct comprising an inducible promoter, as for instance the GAL7 promoter.

EXAMPLE 7

Process to Convert Raffinose, Stachyose and Similar Sugars in Soy Extracts with α-Galactosidase/α-Agglutinin Immobilized on Yeasts The yeast transformed with plasmid pUR2969 can be cultivated on large scale. At regular intervals during cultivation the washed cells should be analyzed on the presence of α-galactosidase activity on their surface with methods described in EXAMPLE 1. When both cell density and α-galactosidase activity/biomass reach their maximum, the yeast cells can then be collected by centrifugation and washed. The washed cells can then be added to soy extracts. The final concentration of the yeast cells can vary between 0.1 and 10 g/l, preferably the concentration should be above 1 g/l The temperature of the soy extract should be <8° C. to reduce the metabolic activity of the yeast cells. The conversion of raffinose and stachyose can be analyzed with HPLC methods and after 95% conversion of these sugars the yeasts cells can be removed by centrifugation and their α-galactosidase activity/g biomass can be measured. Centrifugates with a good activity can be used in a subsequent conversion process, whereas centrifugates with an activity of less then 50% of the original activity can be resuscitated in the growth medium and the cells can be allowed to recover for 2 to 4 hours. Thereafter the cells can be centrifuged, washed and subsequently be used in a subsequent conversion process.

EXAMPLE 8

Production of Biosurfactants Using Humicola Lipase/α-Agglutinin Immobilized on Yeasts.

The yeast transformed with plasmid pUR2972 or pUR2973 can be cultivated on large scale. At regular intervals during cultivation the washed cells can be analyzed on the presence of lipase activity on their surface with methods described in EXAMPLE 2. When both cell density and lipase/biomass reache their maximum, the yeast cells can be collected by centrifugation and washed. The washed cells can be suspended in a small amount of water and added to a reactor tank containing a mix of fatty acids, preferably of a chain length between 12–18 carbon atoms and sugars, preferably glucose, galactose or sucrose. The total concentration of the water (excluding the water in the yeast cells) might be below 0.1%. The final concentration of the yeast cells can vary between 0.1 and 10 g/l, preferably the concentration is above 1 g/l. The tank has to be kept under an atmosphere of $N_2$ and $CO_2$ in order to avoid oxidation of the (unsaturated) fatty acids and to minimize the metabolic activity of the yeasts. The temperature of mixture in the tank should be between 30–60° C., depending on type of fatty acid used. The conversion of fatty acids can be analyzed with GLC methods and after 95% conversion of these fatty acids the yeasts cells can be removed by centrifugation and their lipase activity/g biomass can be measured. Centrifugates with a good activity can be used in a subsequent conversion process, whereas centrifugates with an activity of less then 50% of the original activity can be resuscitated in the growth medium and the cells can be allowed to recover for 2 to 8 hours. Thereafter the cells can be centrifuged again, washed and used in a subsequent conversion process.

EXAMPLE 9

Production of Special Types of Triacylglycerols using *Rhizomucor miehei* Lipase/α-Agglutinin Immobilized on Yeasts.

The yeast transformed with plasmid pUR2981 or pUR2982 can be cultivated on a large scale. At regular intervals during cultivation the washed cells can be analyzed on the presence of lipase activity on their surface with methods described in EXAMPLE 1. When both cell density and lipase/biomass reach their maximum, the yeast cells can be collected by centrifugation and washed. The washed cells can be suspended in a small amount of water and can be added to a reactor tank containing a mix of various triacylglycerols and fatty acids. The total concentration of the water (excluding the water in the yeast cells) might be below 0.1%. The final concentration of the yeast cells can vary between 0.1 and 10 g/l, preferably the concentration is above 1 g/l. The tank has to be kept under an atmosphere of $N_2$ and $CO_2$ in order to avoid oxidation of the (unsaturated) fatty acids and to minimize the metabolic activity of the yeasts. The temperature of mixture in the tank should be between 30–70° C., depending on types of triacylglycerol and fatty acid used. The degree of interesterification can be analyzed with GLC/MS methods and after formation of at least 80% of the theoretical value of the desired type of triacylglycerol the yeasts cells can be removed by centrifugation and their lipase activity/g biomass can be measured. Centrifugates with a good activity can be used in a subsequent conversion process, whereas centrifugates with an activity of less then 50% of the original activity is resuscitated in the growth medium and the cells should be allowed to recover 2 to 8 hours. After that the cells can be centrifuged, washed and used in a subsequent interesterification process.

Baker's yeasts of strain MT302/1C, transformed with either plasmid pSY13 or plasmid pUR2969 (described in EXAMPLE 1) were deposited under the Budapest Treaty at the Centraalbureau voor Schimmelcultures (CBS) on Jul. 3, 1992 under provisional numbers 330.92 and 329.92, respectively.

EXAMPLE 10

Immobilized Humicola Lipase/FLO1 Fusion on the Surface of S. cerevisiae

Flocculation, defined as "the (reversible) aggregation of dispersed yeast cells into flocs" (see reference 24), is the most important feature of yeast strains in industrial fermentations. Beside this it is of principal interest, because it is a property associated with cell wall proteins and it is a quantitative characteristic. One of the genes associated with the flocculation phenotype in S. cerevisiae is the FLO1 gene. The gene is located at approximately 24 kb from the right end of chromosome I and the DNA sequence of a clone containing major parts of FLO1 gene has very recently been determined (see reference 26). The sequence is given in FIG. 11 and SEQ ID NO: 21 and 22. The cloned fragment appeared to be approximately 2 kb shorter than the genomic copy as judged from Southern and Northern hybridizations, but encloses both ends of the FLO1 gene. Analysis of the DNA sequence data indicates that the putative protein contains at the N-terminus a hydrophobic region which confirms a signal sequence for secretion, a hydrophobic C-terminus that might function as a signal for the attachment of a GPI-anchor and many glycosylation sites, especially in the C-terminus, with 46.6% serine and threonine in the arbitrarily defined C-terminus (aa 271-894). Hence, it is likely that the FLO1 gene product is localized in an orientated fashion in the yeast cell wall and may be directly involved in the process of interaction with neighbouring cells. The cloned FLO1 sequence might therefore be suitable for the immobilization of proteins or peptides on the cell surface by a different type of cell wall anchor.

Recombinant DNA constructs can be obtained, for example by utilizing the DNA coding for amino acids 271–894 of the FLO1 gene product, i.e. polynucleotide 811-2682 of FIG. 11. Through application of two PCR primers pcrflo1 (see SEQ ID NO: 23) and pcrflo2 (see SEQ ID NO: 26) NheI and HindIII sites can be introduced at both ends of the DNA fragment. In a second step, the 1.4 kb NheI/HindIII fragment present in pUR2972 (either A or B) containing the C-terminal part of α-agglutinin can be replaced by the 1.9 kb DNA fragment coding for the C-terminal part of the FLO1 protein, resulting in plasmid pUR2990 (see FIG. 12), comprising a DNA sequence encoding (a) the invertase signal sequence (SUC2) preceding (b) the fusion protein consisting of (b.1) the lipase of Humicola (see reference 16) followed by (b.2) the C-terminus of FLO1 protein (aa 271-894).

PCR oligonucleotides for the in frame connection of the genes encoding the Humicola lipase and the C-terminal part of the FLO1 gene product.

```
                                       S   N   Y   A   V   S   T
primer pcrflo1               5'- GAATTC GCT AGC AAT TAT GCT GTC AGT AAC - 3'
                                    NheI    ||| ||| ||| ||| ||| |||
FLO1 gene (non-coding strand)        3'- AGT TTA ATA CGA CAG TCA TGG TGA - 5'
(for the part of the non-coding strand, see SEQ ID NO: 24)

FLO1 coding strand           5'-AATAA AATTCGCGTTCTTTTTACG - 3'
                                  |||||||||||||||||||||
primer pcrflo2:                 3'-TTAAGCGCAAGAAAAATGC TTCGAACTCGAG - 5'
                                                        HindIII
(for the part of the coding strand, see SEQ ID NO: 25)
```

Plasmid pUR2972 (either A or B) can be restricted with NheI (partial) and HindIII and the NheI/HindIII fragment comprising the vector backbone and the lipase gene can be ligated to the correspondingly digested PCR product of the plasmid containing the FLO1 sequence, resulting in plasmid pUR2990, containing the GAL7 promoter, the S. cerevisiae invertase signal sequence, the chimeric lipase/FLO1 gene, the yeast 2 μm sequence, the defective Leu2 promoter and the Leu2 gene. This plasmid can be transformed into S. cerevisiae and the transformed cells can be cultivated in YP medium including galactose as inductor.

The expression, secretion, localization and activity of the chimeric lipase/FLO1 protein can be analyzed using similar procedures as given in Example 1.

LITERATURE REFERENCES:
1. Monsan, P., Combes, D. (1988) "Enzyme stabilization by immobilization"; in Meth. in Enzymol. Vol 137 584–598.
2. Kok, J. (1990) "Genetics of proteolytic systems of lactic acids bacteria" FEMS Microbiol. Rev. 87 15–54.
3. Conzelmann, A., Fankhauser, C., Desponds, C. (1990) "Myoinositol gets incorporated into numerous membrane glycoproteins of S. cerevisiae: Incorporation is dependent on phosphomannomutase" (SEC53). EMBO 9 653–661.
4. Lipke, P., N., Wojciechowicz, D., Kurjan, J. (1989) "AGα1 is the structural gene for the Saccharomyces cerevisiae α-agglutinin, a cell surface glycoprotein involved in cell-cell interactions during mating" Mol. Cell. Biol. 9 3155–3165.
5. Roy, A., Lu, C. F., Marykwas, D., Lipke, P., Kurja, J. (1991) "The AGA1 gene product is involved in cell surface attachment of the S. cerevisiae cell adhesion glycoprotein a-agglutinin", Mol. Cell. Biol. 11 4196–4206.
6. Teunissen, A. W. R. H., van den Berg, J. A., Steensma, H. Y. (1993) "Physical localization of the flocculation gene FLO1 on chromosome I of S. cerevisiae, Yeast 9 (1) 1–10.
7. Yanisch Perron, C., Viera, J., Messing, J. (1985) "Improved M13 phage cloning vectors and host strains: nucleotide sequence of the M13 mp18 and pUC19 vectors." Gene 33 103–119.

8. Chung, C. T., Niemela, S. L., Miller, R. H. (1989) "One step preparation of competent *E. coli*: Transformation and storage of bacterial cells in the same solution" Proc. Natl. Acad. Sci. USA 86 2172–2175.
9. Sanger, F., Nicklen, S., Coulson, A. R. (1977) "DNA sequencing with chain terminating inhibitors" Proc. Natl. Acad. Sci. USA 74 5463–5467.
10. Hsiao, K. (1991) "A fast and simple procedure for sequencing double stranded DNA with Sequenase" Nucl. Acids Res. 19 2787.
11. Klebe, R. J. J., Harriss, V., Sharp, Z. D., Douglas, M. G. (1983) "A general method for polyethylene glycol induces genetic transformation of bacteria and yeast" Gene 25 333–341.
12. Overbeeke, N., Fellinger, A. J., Toonen, M. Y., van Wassenaar, P. D., Verrips, C. T. (1989) "Cloning and nucleotide sequence of the α-galactosidase gene from *Cyamopsis tetragonoloba*" Plant Mol. Biol. 13 541–550.
13. Laemmli, U. K. (1970) "Cleavage of structural proteins during the assembly of heads of bacteriophage T4." Nature 227 680–685.
14. Towbin, H. Steahelin, T., Gordon, J. (1979) "Electrophoretic transfer of proteins from polyacrylamide gels to nitrocellulose sheets: Procedure and some applications" Proc. Natl. Acad. Sci. USA 76 4350–4354.
15. Watzele, M., Klis, F., Tanner, W. (1988) "The immunological and molecular characterization of α-agglutinin from *S. cerevisiae*" EMBO J. 7 1483–1488.
16. Boel. E., Huge-Jensen, B., Brown, J. D. (1989) "Humicola lipase and process for the production of recombinant Humicola lipases" EP-A1-0 305 216.
17. Verbakel, J. M. A. (1991) "Heterologous gene expression in the yeast *Saccharomyces cerevisiae*" PhD thesis, Rijksuniversiteit Utrecht, The Netherlands
18. Kurjan, J., Herskowitz, I. (1982) "Structure of a yeast Pheromone Gene (MFα): A putative α-Factor precursor contains four tandem copiers of mature α-factor" Cell 30 933–943.
19. Shimada, Y., Sugihara, A., Tominaga, Y., Iizumi, T., Tsunasawa, S. (1989) "cDNA molecular cloning of Geotrichum candidum lipase" J. Biochem. 106 383–388.
20. Boel, E., Huge-Jensen, B., Christensen, M., Thim, L., Fiil, N. (1988) "*Rhizomucor miehei* Triglyceride Lipase is Synthesized as a Precursor" Lipids, Vol.23, No 7, 701–706.
21. Schuch, R., Mukherjee, K. D. (1988) in "World conference on Biotechnology for the fat and oil industry" ISBN 0-935315-21-7, 328–329.
22. Kosaric, N., Cairus, W. L., Gray, N. C. C. (editors) (1987) "Biosurfactants and Biotechnology" Marcel Dekker Inc., New York, Vol. 25.
23. Frederick, K. R., Tung, J., Emerik, R. S., Masiarz, F. R., Chamberlain, S. H., Vasavada, A., Rosenberg, S. (1990) "Glucose oxidase from *Aspergillus niger*". J. Biol. Chem., Vol.265, No.7, 3793–3802.
24. Johnston, J. R., Reader, H. P. (1983) "Genetic control of flocculation" in 'Yeast Genetics, Fundamental and applied aspects', Spencer, J. F. T. (Editor), ISBN 0-540-90793-9, p. 205–224.
25. Schreuder, M. P., Brekelmans, S., Van den Ende, H., Klis, F. M. (1993) "Targeting of a Heterologous Protein to the Cell Wall of *Saccharomyces cerevisiae*" Yeast 9 399–409.
26. Teunissen, A. W. R. H., Holub, E., Van der Hucht, J., Van Den Berg, J. A., Steensma, H. Y. (1993) "Sequence of the Open reading frame of the FLO1 Gene from *Saccharomyces cerevisiae*" YEAST 9 423–427.
27. Harmsen, M. M., Langedijk, A. C., Van Tuinen, E., Geerse, R. H.; Raue, H. A., Maat, J. (1993) Effect of a pmr1 disruption and different signal sequences on the intracellular processing and secretion of *Cyamopsis tetragonoloba* α-galactosidase by *Saccharomyces cerevisiae* Gene 125 115–123.

We claim:

1. A method for immobilizing an enzyme comprising recombinanltly producing an enzyme or a functional fragment thereof linked to the exterior of a host cell, said method comprising localizing the enzyme or functional fragment thereof at the exterior of the cell wall of a fungus by linking the enzyme or the functional part thereof to the anchoring part of a cell wall anchoring protein, which anchoring part is derivable from the C-terrmal part of said anchoring protein.

2. A method according to claim 1 in which said fungus is a yeast.

3. The method of claim 1, in which said fungus is selected from the group consisting of yeasts belonging to the genera Candida, Debaryomyces, Hansenula, Kluyveromyces, Pichia and Saccharomyces, and molds belonging to the genera Aspergillus, Penicillium and Rhizopus.

4. A fungus containing an expressible first polynucleotide comprising a structural gene encoding a protein providing catalytic activity and at least a part of a gene encoding at least a C-terminal portion of an anchoring protein capable of anchoring in the cell wall of said fungus, said part encoding ar least the anchoring part of said anchoring protein, said first polynucleotide being present either in a vector or in the chromosome of said fungus.

5. The fungus of claim 4, further comprising a sequence encoding a signal peptide, said sequence being operably linked to said first polynucleotide such that the translation product of said first polynucleotide is secreted to the cell wall of said fungus.

6. The fungus of claim 5, wherein the signal peptide is derived from a protein selected from the group consisting of glycosyl-phosphatidyl-inositol (GPI) anchoring protein, $\alpha$-factor, $\alpha$-agglutinin, a-agglutinin, invertase or inulinase of yeasts, $\alpha$-amylase of Bacillus, and proteinases of lactic acid bacteria.

7. The fungus of claim 4, wherein the protein capable of anchoring in the cell wall of said fungus is selected from the group consisting of $\alpha$-agglutinin, a-agglutinin, flocculation protein, and Major Cell Wall Protein of a fungus.

8. The fungus of claim 4, wherein the protein providing catalytic activity is selected from the group consisting of a hydrolytic enzyme and an oxido-reductase.

9. The fungus of claim 8 wherein said hydrolytic enzyme is a lipase.

10. The fungus of claim 8 wherein said protein providing catalytic activity is an oxidase.

11. The fungus of claim 4, wherein the protein providing catalytic activity exhibits said catalytic activity when present in a multimeric form, said fungus further comprising a second polynucleotide comprising a structural gene encoding said protein providing catalytic activity operably linked to a sequence encoding a signal peptide ensuring secretion of the expression product of said second polynucleotide which is operably linked to a regulatable promoter.

12. The fungus of claim 11, wherein said second polynucleotide is present either in a separate vector than the first polynucleotide or is present in the chromosome of said fungus.

13. The fungus of claim 4, having at least one of said polynucleotides integrated in its chromosome.

14. The fungus of claim 4, having said protein providing catalytic activity immobilized at the exterior of its cell wall.

15. The fungus of claim 4, which is a yeast.

16. A process for carring out an enzymatic process by using an immobilized catalytically active protein, wherein a substrate for said catalytically active protein is contacted with the fungus of claim 4.

17. A process according to claim 16 in which the fungus is a yeast.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 6057 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Saccharomyces cerevisiae (ix) FEATURE:
        (A) NAME/KEY: CDS
        (B) LOCATION: 3653..5605
        (D) OTHER INFORMATION: /function= "sexual agglutinisation"
            /product= "alpha-agglutinin"

(xi) SEQUENCE DESCRIPTION: SEQ ID NO: 1:

AAGCTTTAGG TAAGGGAGGC AGGGGGAAAA GATACTGAAA TGACGGAAAA CGAGAATATG      60

GAGCAGGGAG CAACTTTTAG AGCTTTACCC GTTAAAAGGT CAAATCGAGG CTTCCTGCCT     120

TTGTCTGATT TTAGTAGTAC CGGAAGGTTT ATTACGCCCA AGAACAGTGC TTGAATTGAG     180

```
TTCTCGGGAC ACGGGAAAGA CAATGGAAGA AAAATTTACA TTCAGTAGCC TTATATATGA      240

AATGCTGCCA AGCCACGTCT TTATAAGTAG ATAATGTCCC ATGAGCTGAA CTATGGGAAT      300

TTATGACGCA GTTCATTGTA TATATATTAC ATTAACTCTT TAGTTTAACA TCTGAATTGT      360

TTTATAAAAT AACTTTTTGA ATTTTTTTAT GATCGCTTAG TTAAGTCTAT TATATCAGGT      420

TTTTTCATTC ATCATAATTG TTCGTTAAAT ATGAGTATAT TTAAATACAG GAATTAGTAT      480

CATTTGCAGT CACGAAAAGG GCCGTTTCAT AGAGAGTTTT CTTAATAAAG TTGAGGGTTT      540

CCGTGATAGT TTTGAGGGGT TGTTTGAACT AGATTTACGC TTACCTTTCA ACTGATTAAT      600

TTTTTCAGCG GGCTTATCAT AATCATCCAT CATAGCAGTC TTTCTGGACT TCGTCGAGGA      660

CTGGCTTTCT GAATTTTGAC GGTCCCTATT AGCTCCAGTT GGAGGAATTG AGTTACCTAC      720

AACTGGCAAG AGGTCTTTGT TTGGATTCAA AATAGGACTT TGTGGTAGCA GTTTGGTTTT      780

ATTCAATCTA AAGATATGAG AAACAGGTTT AAGTAAATC GATACTATTG TACCAATGTT       840

TAGCTCCAAT TCCTCCAAAA CGGTGGGATC TAATTTTGTG TTCATTTCTA TTAGTGGCAA      900

CTCTCCGTCC AGTACTGATT TTAAAGATTC AAAAGTTATC GCGTTTGATA TACGAGACGT      960

TTTCGTTAAT GACAGCAATC TCCAATACAT CAGTGTTTTA TCTCTTAAGT CAGGATTATT     1020

TTCGTGATCG GTGCATCCTT TTAATAAATC CATACAAAGT TCTTCAGTTT CCTTTGTAGG     1080

ATTTCTGATG AAGAATTTTA TTGCTGAGTT CAGAATGGAA AATTGCACTT CTAGCGTCTC     1140

ATTAAACATG TTTGAGGAAA AAACTCTAAA TAACTCCAGG TAGTTTGGAA TTACATCCGA     1200

ATATTGCGTT ATTATCCAGA TCATAGCGTT TTTTGATTCA GGTTCCTGTA CAACTTCAGT     1260

GTGTTTGACT AGTTCTGTTA CGTTTGCTTT AAAATTATTG GGATATTTCC TCAAAATATT     1320

TCTGAAAACC GAAATAATCT CCTGGACGAC ATAATCAACA CCGAATTCTA ACAAATCTAG     1380

TAGCACAGCG ACACAATCGT GTACAGAGTC TTCATCTAGC TTAACAGCGA GATTACCAAT     1440

GGCTCTGACT GATTTCCTTG ACATTTGAAT ATCAATATCT GTAGCATATT GTTCCAACTC     1500

TTCTAGAATT CTTGGTAATG TTTCCTTGTT AGCTAAAAGA TATAAACACT CTAATTTCGT     1560

GTCTTTGATG TATATGGGGT CATTGTACTC GATGAAAAAA TACGAAATGT CTAGCCTGAG     1620

TAGAGATGAC TCCCTACTCA ATAAAAGAAG AATAACGTTT CTTAATACTA AAAATTGTAA     1680

TTCAGGCGGC TTATCTAACA AAGCTATTAC AGAGTTAGAT AGCTTTTCGG CTAGAGTTTC     1740

TTTGATGACG TCAACATAAT TCAACAAGTA CATGATGAAT TTTAAAGAGT TCAACACTAC     1800

GTATGTGTTT ACTTGTTGCA GGTACGGTAA AGCTAGTTCG ATCATTTCAT GGGTATCCAA     1860

ATAATGCTGC GGCACAACCG AAGTCGTCAA AACTTCCAAA ACAGTAGCCT TATTCCACTC     1920

ATTTAATTCG GGTAAAAGTT CTAGCATGTC AAAAGCGAGT TCCAAGGGAA TCCTGAAGGT     1980

TCCATGTTAG CGTTTTTTTC GTGAATGGAA TATAAAGTAT GTAATGCAGC TACAATGACT     2040

TCTGGAGAGC TCGACTGTGC CTTTACAATG TCATGTAGAA TGCTTGATAA CCCCAATACC     2100

CTTTCATGAT CAATTTCATC TAAATCCAAC AGTGCGTAAA TTGCTGTCCT CGTCACTTGT     2160

TCAGGTGGAG ACTTGTGATT TACCAATGAA ATGATACAGT CGAAGGCCTG ATCAGATAGC     2220

TCTTTCACCG GGACTAATAC CAGAGTTCTT AGTGCCATTA TTTGTAACTT TCATCTCTG     2280

CTTTTGAAAT CGTCCATTAT AAATGGCAAA GCCTCTCTGG CCTGCTGAGG TTTTAATGCG     2340

CCGATCACCC TAATATACTC ATGGCAAATT CTTTTCACTT CTAGATCATC TTCAATTTGC     2400

CAAAATTTCA AGAGCTCAGA AAACAGAAGG GACATTTCGC CATAGTTTCC TAGAACCAAA     2460

TTGGCGATAA TTTTTCTCAG AGCATTTTTC CTTCTTGTTA TATTCGATTT AAACTTTTTT     2520

ACTCCAAAAT GTTGCAGATC TGTGACGATT TCATTTGCTT TATATCTGGC AAAAACTTTT     2580
```

```
TGATCGGACA TAAGCGAAAT ACGTCCTATT AATGAAGTGA ATGTTCTTGC TGTATTCCCT    2640

TCTTGTGCAG TAGATTAATT CTGTTTCCAG GCTGCGATAC TTTGATACCC AATACTAAAA    2700

GTTGATGATT TGAACGATCT CCTATTTCCT CGCACATTTT TGGAGCGATA CCCGGAAGAC    2760

AGAATCGCGA TGTTAAGAAA ATAGTTCTGA TGGCACTAAA GAGATCATGA TTAAGGAAAG    2820

GTAAGTGATA TGCATGAATG GGAATAGGCT TTCGAACTTG ACGATTAGT TCCTTATTTC     2880

TATCCATCTA ATCCTCCAAC TTCAATAGGC CTTATCTAGC TCAGAGCAGT ATTTAATTGA    2940

GAATAGTAGC TTAATTGAAA CCTTACTAAA AAAGTGTATG GTTACATAAG ATAAGGCGTT    3000

AAGAAGAGTA TACATATGCA TTATTCATTA CCAAGACCAC TATGAATAGT AATACCATAT    3060

TTAGCTTTTG AAACTCATGT TTTCTATTGT GTTGTTTCAA ATTCCTCTGT TAGGCTCAAT    3120

TTAGGTTAAT TAAATTATAA AAAAATATAA AAAATAAAGA AAGTTTATCC ATCGGCACCT    3180

CAATTCAATG GAGTAAACAG TTTCAACACT GAGTGGTGAA ACATTGAACA ACTACATGCA    3240

GTTTCCCGCC ACGAGGCAAG TGTAGGTCCT TTGTCCATTT CGCTTTGTTT TGCAGGTCAT    3300

TGATGACCTA ATTAGGAAGG TAGAAGCCGC TCCAGCTCAA TAAGGAAATG CTAAGGGTAC    3360

TCGCCTTTGG TGTTTTACCA TACAATGGCA GCTTTATGTC ACTTCATTCT TCAGTAACGG    3420

CGCTTAAATA TTCCCAAAAA CGTTACAATG GAATTGTTTG ATCATGTAAC GAAATGCAAT    3480

CTTCTAAAAA AAAAGCCATG TGAATCAAAA AAAGATTCCT TTTAGCATAC TATAAATATG    3540

CAAAATGCCC TCTATTTATT CTAGTAATCG TCCATTCTCA TATCTTCCTT ATATCAGTCG    3600

CCTCGCTTAA TATAGTCAGC ACAAAAGGAA CAACAATTCG CCAGTTTTCA AA ATG        3655
                                                          Met
                                                           1

TTC ACT TTT CTC AAA ATT ATT CTG TGG CTT TTT TCC TTG GCA TTG GCC    3703
Phe Thr Phe Leu Lys Ile Ile Leu Trp Leu Phe Ser Leu Ala Leu Ala
         5                   10                  15

TCT GCT ATA AAT ATC AAC GAT ATC ACA TTT TCC AAT TTA GAA ATT ACT    3751
Ser Ala Ile Asn Ile Asn Asp Ile Thr Phe Ser Asn Leu Glu Ile Thr
             20                  25                  30

CCA CTG ACT GCA AAT AAA CAA CCT GAT CAA GGT TGG ACT GCC ACT TTT    3799
Pro Leu Thr Ala Asn Lys Gln Pro Asp Gln Gly Trp Thr Ala Thr Phe
     35                  40                  45

GAT TTT AGT ATT GCA GAT GCG TCT TCC ATT AGG GAG GGC GAT GAA TTC    3847
Asp Phe Ser Ile Ala Asp Ala Ser Ser Ile Arg Glu Gly Asp Glu Phe
 50                  55                  60                  65

ACA TTA TCA ATG CCA CAT GTT TAT AGG ATT AAG CTA TTA AAC TCA TCG    3895
Thr Leu Ser Met Pro His Val Tyr Arg Ile Lys Leu Leu Asn Ser Ser
                 70                  75                  80

CAA ACA GCT ACT ATT TCC TTA GCG GAT GGT ACT GAG GCT TTC AAA TGC    3943
Gln Thr Ala Thr Ile Ser Leu Ala Asp Gly Thr Glu Ala Phe Lys Cys
             85                  90                  95

TAT GTT TCG CAA CAG GCT GCA TAC TTG TAT GAA AAT ACT ACT TTC ACA    3991
Tyr Val Ser Gln Gln Ala Ala Tyr Leu Tyr Glu Asn Thr Thr Phe Thr
         100                 105                 110

TGT ACT GCT CAA AAT GAC CTG TCC TCC TAT AAT ACG ATT GAT GGA TCC    4039
Cys Thr Ala Gln Asn Asp Leu Ser Ser Tyr Asn Thr Ile Asp Gly Ser
     115                 120                 125

ATA ACA TTT TCG CTA AAT TTT AGT GAT GGT GGT TCC AGC TAT GAA TAT    4087
Ile Thr Phe Ser Leu Asn Phe Ser Asp Gly Gly Ser Ser Tyr Glu Tyr
130                 135                 140                 145

GAG TTA GAA AAC GCT AAG TTT TTC AAA TCT GGG CCA ATG CTT GTT AAA    4135
Glu Leu Glu Asn Ala Lys Phe Phe Lys Ser Gly Pro Met Leu Val Lys
                 150                 155                 160

CTT GGT AAT CAA ATG TCA GAT GTG GTG AAT TTC GAT CCT GCT GCT TTT    4183
```

-continued

```
Leu Gly Asn Gln Met Ser Asp Val Val Asn Phe Asp Pro Ala Ala Phe
            165                 170                 175

ACA GAG AAT GTT TTT CAC TCT GGG CGT TCA ACT GGT TAC GGT TCT TTT       4231
Thr Glu Asn Val Phe His Ser Gly Arg Ser Thr Gly Tyr Gly Ser Phe
            180                 185                 190

GAA AGT TAT CAT TTG GGT ATG TAT TGT CCA AAC GGA TAT TTC CTG GGT       4279
Glu Ser Tyr His Leu Gly Met Tyr Cys Pro Asn Gly Tyr Phe Leu Gly
            195                 200                 205

GGT ACT GAG AAG ATT GAT TAC GAC AGT TCC AAT AAC AAT GTC GAT TTG       4327
Gly Thr Glu Lys Ile Asp Tyr Asp Ser Ser Asn Asn Asn Val Asp Leu
210                 215                 220                 225

GAT TGT TCT TCA GTT CAG GTT TAT TCA TCC AAT GAT TTT AAT GAT TGG       4375
Asp Cys Ser Ser Val Gln Val Tyr Ser Ser Asn Asp Phe Asn Asp Trp
                    230                 235                 240

TGG TTC CCG CAA AGT TAC AAT GAT ACC AAT GCT GAC GTC ACT TGT TTT       4423
Trp Phe Pro Gln Ser Tyr Asn Asp Thr Asn Ala Asp Val Thr Cys Phe
            245                 250                 255

GGT AGT AAT CTG TGG ATT ACA CTT GAC GAA AAA CTA TAT GAT GGG GAA       4471
Gly Ser Asn Leu Trp Ile Thr Leu Asp Glu Lys Leu Tyr Asp Gly Glu
            260                 265                 270

ATG TTA TGG GTT AAT GCA TTA CAA TCT CTA CCC GCT AAT GTA AAC ACA       4519
Met Leu Trp Val Asn Ala Leu Gln Ser Leu Pro Ala Asn Val Asn Thr
            275                 280                 285

ATA GAT CAT GCG TTA GAA TTT CAA TAC ACA TGC CTT GAT ACC ATA GCA       4567
Ile Asp His Ala Leu Glu Phe Gln Tyr Thr Cys Leu Asp Thr Ile Ala
290                 295                 300                 305

AAT ACT ACG TAC GCT ACG CAA TTC TCG ACT ACT AGG GAA TTT ATT GTT       4615
Asn Thr Thr Tyr Ala Thr Gln Phe Ser Thr Thr Arg Glu Phe Ile Val
                    310                 315                 320

TAT CAG GGT CGG AAC CTC GGT ACA GCT AGC GCC AAA AGC TCT TTT ATC       4663
Tyr Gln Gly Arg Asn Leu Gly Thr Ala Ser Ala Lys Ser Ser Phe Ile
            325                 330                 335

TCA ACC ACT ACT ACT GAT TTA ACA AGT ATA AAC ACT AGT GCG TAT TCC       4711
Ser Thr Thr Thr Thr Asp Leu Thr Ser Ile Asn Thr Ser Ala Tyr Ser
            340                 345                 350

ACT GGA TCC ATT TCC ACA GTA GAA ACA GGC AAT CGA ACT ACA TCA GAA       4759
Thr Gly Ser Ile Ser Thr Val Glu Thr Gly Asn Arg Thr Thr Ser Glu
355                 360                 365

GTG ATC AGT CAT GTG GTG ACT ACC AGC ACA AAA CTG TCT CCA ACT GCT       4807
Val Ile Ser His Val Val Thr Thr Ser Thr Lys Leu Ser Pro Thr Ala
370                 375                 380                 385

ACT ACC AGC CTG ACA ATT GCA CAA ACC AGT ATC TAT TCT ACT GAC TCA       4855
Thr Thr Ser Leu Thr Ile Ala Gln Thr Ser Ile Tyr Ser Thr Asp Ser
                    390                 395                 400

AAT ATC ACA GTA GGA ACA GAT ATT CAC ACC ACA TCA GAA GTG ATT AGT       4903
Asn Ile Thr Val Gly Thr Asp Ile His Thr Thr Ser Glu Val Ile Ser
            405                 410                 415

GAT GTG GAA ACC ATT AGC AGA GAA ACA GCT TCG ACC GTT GTA GCC GCT       4951
Asp Val Glu Thr Ile Ser Arg Glu Thr Ala Ser Thr Val Val Ala Ala
            420                 425                 430

CCA ACC TCA ACA ACT GGA TGG ACA GGC GCT ATG AAT ACT TAC ATC CCG       4999
Pro Thr Ser Thr Thr Gly Trp Thr Gly Ala Met Asn Thr Tyr Ile Pro
435                 440                 445

CAA TTT ACA TCC TCT TCT TTC GCA ACA ATC AAC AGC ACA CCA ATA ATC       5047
Gln Phe Thr Ser Ser Ser Phe Ala Thr Ile Asn Ser Thr Pro Ile Ile
450                 455                 460                 465

TCT TCA TCA GCA GTA TTT GAA ACC TCA GAT GCT TCA ATT GTC AAT GTG       5095
Ser Ser Ser Ala Val Phe Glu Thr Ser Asp Ala Ser Ile Val Asn Val
                    470                 475                 480

CAC ACT GAA AAT ATC ACG AAT ACT GCT GCT GTT CCA TCT GAA GAG CCC       5143
His Thr Glu Asn Ile Thr Asn Thr Ala Ala Val Pro Ser Glu Glu Pro
```

```
His Thr Glu Asn Ile Thr Asn Thr Ala Ala Val Pro Ser Glu Glu Pro
            485                 490                 495

ACT TTT GTA AAT GCC ACG AGA AAC TCC TTA AAT TCC TTC TGC AGC AGC       5191
Thr Phe Val Asn Ala Thr Arg Asn Ser Leu Asn Ser Phe Cys Ser Ser
            500                 505                 510

AAA CAG CCA TCC AGT CCC TCA TCT TAT ACG TCT TCC CCA CTC GTA TCG       5239
Lys Gln Pro Ser Ser Pro Ser Ser Tyr Thr Ser Ser Pro Leu Val Ser
        515                 520                 525

TCC CTC TCC GTA AGC AAA ACA TTA CTA AGC ACC AGT TTT ACG CCT TCT       5287
Ser Leu Ser Val Ser Lys Thr Leu Leu Ser Thr Ser Phe Thr Pro Ser
530                 535                 540                 545

GTG CCA ACA TCT AAT ACA TAT ATC AAA ACG GAA AAT ACG GGT TAC TTT       5335
Val Pro Thr Ser Asn Thr Tyr Ile Lys Thr Glu Asn Thr Gly Tyr Phe
                550                 555                 560

GAG CAC ACG GCT TTG ACA ACA TCT TCA GTT GGC CTT AAT TCT TTT AGT       5383
Glu His Thr Ala Leu Thr Thr Ser Ser Val Gly Leu Asn Ser Phe Ser
            565                 570                 575

GAA ACA GCA CTC TCA TCT CAG GGA ACG AAA ATT GAC ACC TTT TTA GTG       5431
Glu Thr Ala Leu Ser Ser Gln Gly Thr Lys Ile Asp Thr Phe Leu Val
        580                 585                 590

TCA TCC TTG ATC GCA TAT CCT TCT TCT GCA TCA GGA AGC CAA TTG TCC       5479
Ser Ser Leu Ile Ala Tyr Pro Ser Ser Ala Ser Gly Ser Gln Leu Ser
595                 600                 605

GGT ATC CAA CAG AAT TTC ACA TCA ACT TCT CTC ATG ATT TCA ACC TAT       5527
Gly Ile Gln Gln Asn Phe Thr Ser Thr Ser Leu Met Ile Ser Thr Tyr
610                 615                 620                 625

GAA GGT AAA GCG TCT ATA TTT TTC TCA GCT GAG CTC GGT TCG ATC ATT       5575
Glu Gly Lys Ala Ser Ile Phe Phe Ser Ala Glu Leu Gly Ser Ile Ile
                630                 635                 640

TTT CTG CTT TTG TCG TAC CTG CTA TTC TAAAACGGGT ACTGTACAGT             5622
Phe Leu Leu Leu Ser Tyr Leu Leu Phe
            645                 650

TAGTACATTG AGTCGAAATA TACGAAATTA TTGTTCATAA TTTTCATCCT GGCTCTTTTT     5682

TTCTTCAACC ATAGTTAAAT GGACAGTTCA TATCTTAAAC TCTAATAATA CTTTTCTAGT     5742

TCTTATCCTT TTCCGTCTCA CCGCAGATTT TATCATAGTA TTAAATTTAT ATTTTGTTCG     5802

TAAAAAGAAA AATTTGTGAG CGTTACCGCT CGTTTCATTA CCCGAAGGCT GTTTCAGTAG     5862

ACCACTGATT AAGTAAGTAG ATGAAAAAAT TTCATCACCA TGAAAGAGTT CGATGAGAGC     5922

TACTTTTTCA AATGCTTAAC AGCTAACCGC CATTCAATAA TGTTACGTTC TCTTCATTCT     5982

GCGGCTACGT TATCTAACAA GAGGTTTTAC TCTCTCATAT CTCATTCAAA TAGAAAGAAC     6042

ATAATCAAAA AGCTT                                                      6057

(2) INFORMATION FOR SEQ ID NO: 2:

(i) SEQUENCE CHARACTERISTICS:
        (A) LENGTH: 650 amino acids
        (B) TYPE: amino acid
        (D) TOPOLOGY: linear (ii) MOLECULE TYPE: protein (xi) SEQUENCE DESCRIPTION: SEQ ID NO: 2:

Met Phe Thr Phe Leu Lys Ile Ile Leu Trp Leu Phe Ser Leu Ala Leu
 1               5                  10                  15

Ala Ser Ala Ile Asn Ile Asn Asp Ile Thr Phe Ser Asn Leu Glu Ile
            20                  25                  30

Thr Pro Leu Thr Ala Asn Lys Gln Pro Asp Gln Gly Trp Thr Ala Thr
        35                  40                  45
```

```
Phe Asp Phe Ser Ile Ala Asp Ala Ser Ser Ile Arg Glu Gly Asp Glu
     50                  55                  60

Phe Thr Leu Ser Met Pro His Val Tyr Arg Ile Lys Leu Leu Asn Ser
 65                  70                  75                  80

Ser Gln Thr Ala Thr Ile Ser Leu Ala Asp Gly Thr Glu Ala Phe Lys
                 85                  90                  95

Cys Tyr Val Ser Gln Gln Ala Ala Tyr Leu Tyr Glu Asn Thr Thr Phe
            100                 105                 110

Thr Cys Thr Ala Gln Asn Asp Leu Ser Ser Tyr Asn Thr Ile Asp Gly
            115                 120                 125

Ser Ile Thr Phe Ser Leu Asn Phe Ser Asp Gly Gly Ser Ser Tyr Glu
            130                 135                 140

Tyr Glu Leu Glu Asn Ala Lys Phe Phe Lys Ser Gly Pro Met Leu Val
145                 150                 155                 160

Lys Leu Gly Asn Gln Met Ser Asp Val Val Asn Phe Asp Pro Ala Ala
                165                 170                 175

Phe Thr Glu Asn Val Phe His Ser Gly Arg Ser Thr Gly Tyr Gly Ser
                180                 185                 190

Phe Glu Ser Tyr His Leu Gly Met Tyr Cys Pro Asn Gly Tyr Phe Leu
            195                 200                 205

Gly Gly Thr Glu Lys Ile Asp Tyr Asp Ser Ser Asn Asn Asn Val Asp
            210                 215                 220

Leu Asp Cys Ser Ser Val Gln Val Tyr Ser Ser Asn Asp Phe Asn Asp
225                 230                 235                 240

Trp Trp Phe Pro Gln Ser Tyr Asn Asp Thr Asn Ala Asp Val Thr Cys
                245                 250                 255

Phe Gly Ser Asn Leu Trp Ile Thr Leu Asp Glu Lys Leu Tyr Asp Gly
                260                 265                 270

Glu Met Leu Trp Val Asn Ala Leu Gln Ser Leu Pro Ala Asn Val Asn
            275                 280                 285

Thr Ile Asp His Ala Leu Glu Phe Gln Tyr Thr Cys Leu Asp Thr Ile
            290                 295                 300

Ala Asn Thr Thr Tyr Ala Thr Gln Phe Ser Thr Thr Arg Glu Phe Ile
305                 310                 315                 320

Val Tyr Gln Gly Arg Asn Leu Gly Thr Ala Ser Ala Lys Ser Ser Phe
                325                 330                 335

Ile Ser Thr Thr Thr Thr Asp Leu Thr Ser Ile Asn Thr Ser Ala Tyr
                340                 345                 350

Ser Thr Gly Ser Ile Ser Thr Val Glu Thr Gly Asn Arg Thr Thr Ser
            355                 360                 365

Glu Val Ile Ser His Val Val Thr Thr Ser Thr Lys Leu Ser Pro Thr
370                 375                 380

Ala Thr Thr Ser Leu Thr Ile Ala Gln Thr Ser Ile Tyr Ser Thr Asp
385                 390                 395                 400

Ser Asn Ile Thr Val Gly Thr Asp Ile His Thr Thr Ser Glu Val Ile
                405                 410                 415

Ser Asp Val Glu Thr Ile Ser Arg Glu Thr Ala Ser Thr Val Val Ala
                420                 425                 430

Ala Pro Thr Ser Thr Thr Gly Trp Thr Gly Ala Met Asn Thr Tyr Ile
            435                 440                 445

Pro Gln Phe Thr Ser Ser Phe Ala Thr Ile Asn Ser Thr Pro Ile
            450                 455                 460

Ile Ser Ser Ser Ala Val Phe Glu Thr Ser Asp Ala Ser Ile Val Asn
465                 470                 475                 480
```

-continued

```
Val His Thr Glu Asn Ile Thr Asn Thr Ala Ala Val Pro Ser Glu Glu
            485                 490                 495

Pro Thr Phe Val Asn Ala Thr Arg Asn Ser Leu Asn Ser Phe Cys Ser
            500                 505                 510

Ser Lys Gln Pro Ser Ser Pro Ser Ser Tyr Thr Ser Ser Pro Leu Val
            515                 520                 525

Ser Ser Leu Ser Val Ser Lys Thr Leu Leu Ser Thr Ser Phe Thr Pro
            530                 535                 540

Ser Val Pro Thr Ser Asn Thr Tyr Ile Lys Thr Glu Asn Thr Gly Tyr
545                 550                 555                 560

Phe Glu His Thr Ala Leu Thr Thr Ser Ser Val Gly Leu Asn Ser Phe
            565                 570                 575

Ser Glu Thr Ala Leu Ser Ser Gln Gly Thr Lys Ile Asp Thr Phe Leu
            580                 585                 590

Val Ser Ser Leu Ile Ala Tyr Pro Ser Ser Ala Ser Gly Ser Gln Leu
            595                 600                 605

Ser Gly Ile Gln Gln Asn Phe Thr Ser Thr Ser Leu Met Ile Ser Thr
            610                 615                 620

Tyr Glu Gly Lys Ala Ser Ile Phe Phe Ser Ala Glu Leu Gly Ser Ile
625                 630                 635                 640

Ile Phe Leu Leu Leu Ser Tyr Leu Leu Phe
            645                 650
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer lipo1

(xi) SEQUENCE DESCRIPTION: SEQ ID NO: 3:

```
GGGGCGGCCG AGGTCTCGCA AGATCTGGA                                29
```

(2) INFORMATION FOR SEQ ID NO: 4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Part non-coding strand lipase (xi) SEQUENCE DESCRIPTION: SEQ ID NO: 4:

```
TTTGTCCAGG TCTTGCGAGA CCTCTCGACG AAT                           33
```

(2) INFORMATION FOR SEQ ID NO: 5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

-continued (vii) IMMEDIATE SOURCE:
    (B) CLONE: Part coding strand lipase (xi) SEQUENCE DESCRIPTION: SEQ ID NO: 5:

TTCGGGTTAA TTGGGACATG TCTTTAGTGC GA                    32

(2) INFORMATION FOR SEQ ID NO: 6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer lipo2

(xi) SEQUENCE DESCRIPTION: SEQ ID NO: 6:

CCCCAAGCTT AAGGCTAGCA AGACATGTCC CAATTAACCC            40

(2) INFORMATION FOR SEQ ID NO: 7:

(i) SEQUENCE CHARACTERISTICS:
        (A) LENGTH: 894 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Humicola lanuginosa (ix) FEATURE:
        (A) NAME/KEY: CDS
        (B) LOCATION: 72..884
        (D) OTHER INFORMATION: /product= "lipase"

(ix) FEATURE:
        (A) NAME/KEY: mat_peptide
        (B) LOCATION: 72..881
        (D) OTHER INFORMATION: /product= "lipase"

(xi) SEQUENCE DESCRIPTION: SEQ ID NO: 7:

GAATTCGTAG CGACGATATG AGGAGCTCCC TTGTGCTGTT CTTTGTCTCT GCGTGGACGG        60

CCTTGGCCAC G GCC GAG GTC TCG CAA GAT CTG TTT AAC CAG TTC AAT CTC        110
            Ala Glu Val Ser Gln Asp Leu Phe Asn Gln Phe Asn Leu
             1               5                  10

TTT GCA CAG TAT TCT GCT GCC GCA TAC TGC GGA AAA AAC AAT GAT GCC         158
Phe Ala Gln Tyr Ser Ala Ala Ala Tyr Cys Gly Lys Asn Asn Asp Ala
 15              20                  25

CCA GCT GGT ACA AAC ATT ACG TGC ACG GGA AAT GCC TGC CCC GAG GTA         206
Pro Ala Gly Thr Asn Ile Thr Cys Thr Gly Asn Ala Cys Pro Glu Val
 30              35                  40                  45

GAG AAG GCG GAT GCA ACG TTT CTC TAC TCG TTT GAA GAC TCT GGA GTG         254
Glu Lys Ala Asp Ala Thr Phe Leu Tyr Ser Phe Glu Asp Ser Gly Val
                 50                  55                  60

GGC GAT GTC ACC GGC TTC CTT GCT CTA GAC AAC ACG AAC AAA TTG ATC         302
Gly Asp Val Thr Gly Phe Leu Ala Leu Asp Asn Thr Asn Lys Leu Ile
             65                  70                  75

GTC CTC TCT TTC CGT GGC TCT CGT TCC ATA GAA AAC TGG ATC GGA AAT         350
Val Leu Ser Phe Arg Gly Ser Arg Ser Ile Glu Asn Trp Ile Gly Asn
         80                  85                  90

CTT AAC TTC GAC TTG AAA GAA ATA AAT GAC ATT TGC TCC GGC TGC AGG         398
Leu Asn Phe Asp Leu Lys Glu Ile Asn Asp Ile Cys Ser Gly Cys Arg

```
              95                  100                 105
GGA CAT GAC GGC TTC ACC TCG AGC TGG AGG TCT GTA GCC GAT ACG TTA      446
Gly His Asp Gly Phe Thr Ser Ser Trp Arg Ser Val Ala Asp Thr Leu
110                 115                 120                 125

AGG CAG AAG GTG GAG GAT GCT GTG AGG GAG CAT CCC GAC TAT CGC GTG      494
Arg Gln Lys Val Glu Asp Ala Val Arg Glu His Pro Asp Tyr Arg Val
                130                 135                 140

GTG TTT ACC GGA CAT AGC TTG GGT GGT GCA TTG GCA ACT GTT GCC GGA      542
Val Phe Thr Gly His Ser Leu Gly Gly Ala Leu Ala Thr Val Ala Gly
                145                 150                 155

GCA GAC CTG CGT GGA AAT GGG TAT GAC ATC GAC GTG TTT TCA TAT GGC      590
Ala Asp Leu Arg Gly Asn Gly Tyr Asp Ile Asp Val Phe Ser Tyr Gly
            160                 165                 170

GCC CCC CGA GTC GGA AAC AGG GCT TTT GCA GAA TTC CTG ACC GTA CAG      638
Ala Pro Arg Val Gly Asn Arg Ala Phe Ala Glu Phe Leu Thr Val Gln
        175                 180                 185

ACC GGC GGT ACC CTC TAC CGC ATT ACC CAC ACC AAT GAT ATT GTC CCT      686
Thr Gly Gly Thr Leu Tyr Arg Ile Thr His Thr Asn Asp Ile Val Pro
190                 195                 200                 205

AGA CTC CCG CCG CGC GAG TTC GGT TAC AGC CAT TCT AGC CCA GAG TAC      734
Arg Leu Pro Pro Arg Glu Phe Gly Tyr Ser His Ser Ser Pro Glu Tyr
                210                 215                 220

TGG ATC AAA TCT GGA ACC CTT GTC CCC GTC ACC CGA AAC GAC ATC GTG      782
Trp Ile Lys Ser Gly Thr Leu Val Pro Val Thr Arg Asn Asp Ile Val
                225                 230                 235

AAG ATA GAA GGC ATC GAT GCC ACC GGC GGC AAT AAC CAG CCT AAC ATT      830
Lys Ile Glu Gly Ile Asp Ala Thr Gly Gly Asn Asn Gln Pro Asn Ile
                240                 245                 250

CCG GAT ATC CCT GCG CAC CTA TGG TAC TTC GGG TTA ATT GGG ACA TGT      878
Pro Asp Ile Pro Ala His Leu Trp Tyr Phe Gly Leu Ile Gly Thr Cys
            255                 260                 265

CTT TAGTGCGAAG CTT                                                   894
Leu
270

(2) INFORMATION FOR SEQ ID NO: 8:

(i) SEQUENCE CHARACTERISTICS:
        (A) LENGTH: 270 amino acids
        (B) TYPE: amino acid
        (D) TOPOLOGY: linear (ii) MOLECULE TYPE: protein (xi) SEQUENCE DESCRIPTION: SEQ ID NO: 8:

Ala Glu Val Ser Gln Asp Leu Phe Asn Gln Phe Asn Leu Phe Ala Gln
  1               5                  10                  15

Tyr Ser Ala Ala Ala Tyr Cys Gly Lys Asn Asn Asp Ala Pro Ala Gly
                 20                  25                  30

Thr Asn Ile Thr Cys Thr Gly Asn Ala Cys Pro Glu Val Glu Lys Ala
             35                  40                  45

Asp Ala Thr Phe Leu Tyr Ser Phe Glu Asp Ser Gly Val Gly Asp Val
         50                  55                  60

Thr Gly Phe Leu Ala Leu Asp Asn Thr Asn Lys Leu Ile Val Leu Ser
 65                  70                  75                  80

Phe Arg Gly Ser Arg Ser Ile Glu Asn Trp Ile Gly Asn Leu Asn Phe
                 85                  90                  95

Asp Leu Lys Glu Ile Asn Asp Ile Cys Ser Gly Cys Arg Gly His Asp
                100                 105                 110

Gly Phe Thr Ser Ser Trp Arg Ser Val Ala Asp Thr Leu Arg Gln Lys
```

```
            115                 120                 125
Val Glu Asp Ala Val Arg Glu His Pro Asp Tyr Arg Val Val Phe Thr
    130                 135                 140
Gly His Ser Leu Gly Gly Ala Leu Ala Thr Val Ala Gly Ala Asp Leu
145                 150                 155                 160
Arg Gly Asn Gly Tyr Asp Ile Asp Val Phe Ser Tyr Gly Ala Pro Arg
                165                 170                 175
Val Gly Asn Arg Ala Phe Ala Glu Phe Leu Thr Val Gln Thr Gly Gly
            180                 185                 190
Thr Leu Tyr Arg Ile Thr His Thr Asn Asp Ile Val Pro Arg Leu Pro
        195                 200                 205
Pro Arg Glu Phe Gly Tyr Ser His Ser Ser Pro Glu Tyr Trp Ile Lys
210                 215                 220
Ser Gly Thr Leu Val Pro Val Thr Arg Asn Asp Ile Val Lys Ile Glu
225                 230                 235                 240
Gly Ile Asp Ala Thr Gly Gly Asn Asn Gln Pro Asn Ile Pro Asp Ile
                245                 250                 255
Pro Ala His Leu Trp Tyr Phe Gly Leu Ile Gly Thr Cys Leu
            260                 265                 270
```

(2) INFORMATION FOR SEQ ID NO: 9:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer (xi) SEQUENCE DESCRIPTION: SEQ ID NO: 9:

ATCCCTGCGC ACCTATGGTA CTTCGGGTTA ATTGGGACAT GTCTTGCTAG CCTTA      55

(2) INFORMATION FOR SEQ ID NO: 10:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer (xi) SEQUENCE DESCRIPTION: SEQ ID NO: 10:

AGCTTAAGGC TAGCAAGACA TGTCCCAATT AACCCGAAGT ACCATAGGTG CGCAGGGAT      59

(2) INFORMATION FOR SEQ ID NO: 11:

(i) SEQUENCE CHARACTERISTICS:
        (A) LENGTH: 1828 base pairs
        (B) TYPE: nucleic acid
        (C) STRANDEDNESS: double
        (D) TOPOLOGY: linear (ii) MOLECULE TYPE: cDNA to mRNA.

(vi) ORIGINAL SOURCE:
        (A) ORGANISM: Geotrichum candidum
        (B) STRAIN: CMICC 335426

-continued (ix) FEATURE:
    (A) NAME/KEY: CDS
    (B) LOCATION: 40..1731
    (D) OTHER INFORMATION: /product= "lipase"

(ix) FEATURE:
    (A) NAME/KEY: sig_peptide
    (B) LOCATION: 40..96

(ix) FEATURE:
    (A) NAME/KEY: mat_peptide
    (B) LOCATION: 97..1728
    (D) OTHER INFORMATION: /product= "lipase"
        /gene= "lipB"

(xi) SEQUENCE DESCRIPTION: SEQ ID NO: 11:

```
AATTCGGCAC GAGATTCCTT TGATTTGCAA CTGTTAATC ATG GTT TCC AAA AGC           54
                                            Met Val Ser Lys Ser
                                            -19             -15

TTT TTT TTG GCT GCG GCG CTC AAC GTA GTG GGC ACC TTG GCC CAG GCC         102
Phe Phe Leu Ala Ala Ala Leu Asn Val Val Gly Thr Leu Ala Gln Ala
            -10              -5                   1

CCC ACG GCC GTT CTT AAT GGC AAC GAG GTC ATC TCT GGT GTC CTT GAG         150
Pro Thr Ala Val Leu Asn Gly Asn Glu Val Ile Ser Gly Val Leu Glu
        5                   10                  15

GGC AAG GTT GAT ACC TTC AAG GGA ATC CCA TTT GCT GAC CCT CCT GTT         198
Gly Lys Val Asp Thr Phe Lys Gly Ile Pro Phe Ala Asp Pro Pro Val
    20                  25                  30

GGT GAC TTG CGG TTC AAG CAC CCC CAG CCT TTC ACT GGA TCC TAC CAG         246
Gly Asp Leu Arg Phe Lys His Pro Gln Pro Phe Thr Gly Ser Tyr Gln
 35              40                  45                  50

GGT CTT AAG GCC AAC GAC TTC AGC TCT GCT TGT ATG CAG CTT GAT CCT         294
Gly Leu Lys Ala Asn Asp Phe Ser Ser Ala Cys Met Gln Leu Asp Pro
            55                  60                  65

GGC AAT GCC TTT TCT TTG CTT GAC AAA GTA GTG GGC TTG GGA AAG ATT         342
Gly Asn Ala Phe Ser Leu Leu Asp Lys Val Val Gly Leu Gly Lys Ile
                70                  75                  80

CTT CCT GAT AAC CTT AGA GGC CCT CTT TAT GAC ATG GCC CAG GGT AGT         390
Leu Pro Asp Asn Leu Arg Gly Pro Leu Tyr Asp Met Ala Gln Gly Ser
            85                  90                  95

GTC TCC ATG AAT GAG GAC TGT CTC TAC CTT AAC GTT TTC CGC CCC GCT         438
Val Ser Met Asn Glu Asp Cys Leu Tyr Leu Asn Val Phe Arg Pro Ala
        100                 105                 110

GGC ACC AAG CCT GAT GCT AAG CTC CCC GTC ATG GTT TGG ATT TAC GGT         486
Gly Thr Lys Pro Asp Ala Lys Leu Pro Val Met Val Trp Ile Tyr Gly
115                 120                 125                 130

GGT GCC TTT GTG TTT GGT TCT TCT GCT TCT TAC CCT GGT AAC GGC TAC         534
Gly Ala Phe Val Phe Gly Ser Ser Ala Ser Tyr Pro Gly Asn Gly Tyr
                135                 140                 145

GTC AAG GAG AGT GTG GAA ATG GGC CAG CCT GTT GTG TTT GTT TCC ATC         582
Val Lys Glu Ser Val Glu Met Gly Gln Pro Val Val Phe Val Ser Ile
            150                 155                 160

AAC TAC CGT ACC GGC CCC TAT GGA TTC TTG GGT GGT GAT GCC ATC ACC         630
Asn Tyr Arg Thr Gly Pro Tyr Gly Phe Leu Gly Gly Asp Ala Ile Thr
        165                 170                 175

GCT GAG GGC AAC ACC AAC GCT GGT CTG CAC GAC CAG CGC AAG GGT CTC         678
Ala Glu Gly Asn Thr Asn Ala Gly Leu His Asp Gln Arg Lys Gly Leu
180                 185                 190

GAG TGG GTT AGC GAC AAC ATT GCC AAC TTT GGT GGT GAT CCC GAC AAG         726
Glu Trp Val Ser Asp Asn Ile Ala Asn Phe Gly Gly Asp Pro Asp Lys
195                 200                 205                 210

GTC ATG ATT TTC GGT GAG TCC GCT GGT GCC ATG AGT GTT GCT CAC CAG         774
Val Met Ile Phe Gly Glu Ser Ala Gly Ala Met Ser Val Ala His Gln
            215                 220                 225
```

```
CTT GTT GCC TAC GGT GGT GAC AAC ACC TAC AAC GGA AAG CAG CTT TTC      822
Leu Val Ala Tyr Gly Gly Asp Asn Thr Tyr Asn Gly Lys Gln Leu Phe
        230                 235                 240

CAC TCT GCC ATT CTT CAG TCT GGC GGT CCT CTT CCT TAC TTT GAC TCT      870
His Ser Ala Ile Leu Gln Ser Gly Gly Pro Leu Pro Tyr Phe Asp Ser
        245                 250                 255

ACT TCT GTT GGT CCC GAG AGT GCC TAC AGC AGA TTT GCT CAG TAT GCC      918
Thr Ser Val Gly Pro Glu Ser Ala Tyr Ser Arg Phe Ala Gln Tyr Ala
260                 265                 270

GGA TGT GAC ACC AGT GCC AGT GAT AAT GAC ACT CTG GCT TGT CTC CGC      966
Gly Cys Asp Thr Ser Ala Ser Asp Asn Asp Thr Leu Ala Cys Leu Arg
275                 280                 285                 290

AGC AAG TCC AGC GAT GTC TTG CAC AGT GCG CAG AAC TCG TAT GAT CTT     1014
Ser Lys Ser Ser Asp Val Leu His Ser Ala Gln Asn Ser Tyr Asp Leu
        295                 300                 305

AAG GAC CTG TTT GGT CTG CTC CCT CAA TTC CTT GGA TTT GGT CCC AGA     1062
Lys Asp Leu Phe Gly Leu Leu Pro Gln Phe Leu Gly Phe Gly Pro Arg
        310                 315                 320

CCC GAC GGC AAC ATT ATT CCC GAT GCC GCT TAT GAG CTC TAC CGC AGC     1110
Pro Asp Gly Asn Ile Ile Pro Asp Ala Ala Tyr Glu Leu Tyr Arg Ser
        325                 330                 335

GGT AGA TAC GCC AAG GTT CCC TAC ATT ACT GGC AAC CAG GAG GAT GAG     1158
Gly Arg Tyr Ala Lys Val Pro Tyr Ile Thr Gly Asn Gln Glu Asp Glu
        340                 345                 350

GGT ACT ATT CTT GCC CCC GTT GCT ATT AAT GCT ACC ACT ACT CCC CAT     1206
Gly Thr Ile Leu Ala Pro Val Ala Ile Asn Ala Thr Thr Thr Pro His
355                 360                 365                 370

GTT AAG AAG TGG TTG AAG TAC ATT TGT AGC CAG GCT TCT GAC GCT TCG     1254
Val Lys Lys Trp Leu Lys Tyr Ile Cys Ser Gln Ala Ser Asp Ala Ser
        375                 380                 385

CTT GAT CGT GTT TTG TCG CTC TAC CCC GGC TCT TGG TCG GAG GGT TCA     1302
Leu Asp Arg Val Leu Ser Leu Tyr Pro Gly Ser Trp Ser Glu Gly Ser
        390                 395                 400

CCA TTC CGC ACT GGT ATT CTT AAT GCT CTT ACC CCT CAG TTC AAG CGC     1350
Pro Phe Arg Thr Gly Ile Leu Asn Ala Leu Thr Pro Gln Phe Lys Arg
        405                 410                 415

ATT GCT GCC ATT TTC ACT GAT TTG CTG TTC CAG TCT CCT CGT CGT GTT     1398
Ile Ala Ala Ile Phe Thr Asp Leu Leu Phe Gln Ser Pro Arg Arg Val
        420                 425                 430

ATG CTT AAC GCT ACC AAG GAC GTC AAC CGC TGG ACT TAC CTT GCC ACC     1446
Met Leu Asn Ala Thr Lys Asp Val Asn Arg Trp Thr Tyr Leu Ala Thr
435                 440                 445                 450

CAG CTC CAT AAC CTC GTT CCA TTT TTG GGT ACT TTC CAT GGC AGT GAT     1494
Gln Leu His Asn Leu Val Pro Phe Leu Gly Thr Phe His Gly Ser Asp
        455                 460                 465

CTT CTT TTT CAA TAC TAC GTG GAC CTT GGC CCA TCT TCT GCT TAC CGC     1542
Leu Leu Phe Gln Tyr Tyr Val Asp Leu Gly Pro Ser Ser Ala Tyr Arg
        470                 475                 480

CGC TAC TTT ATC TCG TTT GCC AAC CAC CAC GAC CCC AAC GTT GGT ACC     1590
Arg Tyr Phe Ile Ser Phe Ala Asn His His Asp Pro Asn Val Gly Thr
        485                 490                 495

AAC CTC CAA CAG TGG GAT ATG TAC ACT GAT GCA GGC AAG GAG ATG CTT     1638
Asn Leu Gln Gln Trp Asp Met Tyr Thr Asp Ala Gly Lys Glu Met Leu
        500                 505                 510

CAG ATT CAT ATG ATT GGT AAC TCT ATG AGA ACT GAC GAC TTT AGA ATC     1686
Gln Ile His Met Ile Gly Asn Ser Met Arg Thr Asp Asp Phe Arg Ile
515                 520                 525                 530

GAG GGA ATC TCG AAC TTT GAG TCT GAC GTT ACT CTC TTC GGT TAATCCCATT 1738
Glu Gly Ile Ser Asn Phe Glu Ser Asp Val Thr Leu Phe Gly
        535                 540                 545
```

TAGCAAGTTT TGTGTATTTC AAGTATACCA GTTGATGTAA TATATCAATA GATTACAAAT    1798

TAATTAGTGA AAAAAAAAAA AAAAAAAAAC    1828

(2) INFORMATION FOR SEQ ID NO: 12:

(i) SEQUENCE CHARACTERISTICS:
        (A) LENGTH: 563 amino acids
        (B) TYPE: amino acio
        (D) TOPOLOGY: linear (ii) MOLECULE TYPE: protein (xi) SEQUENCE DESCRIPTION: SEQ ID NO: 12:

```
Met Val Ser Lys Ser Phe Phe Leu Ala Ala Ala Leu Asn Val Val Gly
-19             -15             -10                  -5

Thr Leu Ala Gln Ala Pro Thr Ala Val Leu Asn Gly Asn Glu Val Ile
              1              5                  10

Ser Gly Val Leu Glu Gly Lys Val Asp Thr Phe Lys Gly Ile Pro Phe
        15              20              25

Ala Asp Pro Pro Val Gly Asp Leu Arg Phe Lys His Pro Gln Pro Phe
 30              35              40              45

Thr Gly Ser Tyr Gln Gly Leu Lys Ala Asn Asp Phe Ser Ser Ala Cys
              50              55              60

Met Gln Leu Asp Pro Gly Asn Ala Phe Ser Leu Leu Asp Lys Val Val
              65              70              75

Gly Leu Gly Lys Ile Leu Pro Asp Asn Leu Arg Gly Pro Leu Tyr Asp
         80              85              90

Met Ala Gln Gly Ser Val Ser Met Asn Glu Asp Cys Leu Tyr Leu Asn
         95             100             105

Val Phe Arg Pro Ala Gly Thr Lys Pro Asp Ala Lys Leu Pro Val Met
110             115             120             125

Val Trp Ile Tyr Gly Gly Ala Phe Val Phe Gly Ser Ala Ser Tyr
              130             135             140

Pro Gly Asn Gly Tyr Val Lys Glu Ser Val Glu Met Gly Gln Pro Val
              145             150             155

Val Phe Val Ser Ile Asn Tyr Arg Thr Gly Pro Tyr Gly Phe Leu Gly
              160             165             170

Gly Asp Ala Ile Thr Ala Glu Gly Asn Thr Asn Ala Gly Leu His Asp
 175             180             185

Gln Arg Lys Gly Leu Glu Trp Val Ser Asp Asn Ile Ala Asn Phe Gly
190             195             200             205

Gly Asp Pro Asp Lys Val Met Ile Phe Gly Glu Ser Ala Gly Ala Met
              210             215             220

Ser Val Ala His Gln Leu Val Ala Tyr Gly Gly Asp Asn Thr Tyr Asn
              225             230             235

Gly Lys Gln Leu Phe His Ser Ala Ile Leu Gln Ser Gly Gly Pro Leu
         240             245             250

Pro Tyr Phe Asp Ser Thr Ser Val Gly Pro Glu Ser Ala Tyr Ser Arg
         255             260             265

Phe Ala Gln Tyr Ala Gly Cys Asp Thr Ser Ala Ser Asp Asn Asp Thr
270             275             280             285

Leu Ala Cys Leu Arg Ser Lys Ser Ser Asp Val Leu His Ser Ala Gln
              290             295             300

Asn Ser Tyr Asp Leu Lys Asp Leu Phe Gly Leu Leu Pro Gln Phe Leu
              305             310             315
```

```
Gly Phe Gly Pro Arg Pro Asp Gly Asn Ile Ile Pro Asp Ala Ala Tyr
        320             325             330

Glu Leu Tyr Arg Ser Gly Arg Tyr Ala Lys Val Pro Tyr Ile Thr Gly
        335             340             345

Asn Gln Glu Asp Glu Gly Thr Ile Leu Ala Pro Val Ala Ile Asn Ala
350             355             360             365

Thr Thr Thr Pro His Val Lys Lys Trp Leu Lys Tyr Ile Cys Ser Gln
            370             375             380

Ala Ser Asp Ala Ser Leu Asp Arg Val Leu Ser Leu Tyr Pro Gly Ser
        385             390             395

Trp Ser Glu Gly Ser Pro Phe Arg Thr Gly Ile Leu Asn Ala Leu Thr
        400             405             410

Pro Gln Phe Lys Arg Ile Ala Ala Ile Phe Thr Asp Leu Leu Phe Gln
        415             420             425

Ser Pro Arg Arg Val Met Leu Asn Ala Thr Lys Asp Val Asn Arg Trp
430             435             440             445

Thr Tyr Leu Ala Thr Gln Leu His Asn Leu Val Pro Phe Leu Gly Thr
            450             455             460

Phe His Gly Ser Asp Leu Leu Phe Gln Tyr Tyr Val Asp Leu Gly Pro
            465             470             475

Ser Ser Ala Tyr Arg Arg Tyr Phe Ile Ser Phe Ala Asn His His Asp
        480             485             490

Pro Asn Val Gly Thr Asn Leu Gln Gln Trp Asp Met Tyr Thr Asp Ala
        495             500             505

Gly Lys Glu Met Leu Gln Ile His Met Ile Gly Asn Ser Met Arg Thr
510             515             520             525

Asp Asp Phe Arg Ile Glu Gly Ile Ser Asn Phe Glu Ser Asp Val Thr
            530             535             540

Leu Phe Gly (2) INFORMATION FOR SEQ ID NO: 13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer lipo3

(xi) SEQUENCE DESCRIPTION: SEQ ID NO: 13:

GGGGCGGCCG CGCAGGCCCC AAGGCGGTCT CTCAAT                              36

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Part non-coding strand lipaseII (xi) SEQUENCE DESCRIPTION: SEQ ID NO: 14:

ATTGAGAGAC CGCCGTGGGG CCTGGGCCAG                                     30
```

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Part coding strand lipaseII (xi) SEQUENCE DESCRIPTION: SEQ ID NO: 15:

CAAACTTTGA GACTGACGTT AATCTCTACG GTTAAAAC                        38

(2) INFORMATION FOR SEQ ID NO: 16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer lipo4

(xi) SEQUENCE DESCRIPTION: SEQ ID NO: 16:

CCCCGCTAGC ACCGTAGAGA TTAACGTCAG TC                              32

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer lipo5

(xi) SEQUENCE DESCRIPTION: SEQ ID NO: 17:

CCCGCGGCCG CGAGCATTGA TGGTGGTATC                                  30

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Part non-coding strand lipase (xi) SEQUENCE DESCRIPTION: SEQ ID NO: 18:

GATACCACGA TCAATGCT                                                  18

(2) INFORMATION FOR SEQ ID NO: 19:

(i) SEQUENCE CHARACTERISTICS:
        (A) LENGTH: 18 base pairs
        (B) TYPE: nueleic acid
        (C) STRANDEDNESS: single
        (D) TOPOLOGY: linear (ii) MOLECULE TYPE: DNA (genomic)

(vii) IMMEDIATE SOURCE:
    (B) CLONE: Part coding strand lipase (xi) SEQUENCE DESCRIPTION: SEQ ID NO: 19:

```
AACACAGGCC TCTGTACT                                                  18
```

(2) INFORMATION FOR SEQ ID NO: 20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer lipo6

(xi) SEQUENCE DESCRIPTION: SEQ ID NO: 20:

```
CCGCGCTAGC AGTACAGAGG CCTGTGTT                                       28
```

(2) INFORMATION FOR SEQ ID NO: 21:

(i) SEQUENCE CHARACTERISTICS:
        (A) LENGTH: 2685 base pairs
        (B) TYPE: nucleic acid
        (C) STRANDEDNESS: double
        (D) TOPOLOGY: linear (ii) MOLECULE TYPE: DNA (genomic)

(iii) ORIGINAL SOURCE:
        (A) ORGANISM: Saccharomyces cerevisiae (vii) IMMEDIATE SOURCE:
        (B) CLONE: pYY105

(ix) FEATURE:
        (A) NAME/KEY: CDS
        (B) LOCATION: 1..2685
        (D) OTHER INFORMATION: /product= "Flocculation protein" /gene= nFLO1"

(xi) SEQUENCE DESCRIPTION: SEQ ID NO: 21:

```
ATG ACA ATG CCT CAT CGC TAT ATG TTT TTG GCA GTC TTT ACA CTT CTG      48
Met Thr Met Pro His Arg Tyr Met Phe Leu Ala Val Phe Thr Leu Leu
  1               5                  10                  15

GCA CTA ACT AGT GTG GCC TCA GGA GCC ACA GAG GCG TGC TTA CCA GCA      96
Ala Leu Thr Ser Val Ala Ser Gly Ala Thr Glu Ala Cys Leu Pro Ala
             20                  25                  30

GGC CAG AGG AAA AGT GGG ATG AAT ATA AAT TTT TAC CAG TAT TCA TTG     144
Gly Gln Arg Lys Ser Gly Met Asn Ile Asn Phe Tyr Gln Tyr Ser Leu
         35                  40                  45

AAA GAT TCC TCC ACA TAT TCG AAT GCA GCA TAT ATG GCT TAT GGA TAT     192
Lys Asp Ser Ser Thr Tyr Ser Asn Ala Ala Tyr Met Ala Tyr Gly Tyr
 50                  55                  60

GCC TCA AAA ACC AAA CTA GGT TCT GTC GGA GGA CAA ACT GAT ATC TCG     240
Ala Ser Lys Thr Lys Leu Gly Ser Val Gly Gly Gln Thr Asp Ile Ser
         65                  70                  75              80

ATT GAT TAT AAT ATT CCC TGT GTT AGT TCA TCA GGC ACA TTT CCT TGT     288
Ile Asp Tyr Asn Ile Pro Cys Val Ser Ser Ser Gly Thr Phe Pro Cys
                 85                  90                  95

CCT CAA GAA GAT TCC TAT GGA AAC TGG GGA TGC AAA GGA ATG GGT GCT     336
Pro Gln Glu Asp Ser Tyr Gly Asn Trp Gly Cys Lys Gly Met Gly Ala
            100                 105                 110
```

```
TGT TCT AAT AGT CAA GGA ATT GCA TAC TGG AGT ACT GAT TTA TTT GGT      384
Cys Ser Asn Ser Gln Gly Ile Ala Tyr Trp Ser Thr Asp Leu Phe Gly
        115                 120                 125

TTC TAT ACT ACC CCA ACA AAC GTA ACC CTA GAA ATG ACA GGT TAT TTT      432
Phe Tyr Thr Thr Pro Thr Asn Val Thr Leu Glu Met Thr Gly Tyr Phe
    130                 135                 140

TTA CCA CCA CAG ACG GGT TCT TAC ACA TTC AAG TTT GCT ACA GTT GAC      480
Leu Pro Pro Gln Thr Gly Ser Tyr Thr Phe Lys Phe Ala Thr Val Asp
145                 150                 155                 160

GAC TCT GCA ATT CTA TCA GTA GGT GGT GCA ACC GCG TTC AAC TGT TGT      528
Asp Ser Ala Ile Leu Ser Val Gly Gly Ala Thr Ala Phe Asn Cys Cys
                165                 170                 175

GCT CAA CAG CAA CCG CCG ATC ACA TCA ACG AAC TTT ACC ATT GAC GGT      576
Ala Gln Gln Gln Pro Pro Ile Thr Ser Thr Asn Phe Thr Ile Asp Gly
            180                 185                 190

ATC AAG CCA TGG GGT GGA AGT TTG CCA CCT AAT ATC GAA GGA ACC GTC      624
Ile Lys Pro Trp Gly Gly Ser Leu Pro Pro Asn Ile Glu Gly Thr Val
        195                 200                 205

TAT ATG TAC GCT GGC TAC TAT TAT CCA ATG AAG GTT GTT TAC TCG AAC      672
Tyr Met Tyr Ala Gly Tyr Tyr Tyr Pro Met Lys Val Val Tyr Ser Asn
    210                 215                 220

GCT GTT TCT TGG GGT ACA CTT CCA ATT AGT GTG ACA CTT CCA GAT GGT      720
Ala Val Ser Trp Gly Thr Leu Pro Ile Ser Val Thr Leu Pro Asp Gly
225                 230                 235                 240

ACC ACT GTA AGT GAT GAC TTC GAA GGG TAC GTC TAT TCC TTT GAC GAT      768
Thr Thr Val Ser Asp Asp Phe Glu Gly Tyr Val Tyr Ser Phe Asp Asp
                245                 250                 255

GAC CTA AGT CAA TCT AAC TGT ACT GTC CCT GAC CCT TCA AAT TAT GCT      816
Asp Leu Ser Gln Ser Asn Cys Thr Val Pro Asp Pro Ser Asn Tyr Ala
            260                 265                 270

GTC AGT ACC ACT ACA ACT ACA ACG GAA CCA TGG ACC GGT ACT TTC ACT      864
Val Ser Thr Thr Thr Thr Thr Thr Glu Pro Trp Thr Gly Thr Phe Thr
        275                 280                 285

TCT ACA TCT ACT GAA ATG ACC ACC GTC ACC GGT ACC AAC GGC GTT CCA      912
Ser Thr Ser Thr Glu Met Thr Thr Val Thr Gly Thr Asn Gly Val Pro
    290                 295                 300

ACT GAC GAA ACC GTC ATT GTC ATC AGA ACT CCA ACC AGT GAA GGT CTA      960
Thr Asp Glu Thr Val Ile Val Ile Arg Thr Pro Thr Ser Glu Gly Leu
305                 310                 315                 320

ATC AGC ACC ACC ACT GAA CCA TGG ACT GGC ACT TTC ACT TCG ACT TCC     1008
Ile Ser Thr Thr Thr Glu Pro Trp Thr Gly Thr Phe Thr Ser Thr Ser
                325                 330                 335

ACT GAG GTT ACC ACC ATC ACT GGA ACC AAC GGT CAA CCA ACT GAC GAA     1056
Thr Glu Val Thr Thr Ile Thr Gly Thr Asn Gly Gln Pro Thr Asp Glu
            340                 345                 350

ACT GTG ATT GTT ATC AGA ACT CCA ACC AGT GAA GGT CTA ATC AGC ACC     1104
Thr Val Ile Val Ile Arg Thr Pro Thr Ser Glu Gly Leu Ile Ser Thr
        355                 360                 365

ACC ACT GAA CCA TGG ACT GGT ACT TTC ACT TCT ACA TCT ACT GAA ATG     1152
Thr Thr Glu Pro Trp Thr Gly Thr Phe Thr Ser Thr Ser Thr Glu Met
    370                 375                 380

ACC ACC GTC ACC GGT ACT AAC GGT CAA CCA ACT GAC GAA ACC GTG ATT     1200
Thr Thr Val Thr Gly Thr Asn Gly Gln Pro Thr Asp Glu Thr Val Ile
385                 390                 395                 400

GTT ATC AGA ACT CCA ACC AGT GAA GGT TTG GTT ACA ACC ACC ACT GAA     1248
Val Ile Arg Thr Pro Thr Ser Glu Gly Leu Val Thr Thr Thr Thr Glu
                405                 410                 415

CCA TGG ACT GGT ACT TTT ACT TCG ACT TCC ACT GAA ATG TCT ACT GTC     1296
Pro Trp Thr Gly Thr Phe Thr Ser Ser Thr Glu Met Ser Thr Val
            420                 425                 430
```

```
ACT GGA ACC AAT GGC TTG CCA ACT GAT GAA ACT GTC ATT GTT GTC AAA        1344
Thr Gly Thr Asn Gly Leu Pro Thr Asp Glu Thr Val Ile Val Val Lys
            435                 440                 445

ACT CCA ACT ACT GCC ATC TCA TCC AGT TTG TCA TCA TCA TCT TCA GGA        1392
Thr Pro Thr Thr Ala Ile Ser Ser Ser Leu Ser Ser Ser Ser Ser Gly
450                 455                 460

CAA ATC ACC AGC TCT ATC ACG TCT TCG CGT CCA ATT ATT ACC CCA TTC        1440
Gln Ile Thr Ser Ser Ile Thr Ser Ser Arg Pro Ile Ile Thr Pro Phe
465                 470                 475                 480

TAT CCT AGC AAT GGA ACT TCT GTG ATT TCT TCC TCA GTA ATT TCT TCC        1488
Tyr Pro Ser Asn Gly Thr Ser Val Ile Ser Ser Ser Val Ile Ser Ser
            485                 490                 495

TCA GTC ACT TCT TCT CTA TTC ACT TCT TCT CCA GTC ATT TCT TCC TCA        1536
Ser Val Thr Ser Ser Leu Phe Thr Ser Ser Pro Val Ile Ser Ser Ser
500                 505                 510

GTC ATT TCT TCT TCT ACA ACA ACC TCC ACT TCT ATA TTT TCT GAA TCA        1584
Val Ile Ser Ser Ser Thr Thr Thr Ser Thr Ser Ile Phe Ser Glu Ser
            515                 520                 525

TCT AAA TCA TCC GTC ATT CCA ACC AGT AGT TCC ACC TCT GGT TCT TCT        1632
Ser Lys Ser Ser Val Ile Pro Thr Ser Ser Ser Thr Ser Gly Ser Ser
530                 535                 540

GAG AGC GAA ACG AGT TCA GCT GGT TCT GTC TCT TCT TCC TCT TTT ATC        1680
Glu Ser Glu Thr Ser Ser Ala Gly Ser Val Ser Ser Ser Ser Phe Ile
545                 550                 555                 560

TCT TCT GAA TCA TCA AAA TCT CCT ACA TAT TCT TCT TCA TCA TTA CCA        1728
Ser Ser Glu Ser Ser Lys Ser Pro Thr Tyr Ser Ser Ser Ser Leu Pro
            565                 570                 575

CTT GTT ACC AGT GCG ACA ACA AGC CAG GAA ACT GCT TCT TCA TTA CCA        1776
Leu Val Thr Ser Ala Thr Thr Ser Gln Glu Thr Ala Ser Ser Leu Pro
            580                 585                 590

CCT GCT ACC ACT ACA AAA ACG AGC GAA CAA ACC ACT TTG GTT ACC GTG        1824
Pro Ala Thr Thr Thr Lys Thr Ser Glu Gln Thr Thr Leu Val Thr Val
            595                 600                 605

ACA TCC TGC GAG TCT CAT GTG TGC ACT GAA TCC ATC TCC CCT GCG ATT        1872
Thr Ser Cys Glu Ser His Val Cys Thr Glu Ser Ile Ser Pro Ala Ile
            610                 615                 620

GTT TCC ACA GCT ACT GTT ACT GTT AGC GGC GTC ACA ACA GAG TAT ACC        1920
Val Ser Thr Ala Thr Val Thr Val Ser Gly Val Thr Thr Glu Tyr Thr
625                 630                 635                 540

ACA TGG TGC CCT ATT TCT ACT ACA GAG ACA ACA AAG CAA ACC AAA GGG        1968
Thr Trp Cys Pro Ile Ser Thr Thr Glu Thr Thr Lys Gln Thr Lys Gly
            645                 650                 655

ACA ACA GAG CAA ACC ACA GAA ACA ACA AAA CAA ACC ACG GTA GTT ACA        2016
Thr Thr Glu Gln Thr Thr Glu Thr Thr Lys Gln Thr Thr Val Val Thr
            660                 665                 670

ATT TCT TCT TGT GAA TCT GAC GTA TGC TCT AAG ACT GCT TCT CCA GCC        2064
Ile Ser Ser Cys Glu Ser Asp Val Cys Ser Lys Thr Ala Ser Pro Ala
            675                 680                 685

ATT GTA TCT ACA AGC ACT GCT ACT ATT AAC GGC GTT ACT ACA GAA TAC        2112
Ile Val Ser Thr Ser Thr Ala Thr Ile Asn Gly Val Thr Thr Glu Tyr
            690                 695                 700

ACA ACA TGG TGT CCT ATT TCC ACC ACA GAA TCG AGG CAA CAA ACA ACG        2160
Thr Thr Trp Cys Pro Ile Ser Thr Thr Glu Ser Arg Gln Gln Thr Thr
705                 710                 715                 720

CTA GTT ACT GTT ACT TCC TGC GAA TCT GGT GTG TGT TCC GAA ACT GCT        2208
Leu Val Thr Val Thr Ser Cys Glu Ser Gly Val Cys Ser Glu Thr Ala
            725                 730                 735

TCA CCT GCC ATT GTT TCG ACG GCC ACG GCT ACT GTG AAT GAT GTT GTT        2256
Ser Pro Ala Ile Val Ser Thr Ala Thr Ala Thr Val Asn Asp Val Val
            740                 745                 750
```

```
ACG GTC TAT CCT ACA TGG AGG CCA CAG ACT GCG AAT GAA GAG TCT GTC    2304
Thr Val Tyr Pro Thr Trp Arg Pro Gln Thr Ala Asn Glu Glu Ser Val
        755                 760                 765

AGC TCT AAA ATG AAC AGT GCT ACC GGT GAG ACA ACA ACC AAT ACT TTA    2352
Ser Ser Lys Met Asn Ser Ala Thr Gly Glu Thr Thr Thr Asn Thr Leu
770                 775                 780

GCT GCT GAA ACG ACT ACC AAT ACT GTA GCT GCT GAG ACG ATT ACC AAT    2400
Ala Ala Glu Thr Thr Thr Asn Thr Val Ala Ala Glu Thr Ile Thr Asn
785                 790                 795                 800

ACT GGA GCT GCT GAG ACG AAA ACA GTA GTC ACC TCT TCG CTT TCA AGA    2448
Thr Gly Ala Ala Glu Thr Lys Thr Val Val Thr Ser Ser Leu Ser Arg
            805                 810                 815

TCT AAT CAC GCT GAA ACA CAG ACG GCT TCC GCG ACC GAT GTG ATT GGT    2496
Ser Asn His Ala Glu Thr Gln Thr Ala Ser Ala Thr Asp Val Ile Gly
                820                 825                 830

CAC AGC AGT AGT GTT GTT TCT GTA TCC GAA ACT GGC AAC ACC AAG AGT    2544
His Ser Ser Ser Val Val Ser Val Ser Glu Thr Gly Asn Thr Lys Ser
                    835                 840                 845

CTA ACA AGT TCC GGG TTG AGT ACT ATG TCG CAA CAG CCT CGT AGC ACA    2592
Leu Thr Ser Ser Gly Leu Ser Thr Met Ser Gln Gln Pro Arg Ser Thr
850                 855                 860

CCA GCA AGC AGC ATG GTA GGA TAT AGT ACA GCT TCT TTA GAA ATT TCA    2640
Pro Ala Ser Ser Met Val Gly Tyr Ser Thr Ala Ser Leu Glu Ile Ser
865                 870                 875                 880

ACG TAT GCT GGC AGT GCA ACA GCT TAC TGG CCG GTA GTG GTT TAA        2685
Thr Tyr Ala Gly Ser Ala Thr Ala Tyr Trp Pro Val Val Val
                885                 890
```

(2) INFORMATION FOR SEQ ID NO: 22:

(i) SEQUENCE CHARACTERISTICS:
        (A) LENGTH: 894 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Thr Met Pro His Arg Tyr Met Phe Leu Ala Val Phe Thr Leu Leu
 1               5                  10                  15

Ala Leu Thr Ser Val Ala Ser Gly Ala Thr Glu Ala Cys Leu Pro Ala
                20                  25                  30

Gly Gln Arg Lys Ser Gly Met Asn Ile Asn Phe Tyr Gln Tyr Ser Leu
            35                  40                  45

Lys Asp Ser Ser Thr Tyr Ser Asn Ala Ala Tyr Met Ala Tyr Gly Tyr
        50                  55                  60

Ala Ser Lys Thr Lys Leu Gly Ser Val Gly Gly Gln Thr Asp Ile Ser
65                  70                  75                  80

Ile Asp Tyr Asn Ile Pro Cys Val Ser Ser Gly Thr Phe Pro Cys
                    85                  90                  95

Pro Gln Glu Asp Ser Tyr Gly Asn Trp Gly Cys Lys Gly Met Gly Ala
                100                 105                 110

Cys Ser Asn Ser Gln Gly Ile Ala Tyr Trp Ser Thr Asp Leu Phe Gly
            115                 120                 125

Phe Tyr Thr Thr Pro Thr Asn Val Thr Leu Glu Met Thr Gly Tyr Phe
        130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
```

-continued

```
                165                 170                 175
Ala Gln Gln Gln Pro Pro Ile Thr Ser Thr Asn Phe Thr Ile Asp Gly
                180                 185                 190

Ile Lys Pro Trp Gly Gly Ser Leu Pro Pro Asn Ile Glu Gly Thr Val
            195                 200                 205

Tyr Met Tyr Ala Gly Tyr Tyr Tyr Pro Met Lys Val Val Tyr Ser Asn
        210                 215                 220

Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
                245                 250                 255

Asp Leu Ser Gln Ser Asn Cys Thr Val Pro Asp Pro Ser Asn Tyr Ala
                260                 265                 270

Val Ser Thr Thr Thr Thr Thr Glu Pro Trp Thr Gly Thr Phe Thr
                275                 280                 285

Ser Thr Ser Thr Glu Met Thr Thr Val Thr Gly Thr Asn Gly Val Pro
        290                 295                 300

Thr Asp Glu Thr Val Ile Val Ile Arg Thr Pro Thr Ser Glu Gly Leu
305                 310                 315                 320

Ile Ser Thr Thr Thr Glu Pro Trp Thr Gly Thr Phe Thr Ser Thr Ser
                325                 330                 335

Thr Glu Val Thr Thr Ile Thr Gly Thr Asn Gly Gln Pro Thr Asp Glu
                340                 345                 350

Thr Val Ile Val Ile Arg Thr Pro Thr Ser Glu Gly Leu Ile Ser Thr
            355                 360                 365

Thr Thr Glu Pro Trp Thr Gly Thr Phe Thr Ser Thr Ser Thr Glu Met
        370                 375                 380

Thr Thr Val Thr Gly Thr Asn Gly Gln Pro Thr Asp Glu Thr Val Ile
385                 390                 395                 400

Val Ile Arg Thr Pro Thr Ser Glu Gly Leu Val Thr Thr Thr Thr Glu
                405                 410                 415

Pro Trp Thr Gly Thr Phe Thr Ser Thr Ser Thr Glu Met Ser Thr Val
            420                 425                 430

Thr Gly Thr Asn Gly Leu Pro Thr Asp Glu Thr Val Ile Val Val Lys
        435                 440                 445

Thr Pro Thr Thr Ala Ile Ser Ser Ser Leu Ser Ser Ser Ser Ser Gly
450                 455                 460

Gln Ile Thr Ser Ser Ile Thr Ser Ser Arg Pro Ile Ile Thr Pro Phe
465                 470                 475                 480

Tyr Pro Ser Asn Gly Thr Ser Val Ile Ser Ser Ser Val Ile Ser Ser
                485                 490                 495

Ser Val Thr Ser Ser Leu Phe Thr Ser Ser Pro Val Ile Ser Ser Ser
            500                 505                 510

Val Ile Ser Ser Ser Thr Thr Thr Ser Thr Ser Ile Phe Ser Glu Ser
            515                 520                 525

Ser Lys Ser Ser Val Ile Pro Thr Ser Ser Ser Thr Ser Gly Ser Ser
            530                 535                 540

Glu Ser Glu Thr Ser Ser Ala Gly Ser Val Ser Ser Ser Ser Phe Ile
545                 550                 555                 560

Ser Ser Glu Ser Ser Lys Ser Pro Thr Tyr Ser Ser Ser Ser Leu Pro
                565                 570                 575

Leu Val Thr Ser Ala Thr Thr Ser Gln Glu Thr Ala Ser Ser Leu Pro
            580                 585                 590
```

```
Pro Ala Thr Thr Thr Lys Thr Ser Glu Gln Thr Thr Leu Val Thr Val
            595                 600                 605
Thr Ser Cys Glu Ser His Val Cys Thr Glu Ser Ile Ser Pro Ala Ile
        610                 615                 620
Val Ser Thr Ala Thr Val Thr Val Ser Gly Val Thr Thr Glu Tyr Thr
625                 630                 635                 640
Thr Trp Cys Pro Ile Ser Thr Glu Thr Lys Gln Thr Lys Gly
            645                 650                 655
Thr Thr Glu Gln Thr Thr Glu Thr Thr Lys Gln Thr Thr Val Val Thr
            660                 665                 670
Ile Ser Ser Cys Glu Ser Asp Val Cys Ser Lys Thr Ala Ser Pro Ala
        675                 680                 685
Ile Val Ser Thr Ser Thr Ala Thr Ile Asn Gly Val Thr Thr Glu Tyr
        690                 695                 700
Thr Thr Trp Cys Pro Ile Ser Thr Thr Glu Ser Arg Gln Gln Thr Thr
705                 710                 715                 720
Leu Val Thr Val Thr Ser Cys Glu Ser Gly Val Cys Ser Glu Thr Ala
                725                 730                 735
Ser Pro Ala Ile Val Ser Thr Ala Thr Val Asn Asp Val Val
            740                 745                 750
Thr Val Tyr Pro Thr Trp Arg Pro Gln Thr Ala Asn Glu Glu Ser Val
            755                 760                 765
Ser Ser Lys Met Asn Ser Ala Thr Gly Glu Thr Thr Asn Thr Leu
        770                 775                 780
Ala Ala Glu Thr Thr Thr Asn Thr Val Ala Ala Glu Thr Ile Thr Asn
785                 790                 795                 800
Thr Gly Ala Ala Glu Thr Lys Thr Val Val Thr Ser Ser Leu Ser Arg
            805                 810                 815
Ser Asn His Ala Glu Thr Gln Thr Ala Ser Ala Thr Asp Val Ile Gly
            820                 825                 830
His Ser Ser Ser Val Val Ser Val Ser Glu Thr Gly Asn Thr Lys Ser
            835                 840                 845
Leu Thr Ser Ser Gly Leu Ser Thr Met Ser Gln Gln Pro Arg Ser Thr
            850                 855                 860
Pro Ala Ser Ser Met Val Gly Tyr Ser Thr Ala Ser Leu Glu Ile Ser
865                 870                 875                 880
Thr Tyr Ala Gly Ser Ala Thr Ala Tyr Trp Pro Val Val Val
                885                 890

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer pcrflo1

(xi) SEQUENCE DESCRIPTION: SEQ ID NO: 23:

GAATTCGCTA GCAATTATGC TGTCAGTACC                                              30

(2) INFORMATION FOR SEQ ID NO: 24:

(i) SEQUENCE CHARACTERISTICS:
        (A) LENGTH: 24 base pairs
```

```
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: Part non-coding sequence FLO1

(xi) SEQUENCE DESCRIPTION: SEQ ID NO: 24:

AGTGGTACTG ACAGCATAAT TTGA                                              24

(2) INFORMATION FOR SEQ ID NO: 25:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: Part coding sequence FLO1

(xi) SEQUENCE DESCRIPTION: SEQ ID NO: 25:

AATAAAATTC GCGTTCTTTT TACG                                              24

(2) INFORMATION FOR SEQ ID NO: 26:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: primer pcrflo2

(xi) SEQUENCE DESCRIPTION: SEQ ID NO: 26:

GAGCTCAAGC TTCGTAAAAA GAACGCGAAT T                                      31
```